US011999980B2

(12) United States Patent
Elleuche et al.

(10) Patent No.: US 11,999,980 B2
(45) Date of Patent: Jun. 4, 2024

(54) **NON-SPECIFIC NUCLEASES FROM THE GENUS *PSEUDOMONAS* FOR USE IN FACILITATING FLOW OF CELLS THROUGH A MICROFLUIDIC CHANNEL**

(71) Applicant: Miltenyi Biotec B.V. & Co. KG, Bergisch Gladbach (DE)

(72) Inventors: Skander Elleuche, Hamburg (DE); Sarah Schmitz, Cologne (DE); Stefan Miltenyi, Bergisch Gladbach (DE); Volker Nolle, Kurten (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 0 days.

(21) Appl. No.: 17/264,748

(22) PCT Filed: Jul. 26, 2019

(86) PCT No.: PCT/EP2019/070148
§ 371 (c)(1),
(2) Date: Jan. 29, 2021

(87) PCT Pub. No.: WO2020/025468
PCT Pub. Date: Feb. 6, 2020

(65) Prior Publication Data
US 2021/0301273 A1 Sep. 30, 2021

(30) Foreign Application Priority Data

Jul. 30, 2018 (EP) ..................... 18186232

(51) Int. Cl.
*C12N 9/22* (2006.01)
*C12N 9/96* (2006.01)
*G01N 1/40* (2006.01)

(52) U.S. Cl.
CPC .............. *C12N 9/22* (2013.01); *C12N 9/96* (2013.01); *G01N 1/4044* (2013.01)

(58) Field of Classification Search
None
See application file for complete search history.

(56) References Cited

U.S. PATENT DOCUMENTS 10,018,541 B2 7/2018 Miltenyi et al.
2009/0304668 A1 12/2009 Pritchard et al.

FOREIGN PATENT DOCUMENTS

| CN | 104195122 A | 12/2014 |
| WO | 2007122423 A1 | 11/2007 |
| WO | 2014131113 A1 | 9/2014 |

OTHER PUBLICATIONS

Schwardmann et al. (Applied Microbiology, Abstract, 2020, 104(5).*
Zhao et al. (Protein Sci., 1997, vol. 6, pp. 2655-2658).*
Benedik et al., "Serratia Marcescens and Its Extracellular Nuclease", FEMS Microbiology Letters, vol. 165, No. 1, Aug. 1, 1998, pp. 1-13.
Gottlin et al., "Catalytic Mechanism of the Phospholipase D Superfamily Proceeds Via a Covalent Phosphohistidine Intermediate", Proceedings of the National Academy of Sciences of the United States of America, vol. 95, Aug. 1998, pp. 9202-9207.
MacLellan et al., "Properties of the Major Non-Specific Endonuclease From the Strict Anaerobe Fibrobacter Succinogenes and Evidence for Disulfide Bond Formation in Vivo", Microbiology, vol. 147, Feb. 2001, pp. 315-323.
Application No. PCT/EP2019/070148 , International Preliminary Report on Patentability, dated Feb. 11, 2021, 7 pages.
Schwardmann et al., "Decoding Essential Amino Acid Residues in the Substrate Groove of a Non-Specific Nuclease from Pseudomonas syringae", Catalysts, vol. 9, No. 11, Nov. 9, 2019, 16 pages.
Song et al., "Characterization of a Novel Non-Specific Nuclease From Thermophilic Bacteriophage GBSVI", BMC Biotechnology, vol. 8, No. 1, Apr. 28, 2008, pp. 1-9.

* cited by examiner

*Primary Examiner* — Hope A Robinson
(74) *Attorney, Agent, or Firm* — Kilpatrick Townsend & Stockton LLP

(57) ABSTRACT

The present invention provides a composition comprising an isolated polypeptide having non-specific nuclease (NSN) activity for degrading nucleic acids comprising or consisting of at least 70% amino acid sequence identity to SEQ ID NO:2, wherein said polypeptide has NSN activity in a solution of about 4° C., and a cation complexing agent such as EDTA. Said composition may have preferentially a neutral to basic pH. A kit comprising said composition and a method using said composition are also disclosed.

15 Claims, 12 Drawing Sheets

Specification includes a Sequence Listing.

Fig. 1A

| DEFINITION in NCBI Entrez (https://blast.ncbi.nlm.nih.gov/Blast.cgi?PAGE=Proteins) | ACCESSION NO | SEQ ID NO: | FAMILY | IDENTITY |
|---|---|---|---|---|
| MULTISPECIES: phospholipase D family protein [Pseudomonas syringae group genomosp. 2] | WP_050543862.1 | 1 | Pseudomonadaceae | 100% (153/153) |
| MULTISPECIES: phospholipase D family protein [Pseudomonas syringae group] | WP_044424800.1 | 12 | Pseudomonadaceae | 100% (153/153) |
| phospholipase D family protein [Pseudomonas syringae group genomosp. 3] | WP_007247250.1 | 13 | Pseudomonadaceae | 100% (153/153) |
| MULTISPECIES: phospholipase D family protein [Pseudomonas syringae group genomosp. 2] | WP_054073041.1 | 14 | Pseudomonadaceae | 100% (153/153) |
| MULTISPECIES: phospholipase D family protein [Pseudomonas syringae group] | WP_005622153.1 | 15 | Pseudomonadaceae | 100% (153/153) |
| MULTISPECIES: phospholipase D family protein [Pseudomonas syringae group] | WP_050586616.1 | 16 | Pseudomonadaceae | 100% (153/153) |
| endonuclease [Pseudomonas amygdali pv. mori str. 301020] | EGH24620.1 | 17 | Pseudomonadaceae | 100% (153/153) |
| endonuclease [Pseudomonas savastanoi pv. glycinea str. B076] | EFW77478.1 | 18 | Pseudomonadaceae | 100% (153/153) |
| endonuclease [Pseudomonas syringae pv. tomato] | KGK97600.1 | 19 | Pseudomonadaceae | 100% (153/153) |
| endonuclease, partial [Pseudomonas savastanoi pv. glycinea str. race 4] | EGH17602.1 | 20 | Pseudomonadaceae | 100% (153/153) |
| MULTISPECIES: phospholipase D family protein [Pseudomonas syringae group] | WP_050428163.1 | 21 | Pseudomonadaceae | 99.3% (152/153) |
| phospholipase D family protein [Pseudomonas syringae] | WP_050575265.1 | 22 | Pseudomonadaceae | 99.3% (152/153) |
| MULTISPECIES: phospholipase D family protein [Pseudomonas syringae group] | WP_050426729.1 | 5 | Pseudomonadaceae | 99.3% (152/153) |
| MULTISPECIES: phospholipase D family protein [Pseudomonas syringae group] | WP_054984015.1 | 23 | Pseudomonadaceae | 99.3% (152/153) |
| endonuclease [Pseudomonas syringae pv. pisi str. 1704B] | EGH43964.1 | 24 | Pseudomonadaceae | 99.3% (152/153) |
| endonuclease [Pseudomonas amygdali pv. lachrymans str. M302278] | EGH98754.1 | 25 | Pseudomonadaceae | 99.3% (152/153) |
| MULTISPECIES: phospholipase D family protein [Pseudomonas syringae] | WP_054999212.1 | 26 | Pseudomonadaceae | 99.3% (152/153) |
| phospholipase D family protein [Pseudomonas savastanoi] | WP_058886909.1 | 27 | Pseudomonadaceae | 99.3% (152/153) |
| phospholipase D family protein [Pseudomonas syringae group genomosp. 3] | WP_011107028.1 | 28 | Pseudomonadaceae | 99.3% (152/153) |
| MULTISPECIES: phospholipase D family protein [Pseudomonas syringae group] | WP_057429722.1 | 29 | Pseudomonadaceae | 99.3% (152/153) |

Fig. 1B

| DEFINTION in NCBI Entrez (https://blast.ncbi.nlm.nih.gov/Blast.cgi?PAGE=Proteins) | ACCESSION NO | SEQ ID NO: | FAMILY | IDENTITY |
|---|---|---|---|---|
| phospholipase D family protein [Pseudomonas amygdali] | WP_060409899.1 | 30 | Pseudomonadaceae | 99.3% (152/153) |
| MULTISPECIES: phospholipase D family protein [Pseudomonas syringae group genomosp. 2] | WP_044423964.1 | 31 | Pseudomonadaceae | 99.3% (152/153) |
| endonuclease [Pseudomonas syringae pv. theae ICMP 3923] | EPM73588.1 | 32 | Pseudomonadaceae | 99.3% (152/153) |
| phospholipase D family protein [Pseudomonas coronafaciens] | WP_081000062.1 | 33 | Pseudomonadaceae | 99.3% (152/153) |
| MULTISPECIES: phospholipase D family protein [Pseudomonas syringae group] | WP_060402478.1 | 34 | Pseudomonadaceae | 99.3% (152/153) |
| endonuclease [Pseudomonas amygdali pv. morsprunorum str. M302280] | EGH13453.1 | 35 | Pseudomonadaceae | 99.3% (152/153) |
| endonuclease [Pseudomonas coronafaciens pv. porri] | KOP60822.1 | 36 | Pseudomonadaceae | 99.3% (152/153) |
| phospholipase D family protein [Pseudomonas syringae] | WP_074910266.1 | 37 | Pseudomonadaceae | 98.7% (151/153) |
| Plasmid conjugative transfer endonuclease [Pseudomonas amygdali pv. myricae] | KPX96694.1 | 38 | Pseudomonadaceae | 98.7% (151/153) |
| MULTISPECIES: phospholipase D family protein [Pseudomonas syringae group] | WP_019740841.1 | 39 | Pseudomonadaceae | 98.7% (151/153) |
| phospholipase D family protein [Pseudomonas amygdali] | WP_054071640.1 | 40 | Pseudomonadaceae | 98.7% (151/153) |
| phospholipase D family protein [Pseudomonas coronafaciens] | WP_053480958.1 | 41 | Pseudomonadaceae | 98.7% (151/153) |
| phospholipase D family protein [Pseudomonas syringae group genomosp. 3] | WP_011106984.1 | 42 | Pseudomonadaceae | 98.7% (151/153) |
| phospholipase D family protein [Pseudomonas syringae group genomosp. 3] | WP_046463759.1 | 43 | Pseudomonadaceae | 98.7% (151/153) |
| Endonuclease [Pseudomonas amygdali pv. myricae] | KPB60520.1 | 44 | Pseudomonadaceae | 98.7% (151/153) |
| endonuclease [Pseudomonas coronafaciens pv. porri] | KOP54057.1 | 45 | Pseudomonadaceae | 98.7% (151/153) |
| phospholipase D family protein [Pseudomonas syringae] | WP_019331468.1 | 46 | Pseudomonadaceae | 98.7% (151/153) |
| phospholipase D family protein [Pseudomonas syringae] | WP_060414146.1 | 47 | Pseudomonadaceae | 98.7% (151/153) |
| phospholipase D family protein [Pseudomonas amygdali] | WP_057412354.1 | 48 | Pseudomonadaceae | 98.7% (151/153) |
| phospholipase D family protein [Pseudomonas syringae] | WP_099978265.1 | 49 | Pseudomonadaceae | 98.7% (151/153) |
| MULTISPECIES: phospholipase D family protein [Pseudomonas] | WP_074801697.1 | 50 | Pseudomonadaceae | 98.7% (151/153) |
| hypothetical protein ALO81_200342 [Pseudomonas cannabina] | KPW80723.1 | 51 | Pseudomonadaceae | 98.7% (151/153) |
| phospholipase D family protein [Pseudomonas syringae group genomosp. 3] | WP_050428411.1 | 52 | Pseudomonadaceae | 98.7% (151/153) |
| Endonuclease [Pseudomonas savastanoi pv. phaseolicola] | KPY14349.1 | 53 | Pseudomonadaceae | 98.7% (151/153) |

Fig. 1C

| DEFINITION in NCBI Entrez (https://blast.ncbi.nlm.nih.gov/Blast.cgi?PAGE=Proteins) | ACCESSION NO | SEQ ID NO: | FAMILY | IDENTITY |
|---|---|---|---|---|
| phospholipase D family protein [Pseudomonas syringae] | WP_057458761.1 | 54 | Pseudomonadaceae | 98.0% (150/153) |
| phospholipase D family protein [Pseudomonas coronafaciens] | WP_055004007.1 | 55 | Pseudomonadaceae | 98.0% (150/153) |
| Phospholipase D precursor [Pseudomonas syringae pv. tomato] | KUR47132.1 | 56 | Pseudomonadaceae | 98.0% (150/153) |
| MULTISPECIES: phospholipase D family protein [Pseudomonas syringae group] | WP_081051325.1 | 57 | Pseudomonadaceae | 98.0% (150/153) |
| endonuclease [Pseudomonas amygdali pv. morsprunorum] | KWS51884.1 | 58 | Pseudomonadaceae | 98.0% (150/153) |
| phospholipase D family protein [Pseudomonas amygdali] | WP_060406764.1 | 59 | Pseudomonadaceae | 98.0% (150/153) |
| phospholipase D family protein [Pseudomonas amygdali] | WP_010218287.1 | 60 | Pseudomonadaceae | 98.0% (150/153) |
| phospholipase D family protein [Pseudomonas amygdali] | WP_046835414.1 | 61 | Pseudomonadaceae | 97.4% (149/153) |
| phospholipase D family protein [Pseudomonas caricapapayae] | WP_055007563.1 | 62 | Pseudomonadaceae | 96.7% (148/153) |
| MULTISPECIES: phospholipase D family protein [Pseudomonas] | WP_048402802.1 | 63 | Pseudomonadaceae | 85.0% (130/153) |
| phospholipase D family protein [Pseudomonas sp. MWU12-2115] | WP_103486374.1 | 64 | Pseudomonadaceae | 73.9% (113/153) |
| phospholipase D family protein [Pseudomonas coleopterorum] | WP_090362547.1 | 65 | Pseudomonadaceae | 73.2% (112/153) |
| MULTISPECIES: phospholipase D family protein [Enterobacteriaceae] | WP_063277839.1 | 66 | Enterobacteriaceae | 68.6% (105/153) |
| phospholipase D family protein [Citrobacter freundii] | WP_015345226.1 | 67 | Enterobacteriaceae | 68.0% (104/153) |
| phospholipase D family protein [Acinetobacter nosocomialis] | WP_026036923.1 | 68 | Moraxellaceae | 68.0% (104/153) |
| MULTISPECIES: phospholipase D family protein [Enterobacteriaceae] | WP_042036424.1 | 10 | Enterobacteriaceae | 67.3% (103/153) |
| phospholipase D family protein [Escherichia coli] | WP_113418750.1 | 69 | Enterobacteriaceae | 67.3% (103/153) |
| phospholipase D family protein [Klebsiella pneumoniae] | WP_105446463.1 | 70 | Enterobacteriaceae | 67.3% (103/153) |
| phospholipase D family protein [Salmonella enterica] | WP_058671804.1 | 71 | Enterobacteriaceae | 64.7% (101/156) |
| MULTISPECIES: phospholipase D family protein [Enterobacterales] | WP_000731968.1 | 7 | Enterobacteriaceae | 58.9% (89/151) |
| phospholipase D family protein [Pantoea agglomerans] | WP_039390287.1 | 11 | Erwiniaceae | 57.0% (86/154) |

Fig. 14
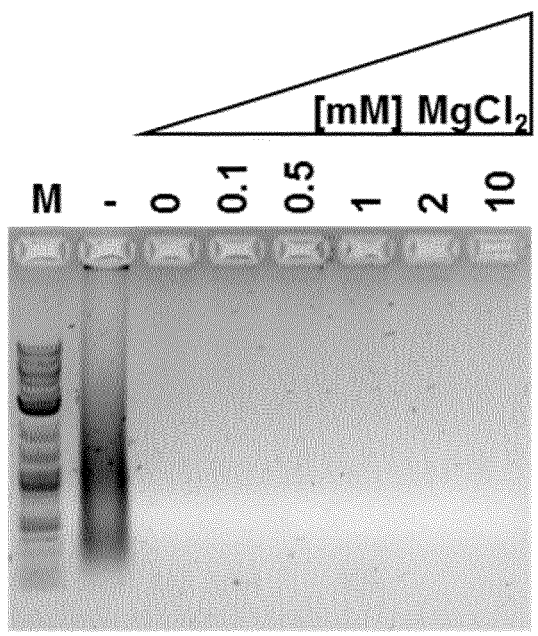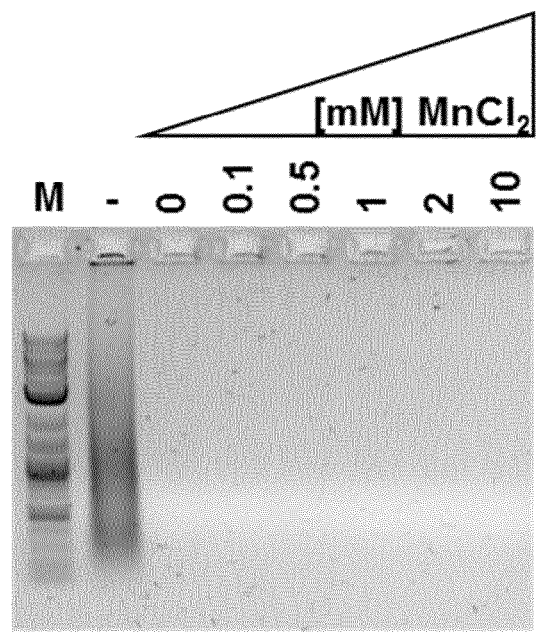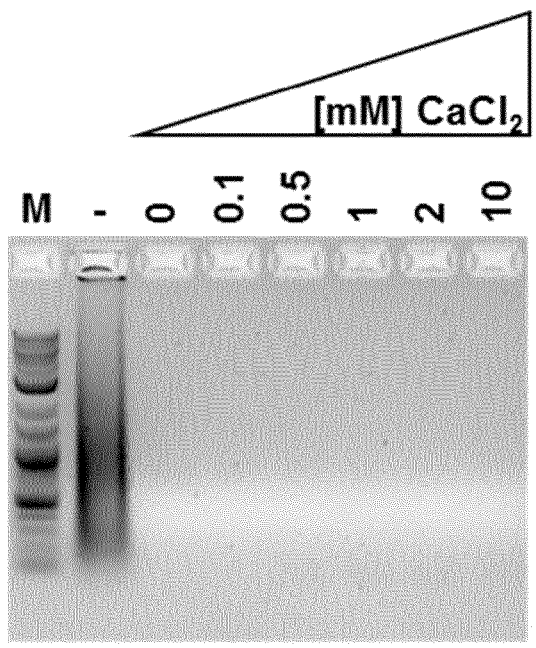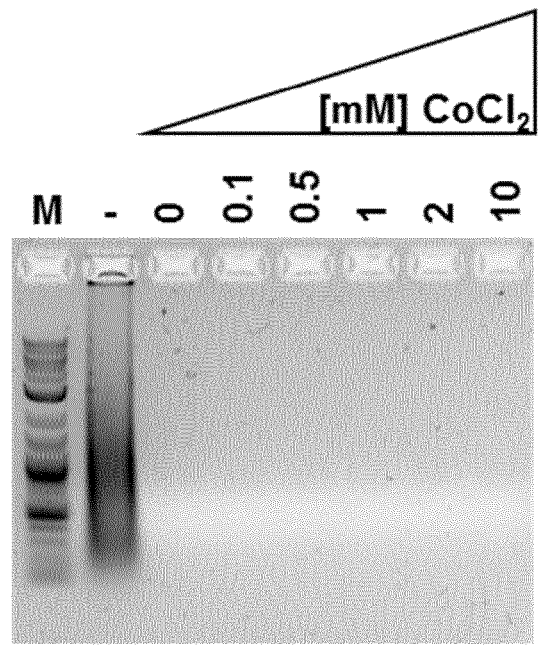

Fig. 15 A-B
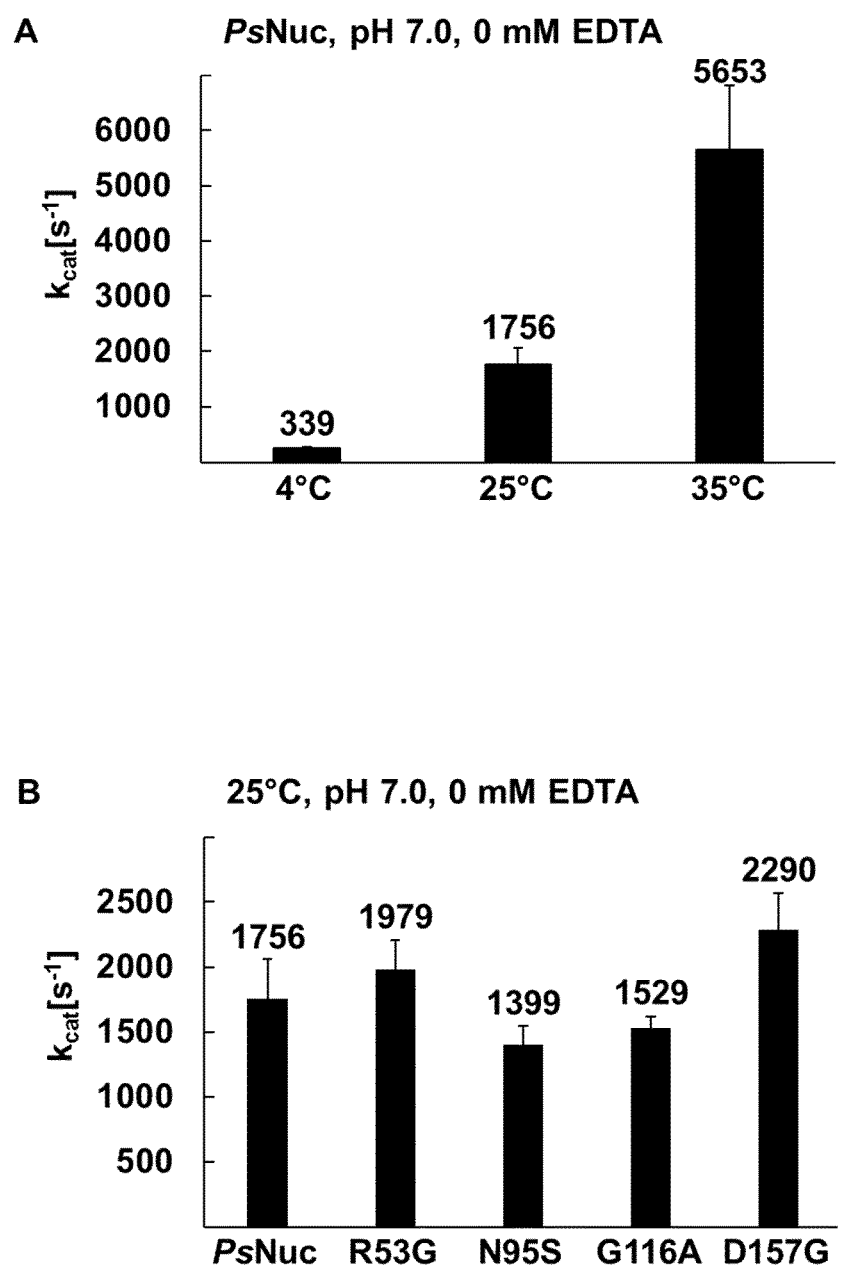

Fig. 15 C-D
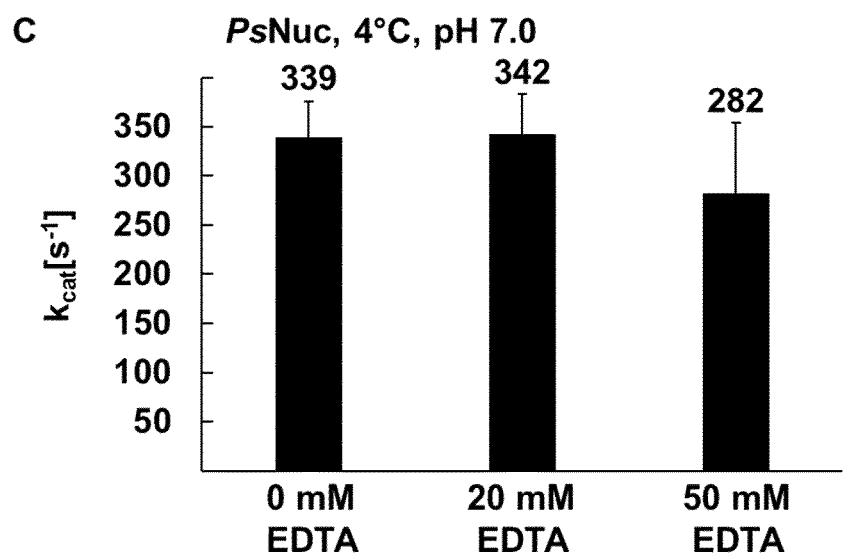
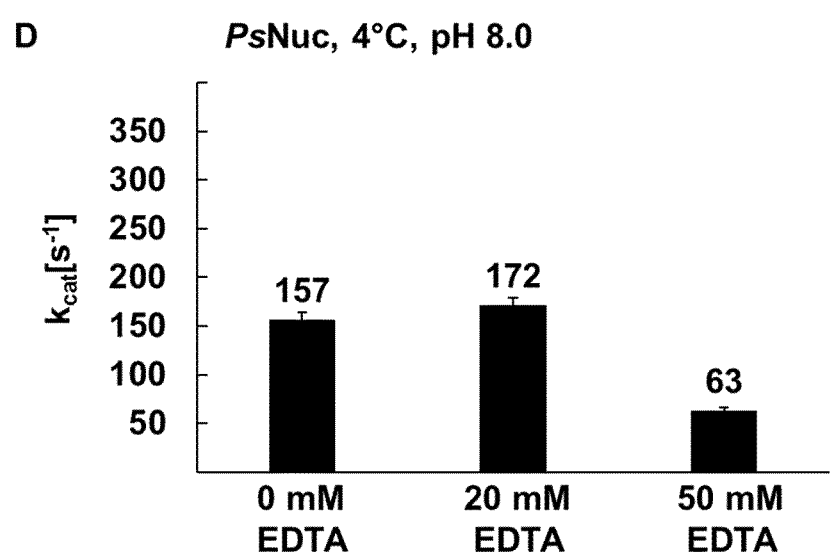

NON-SPECIFIC NUCLEASES FROM THE GENUS *PSEUDOMONAS* FOR USE IN FACILITATING FLOW OF CELLS THROUGH A MICROFLUIDIC CHANNEL

FIELD OF INVENTION

The present invention is in the field of enzyme technology, in particular this invention relates to the application of microbial non-specific nucleases that are active in solutions at temperatures down to about 4° C., preferentially combined with cation complexing agents such as EDTA and/or a neutral to basic pH.

BACKGROUND OF THE INVENTION

Nucleases are nucleic acids-degrading enzymes involved in natural processes including replication, recombination, repair, and restriction (Rangarajan and Shankar (2001) FEMS Microbiol Rev. 25:583-613). They are ubiquitous among all organisms and are localized to different tissues and to cellular sub-compartments such as the nucleus and organelles, they can be localized to the cytoplasm, attached to the cell membrane, or be secreted out of the cell. Nucleases either work in a sequence-specific (for example, a restriction enzyme) or sequence-independent type of action (non-specific nuclease). Non-specific nucleases (NSN) are of biotechnological importance with regard to their ability to cut, cleave, digest, or degrade nucleic acids including genomic DNA, plasmid DNA, and RNA in a sequence-independent manner. Nucleic acid impurities are unwanted subject of versatile biotechnological applications, including mRNA isolation, RT-PCR, qPCR, protein downstream processing, and manual or automated cell culturing, sorting, and separation processes. Nucleases are classified according to their primary sequences and assigned to different superfamilies. In addition, the superfamily of phospholipase D (PLD) proteins (EC 3.1.4.4) is composed of pro- and eukaryotic PLDs, phosphatidylserine synthetases, murine toxins, and nucleases. The distribution of PLD-family nucleases is mainly restricted to microbial prokaryotic species, while eukaryotes exhibit proteins of the PLD-superfamily that display hydrolytic activity towards lipids such as phosphatidylcholine or cardiolipin.

Zhao et al. (1997, Prot. Sci. 6:2655-2658) disclosed a non-specific bacterial nuclease called Nuc of the PLD-family from *Salmonella typhimurium* (later renamed as *Salmonella enterica* subsp. *enterica* serovar *Typhimurium*). For clarity this enzyme is named herein StN uc to distinguish it from other "Nuc" nucleases. StN uc is capable of degrading double and single stranded DNA in the presence of up to 1 mM EDTA. Its pH optimum is in the range from pH 5.0 to 6.0. The catalytic rate constant $k_{cat}$ was determined as 0.12 s$^{-1}$ when using the artificial substrate bis(4-nitrophenyl) phosphate at 37° C.

Gottlin et al. (1998, Proc Natl Acad Sci USA. 95:9202-9207) disclosed that StN uc exhibited a catalytic rate constant $k_{cat}$ of 3.5 s$^{-1}$ towards the artificial substrate p-nitrophenyl phenylphosphonate at a pH of 7.0 and 30° C. These authors further state that an accurate measurement was "difficult because of the extremely low enzyme activity".

Benedik and Strych (1998, FEMS Microbiol Lett. 165: 1-13) disclosed a non-specific bacterial nuclease from *Serratia marcescens*. This enzyme is commercially available under the tradename Benzonase® by Merck; its manual (catalog number 70664-3) discloses that the enzyme displays activity of degrading both RNA and DNA at pH 6.0 to 10.0 and at a temperature of 4° C. to 42° C., wherein the maximum activity is reached at 37° C. in a pH range between 8.0 and 9.2. The enzyme is inactive in the presence of >1 mM EDTA.

Song and Zhang (2008, BMC Biotechnol. 8:43) disclosed a non-specific nuclease from the thermophilic *Geobacillus* bacteriophage GBSV1. Its optimal temperature and pH were 60° C. and 7.5, respectively. It was found that Mn2+ or Zn2+ stimulates the activity of the nuclease. The enzymatic activity was reduced by some enzyme inhibitors such as EDTA. US2009/0304668A1 disclosed larval excretory/secretory products from *Lucilia sericata* comprising metal-ion activated DNase activity measured at 37° C. that was not inhibited in the presence of 5 mM EDTA.

Cell culturing is routinely conducted in solutions, buffers or media at neutral to basic pH (for example pH of about 7-8) and at temperatures required for growth (for example about 27-37° C.) and for storage, analysis and/or cell sorting (for example about 0-10° C.). Addition of cation complexing agents such as EDTA prevents cation-induced cell aggregation, and low temperatures minimize cell proliferation, cell activation, and cell death. However, damaged or lysed cells can release contaminating nucleic acids into the cell culture solution that may increase viscosity of the solution and/or may cause clogging of, for example, channels, matrices, and pores in cell culturing, cell sorting and cell separation devices, for example microfluidic channels and filter pores. Non-specific degradation of nucleic acids in cell culture solutions (especially those containing cation complexing agents such as EDTA) is desirable to prevent said viscosity increase and clogging.

Therefore, there is a need in the art for alternative and/or improved non-specific nucleases that have non-specific nuclease (NSN) activities in a low-temperature solution such as a about 4° C. solution, preferentially in combination with further conditions: in a solution comprising a cation complexing agent such as EDTA, in a solution having a neutral to basic pH, and/or in combinations of these conditions. In addition, there is a need in the art for alternative and/or improved methods that use said non-specific nucleases, for example to reduce the viscosity of solutions comprising nucleic acids and/or to reduce or prevent clogging of channels, matrices, and pores that are in contact with solutions comprising nucleic acids in all kinds of said conditions.

SUMMARY OF THE INVENTION

The group of PLD-like nucleases encoded in the genome of members of the genus *Pseudomonas* are closely related to each other with sequences identities of mostly 96.7%-100%. Some have identities between 73.2% and 85.0%. These isozymes can be clearly distinguished from homologues in other species. The most closely related sequences in NCBI from outside the family of Pseudomonaceae are members of the families of Enterobacteriacea and Moraxellaceae including isoenzymes identified in species of the genera *Salmonella*, *Escherichia*, *Klebsiella*, *Citrobacter*, and *Acinetobacter* exhibiting 68.6% or less sequence identity.

The inventors surprisingly identified a non-specific nuclease of the bacterium *Pseudomonas syringae* (herein called P.vNuc) and variants thereof comprising single point mutations in a sequence-based screening approach to be encoded within the genome of said bacterium *Pseudomonas syringae* and related bacterial species of the genus *Pseudomonas*. It was found that these enzymes exhibit non-specific nucleolytic activity towards nucleic and ribonucleic acids. Unexpectedly, P.vNuc tolerated cation chelating agents such as EDTA at concentrations up to 50 m and displayed maximum activity in a range of about pH 6 to 8 (see FIG. 10) because the herein disclosed non-specific nucleases are metal ion independent nucleases and are enzymatically active in the absence of metal ions (see FIG. 14). Moreover, the enzyme and variants thereof as disclosed herein showed NSN activity in the range from about 4° C. to about 50° C. (see FIG. 11). Variants of this enzyme exhibited high catalytic rate constants $k_{cat}$ in the range of about 1,400 s$^{-1}$ to 2,300 s$^{-1}$ at about 25° C. (see FIG. 15B) and about 340 s$^{-1}$ at about 4° C. (see FIG. 15A) which is about 15-24% of the value at about 25° C. ($k_{cat}$ values are dependent on temperature). Values of $k_{cat}$ from five different metal-ion dependent and EDTA-sensitive nucleases determined with sheared or unsheared genomic DNA has been described in the art to be in the range between 176 s$^{-1}$ and 2,100 s$^{-1}$ at 20° C. to 30° C. (MacFellan and Forsberg (2001) Microbiology 147:315-323). However, kinetic parameters of an EDTA-tolerant endonuclease of the PFD-superfamily were only determined for .SYNuc. Published $k_{cat}$ values of this enzyme are in the range from 0.12 s$^{-1}$ to 3.5 s$^{-1}$ (Zhao et al. (1997) Prot. Sci. 6:2655-2658; Gottlin et al. (1998) Proc Natl Acad Sci USA. 95:9202-9207).

Surprisingly, the herein disclosed non-specific nuclease of *Pseudomonas syringae* having the amino acid sequence of SEQ ID NO:2 and non-specific nucleases having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2 have NSN activity in a solution of about 4° C. Said NSN activity may be defined by a $k_{cat}$ value at about 4° C. of said nucleases of at least 10 s$^{-1}$, 20 s$^-$, 50 s$^-$, 100 s$^-$, 150 s$^-$, 200 s$^-$, 250 s$^-$, 300 s$^{-1}$, or 330 s$^{-1}$.

Surprisingly, the herein disclosed non-specific nuclease of *Pseudomonas syringae* having the amino acid sequence of SEQ ID NO:2 and non-specific nucleases having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2 have NSN activity in a solution of about 4° C., and a cation complexing agent such as EDTA in a range of about 0.1 mM to 50 mM, 0.1 mM to 20 nM, 1 mM to 20 mM, 1 mM to 10 mM, or 1 mM to 4 mM. Said NSN activity may be defined by a $k_{cat}$ value of said nucleases at about 4° C. of at least 10 s$^{-1}$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

Surprisingly, the herein disclosed non-specific nuclease of *Pseudomonas syringae* having the amino acid sequence of SEQ ID NO:2 and non-specific nucleases having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2 have NSN activity in a solution of about 4° C., and having a pH value of about 5-9, of about 6-8, or of about 7-8. Said NSN activity may be defined by a $k_{cat}$ value of said nucleases at about 4° C. of at least 10 s$^{-1}$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

More surprisingly, the herein disclosed non-specific nuclease of *Pseudomonas syringae* having the amino acid sequence of SEQ ID NO:2 and non-specific nucleases having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2 have NSN activity in a solution of about 4° C., and a cation complexing agent such as EDTA in a range of about 0.1 mM to 50 nM, 0.1 mM to 20 mM, 1 mM to 20 mM, 1 mM to 10 mM, or 1 mM to 4 mM, and having a pH value of about 5-9, of about 6-8, or of about 7-8. Said NSN activity may be defined by a $k_{cat}$ value of said nucleases at about 4° C. of at least 10 s$^{-1}$, 20 s$^-$, 50 s$^-$, 100 s$^{-1}$, 150 s$^-$, 200 s$^-$, 250 s$^{-1}$, 300 s$^{-1}$, or 330 s$^{-1}$. This has great benefit for processes of degrading contaminating nucleic acids and thereby decreasing the viscosity of nucleic acids containing solutions and/or to reduce or prevent clogging of channels, matrices, and pores that are in contact with solutions comprising nucleic acids under herein disclosed conditions in that said nucleases still work.

Therefore, the present invention provides an isolated polypeptide having the above-disclosed characteristics, a kit and composition comprising said isolated polypeptide, methods for degrading nucleic acids using said isolated polypeptide, and uses of said isolated polypeptide for degrading nucleic acids.

BRIEF DESCRIPTION OF THE DRAWINGS

FIG. 1: Result of a BLASTP database search at NCBI Entrez in tabular form for the most identical protein sequences using SEQ ID NO:2 as input sequence. The result is split into three parts (A, B, and C) covering annotated "endonucleases", "phospholipase D family proteins", and "hypothetical proteins" with sequence identities on the amino acid level between 100% and 57.0%. The numbers in parentheses in the column "identity" reflect the numbers of amino acids identical to the 153 amino acid long input sequence, i.e. "151/153" means that 151 of 153 amino acids are identical.

Lac repressor gene; kan: kanamycin resistance gene.

Figure 4:
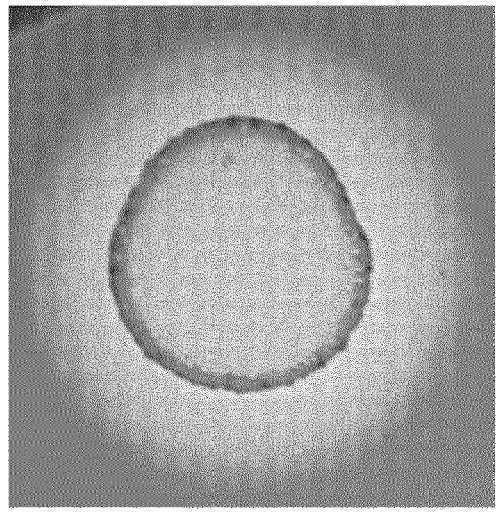

FIG. 4: Picture of an *E. coli* colony expressing recombinant P.vNuc grown on blue agar plates supplemented with toluidine blue ("DNase-indicator plate"). Expression of the gene encoding P.vNuc in *E. coli* resulted in the formation of halos.

Figure 5:
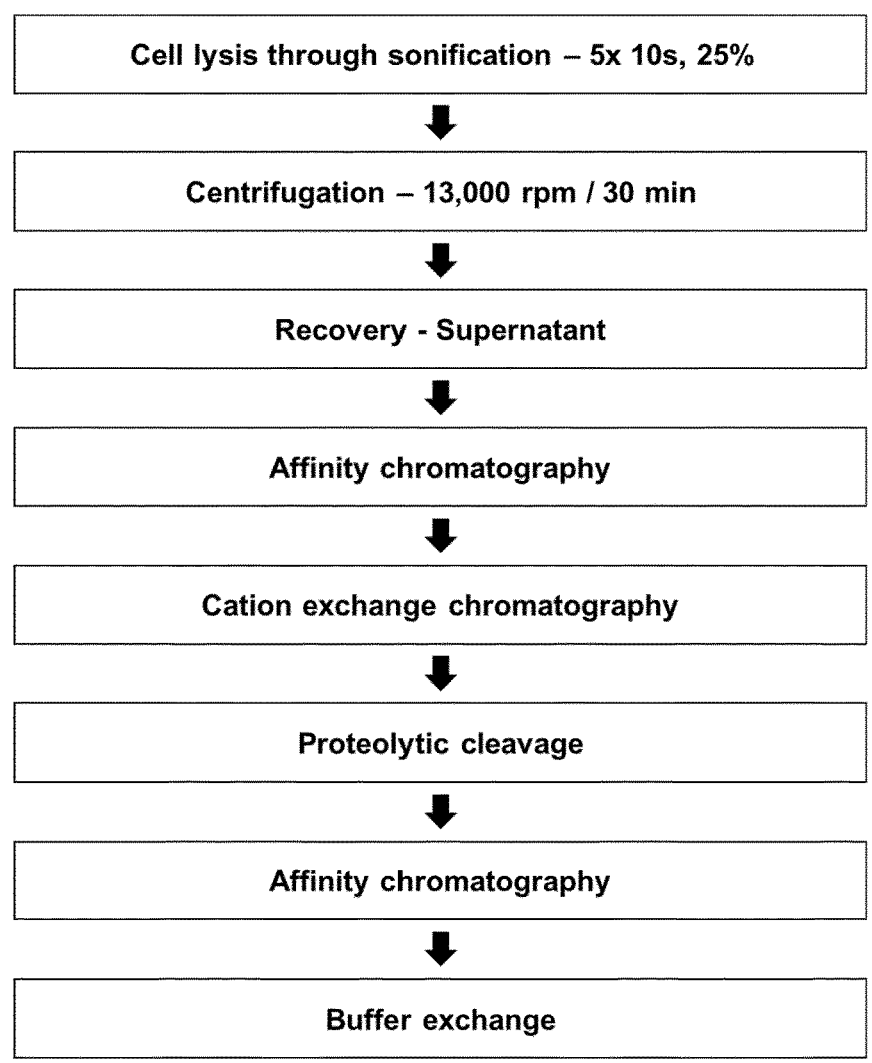

FIG. 5: Flow scheme of the downstream processing strategy. Recombinant P.vNuc and variants thereof were purified from bacterial extracts to homogeneity using this strategy.

Figure 6:
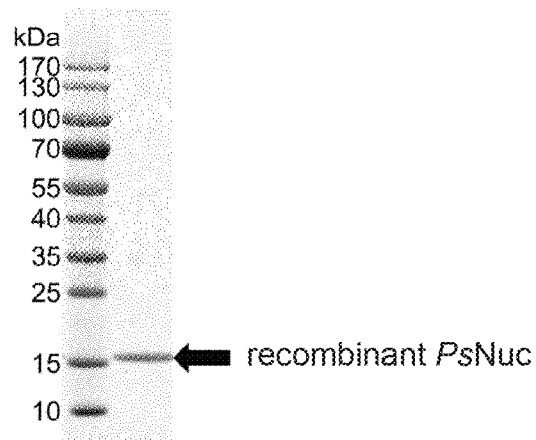

FIG. 6: SDS-PAGE of purified recombinant P.vNuc. 201 of purified protein (about 1 μg) was loaded onto an SDS gel and stained by Coomassie. Marker sizes of the molecular weight marker are indicated aside. kDa: kiloDalton.

Figure 7:
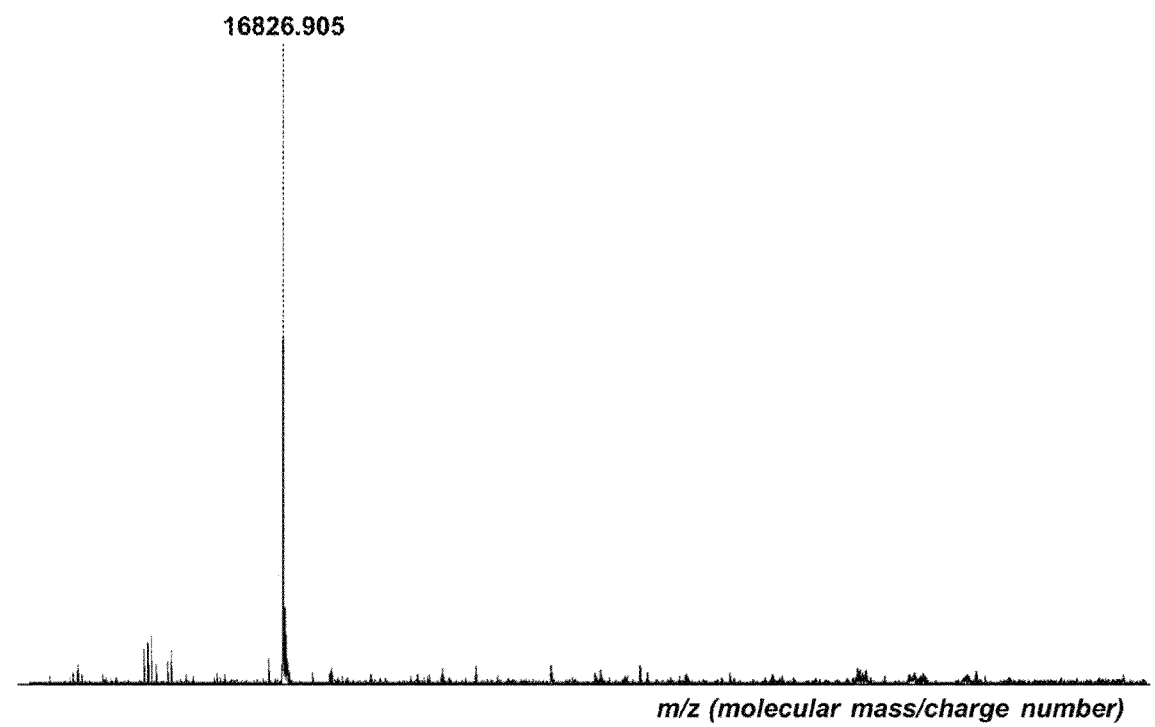

FIG. 7: Determination of the molecular mass of P.vNuc by mass spectrometry. Purified nuclease was analyzed by electrospray ionization mass spectrometry.

Figure 8:
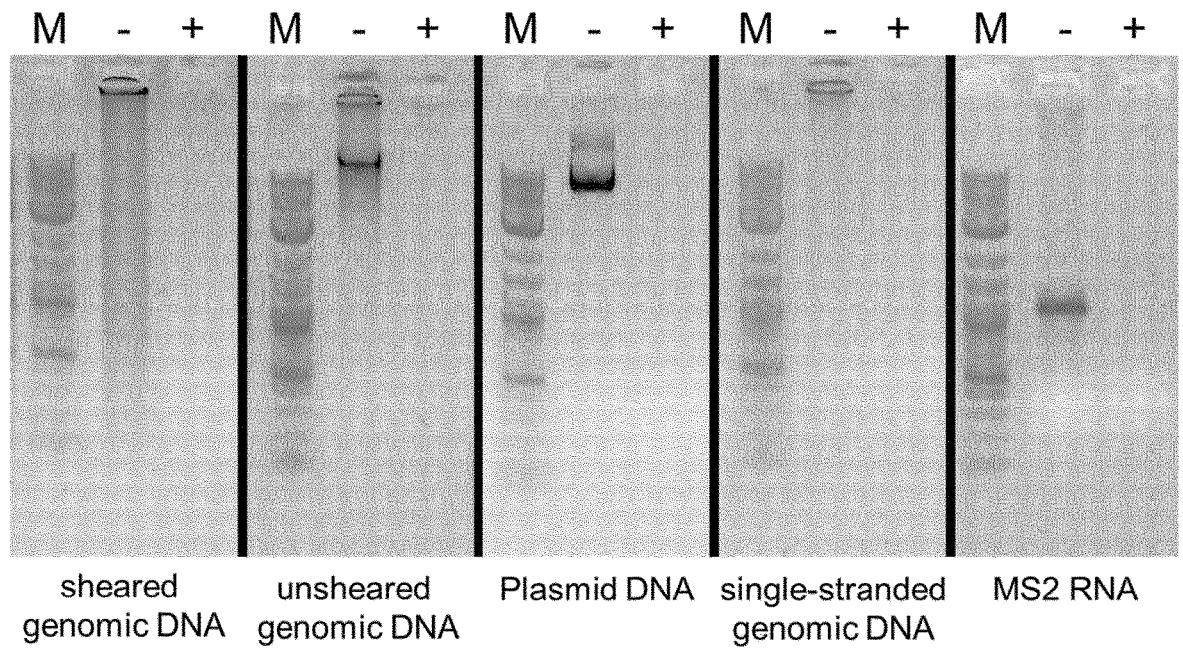

FIG. 8: Agarose gel electrophoresis of different nucleic acids (5 g each) incubated at about 20° C. for 24 hours in the presence ("+") or absence ("−") of 0.5 pg purified Nuc. Nucleic acids were stained by ethidium bromide. M: molecular weight marker covering a range from 100 to 10,000 bps; MS2: bacteriophage MS2.

Figure 9:
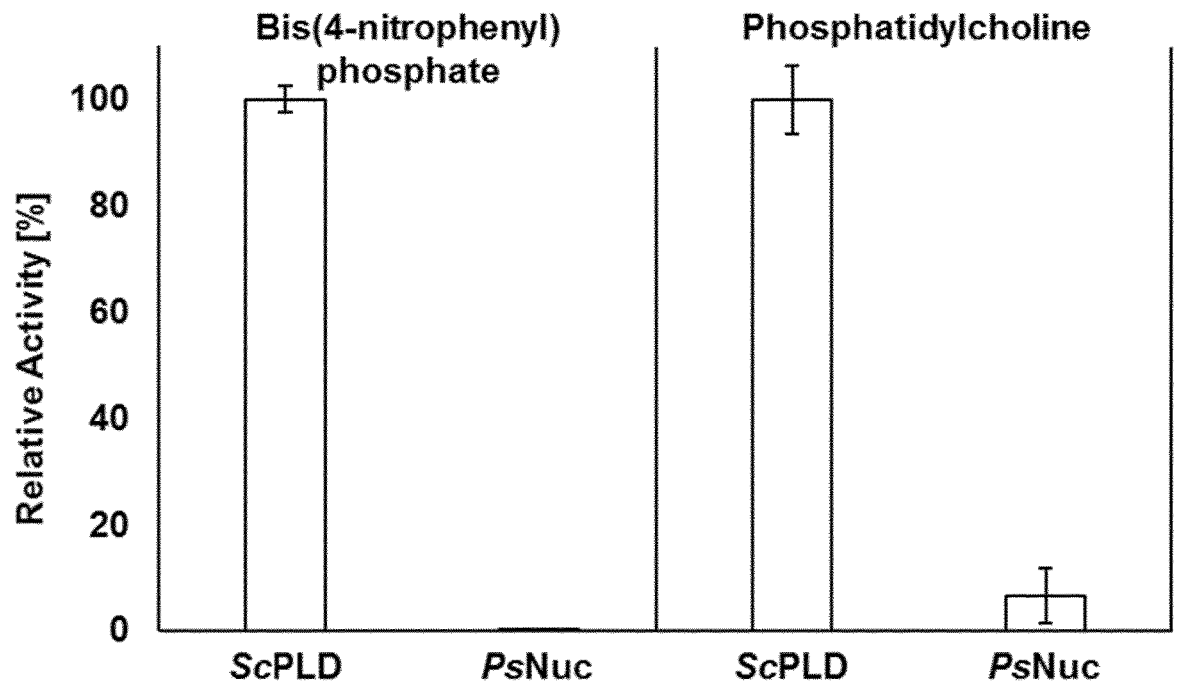

FIG. 9: Relative activity of purified F.vNuc and PLD enzymes towards bis(4-nitrophenyl) phosphate and phosphatidylcholine, respectively. The activity of PLD was set to 100%.

Figure 10:
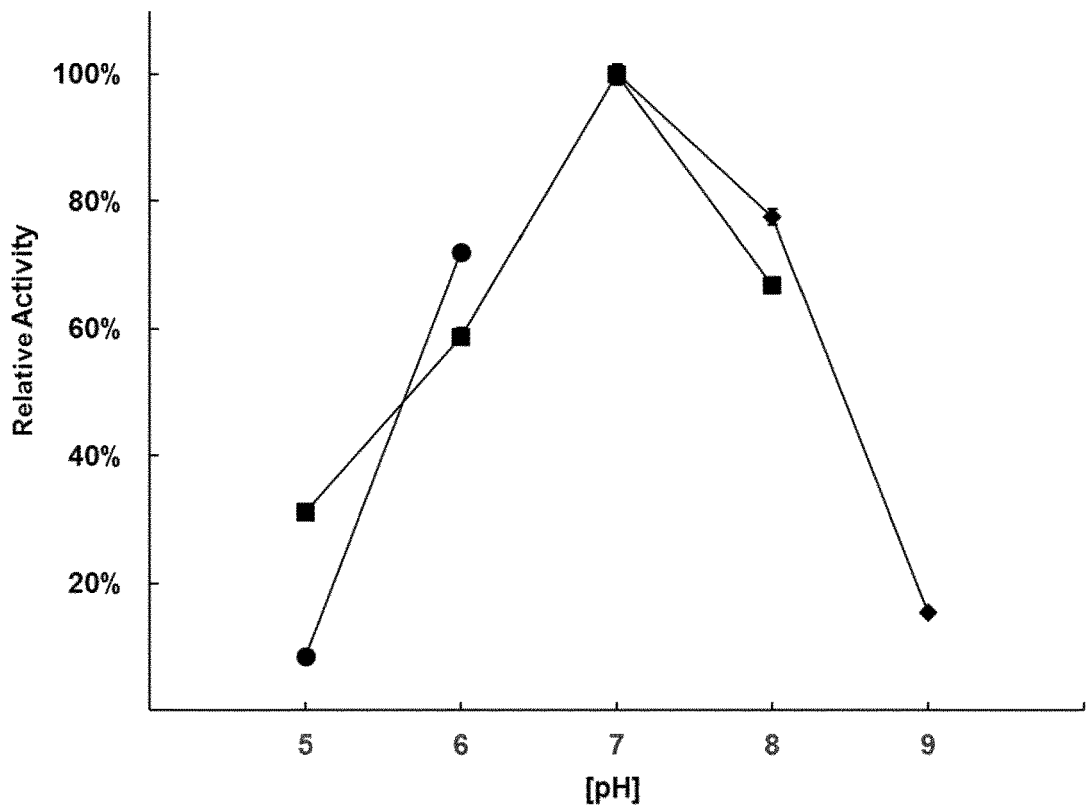

FIG. 10: Relative activity of purified P.vNuc at different pH values. P.vNuc was incubated at about 25° C. for 10 min with sheared dsDNA from salmon sperm using 50 mM sodium acetate buffer (black circles) for pH 4-6, 50 mM sodium phosphate buffer (black squares) for pH 5-7, and 50 mM Tris-HCl buffer (black diamonds) for pH 7-9. Maximum activity was set to 100%.

Figure 11:
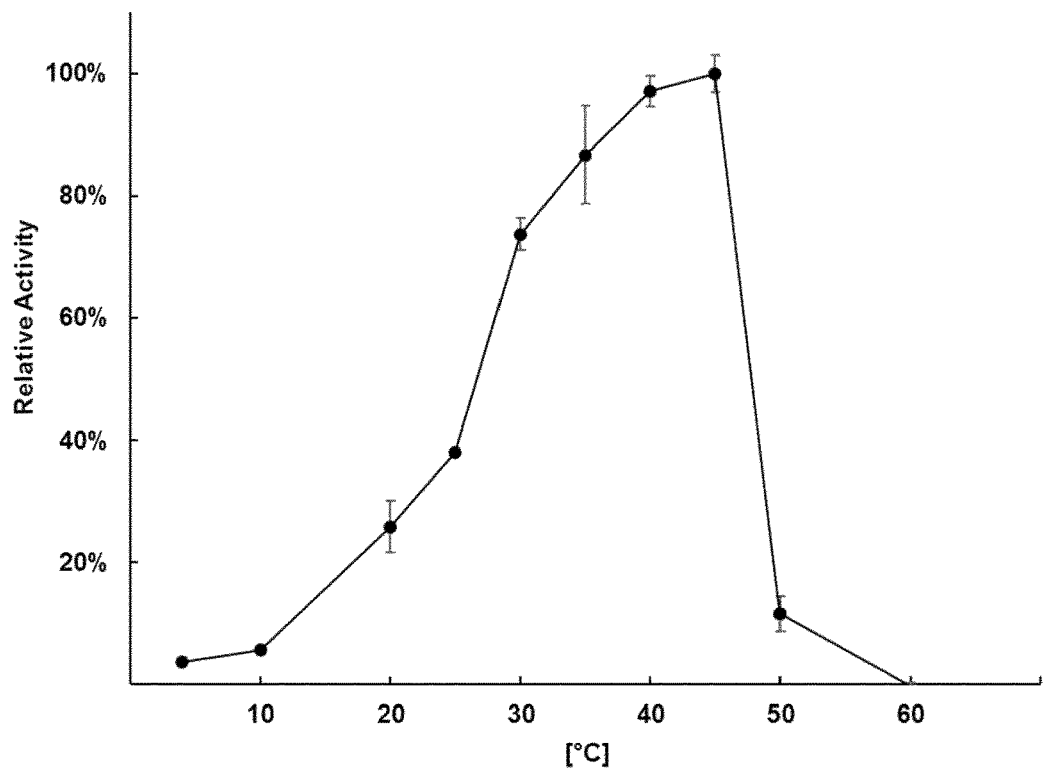

FIG. 11: Relative activity of purified P.vNuc at different temperatures. P.vNuc was incubated at temperatures between about 4° C. and about 60° C. in 50 mM sodium phosphate buffer, pH 7.0 with sheared dsDNA from salmon sperm. Maximum activity was set to 100%.

Figure 12:
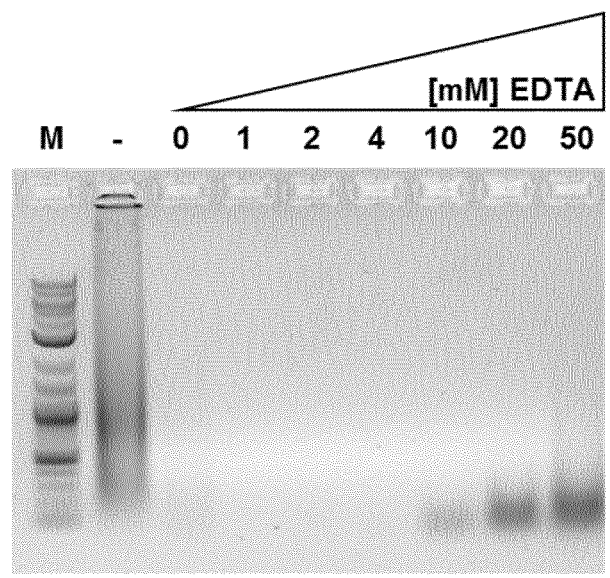

FIG. 12: Agarose gel electrophoresis of sheared dsDNA from salmon sperm. 0.5 pg purified P.vNuc was incubated for 60 min on ice in the presence of EDTA at final concentrations of 0 mM, 1 mM, 2 mM, 4 mM, 10 mM, 20 mM, and 50 mM EDTA, respectively. Afterwards, enzyme samples were supplemented with substrate and incubated for 24 hours at about 20° C. Lane "-": no P.vNuc. M: molecular weight marker covering a range from 100 to 10,000 bps.

Figure 13:
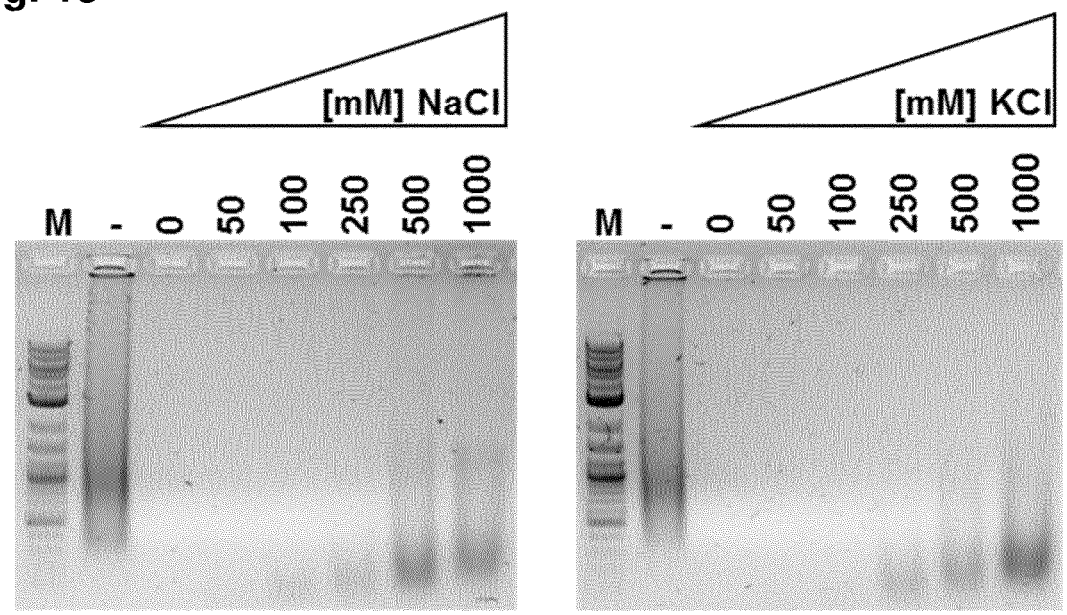

FIG. 13: Agarose gel electrophoresis of sheared dsDNA from salmon sperm. 0.5 pg purified F.vNuc was incubated for 60 min on ice in the presence of 50 mM, 100 mM, 250 mM, 500 mM, and 1000 mM of NaCl and KCl, respectively. Afterwards, enzyme samples were supplemented with substrate and incubated for 24 hours at about 20° C. Lane "-": no F.vNuc. M: molecular weight marker covering a range from 100 to 10,000 bps.

FIG. 14: Agarose gel electrophoresis of sheared dsDNA from salmon sperm. 0.5 pg purified F.vNuc was incubated for 60 min on ice in the presence of 0 mM, 0.1 mM, 0.5 mM, 1 mM, 2 mM, and 10 mM of $MgCl_2$, MnC, CaCE, and COCl2, respectively. Afterwards, enzyme samples were supplemented with substrate and incubated for 24 hours at about 20° C. Lane no P.vNuc. M: molecular weight marker covering a range from 100 to 10,000 bps.

FIG. 15: $k_{cat}$ values of purified P.vNuc and variants thereof: (A) $k_{cat}$ of P.vNuc at about 4° C., about 25° C., and about 35° C., respectively. (B) $k_{cat}$ of purified F.vNuc variants at about 25° C. (C) $k_{cat}$ of F.vNuc at about 25° C. and pH 7.0 in the presence (20 mM or 50 mM) or absence (0 mM) of EDTA. (D) $k_{cat}$ of P.vNuc at about 4° C. and pH 8.0 in the presence (20 mM or 50 mM) or absence (0 mM) of EDTA.

DETAILED DESCRIPTION OF THE INVENTION

In a first aspect the present invention provides an isolated polypeptide for degrading nucleic acids having non-specific nuclease (NSN) activity comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2, wherein said polypeptide has NSN activity in a solution of about 4° C.

Said isolated polypeptide, wherein said solution of about 4° C. comprises a cation complexing agent in a range of about 0.1 mM to 50 mM, 0.1 mM to 20 nM, 1 mM to 20 nM, 1 mM to 10 mM, or 1 mM to 4 mM.

Said isolated polypeptide, wherein said solution of about 4° C. has a pH value of about 5-9, of about 6-8, or of about 7-8.

Said isolated polypeptide, wherein said solution of about 4° C. comprises a cation complexing agent in a range of about 0.1 mM to 50 mM, 0.1 mM to 20 nM, 1 mM to 20 nM, 1 mM to 10 mM, or 1 mM to 4 mM and has a pH value of about 5-9, of about 6-8, or of about 7-8.

Said isolated polypeptide for degrading nucleic acids having non-specific nuclease (NSN) activity comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2, wherein said polypeptide has NSN activity in a solution of about 4° C., wherein said NSN activity in said solution of about 4° C. may be defined by a $k_{cat}$ value of said isolated polypeptide of at least 10 s$^{-1}$, 20 s$^-$, 50 s$^-$, 100 s$^-$, 150 s$^{-1}$, 200 s$^{-1}$, 250 s$^{-1}$, 300 s$^{-1}$, or 330 s$^{-1}$.

Said isolated polypeptide, wherein said solution of about 4° C. comprises a cation complexing agent in a range of about 0.1 mM to 50 mM, 0.1 mM to 20 mM, 1 mM to 20 mM, 1 mM to 10 mM, or 1 mM to 4 mM, wherein said NSN activity in said solution of about 4° C. that comprises a cation complexing agent in said range may be defined by a $k_{cat}$ value of said isolated polypeptide of at least 10 s$^{-1}$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

Said isolated polypeptide, wherein said solution of about 4° C. has a pH value of about 5-9, of about 6-8, or of about 7-8, wherein said NSN activity in said solution of about 4° C. having said pH value may be defined by a $k_{cat}$ value of said isolated polypeptide of at least 10 s$^-$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

Said isolated polypeptide, wherein said solution of about 4° C. comprises a cation complexing agent in a range of about 0.1 mM to 50 mM, 0.1 mM to 20 mM, 1 mM to 20 mM, 1 mM to 10 mM, or 1 mM to 4 mM and has a pH value of about 5-9, of about 6-8, or of about 7-8, wherein said NSN activity in said solution of about 4° C. having said pH value that comprises a cation complexing agent in said range may be defined by a $k_{cat}$ value of said isolated polypeptide of at least 10 s$^{-1}$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

Said isolated polypeptide having a relative NSN activity in a solution of about 4° C. comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2, wherein said relative NSN activity in said solution of about 4° C. is at least 0.5%, 1%, 2%, 3%, 4%, 5%, 6%, 7%, 8%, 9%, or 10% of the activity of said polypeptide at about 25° C.

Said isolated polypeptide, wherein said polypeptide has a relative NSN activity of at least 0.5%, 1%, 2%, 3%, 4%, 5%, 6%, 7%, 8%, 9%, or 10% of the activity of said polypeptide at about 25° C. in a solution that has a temperature of about 4° C. and a pH value of about 5-9, of about 6-8, or of about 7-8.

Said isolated polypeptide, wherein said polypeptide has a relative NSN activity of at least 0.5%, 1%, 2%, 3%, 4%, 5%, 6%, 7%, 8%, 9%, or 10% of the activity of said polypeptide at about 25° C. in a solution that has a temperature of about 4° C. and a concentration of a cation complexing agent in a range of about 0.1 mM to 50 mM, 0.1 mM to 20 nM, 1 mM to 20 nM, 1 mM to 10 mM, or 1 mM to 4 mM.

Said isolated polypeptide, wherein said polypeptide has a relative NSN activity of at least 0.5%, 1%, 2%, 3%, 4%, 5%, 6%, 7%, 8%, 9%, or 10% of the activity of said polypeptide at about 25° C. in a solution that has a temperature of about 4° C., a concentration of a cation complexing agent in a range of about 0.1 mM to 50 mM, 0.1 mM to 20 mM, 1 mM to 20 mM, 1 mM to 10 mM, or 1 mM to 4 mM, and a pH value of about 5-9, of about 6-8, or of about 7-8.

In one embodiment said isolated polypeptide comprises or consists of SEQ ID NO:3 or SEQ ID NO:6. Surprisingly, these polypeptides comprising single amino acid substitutions have an even higher activity than SEQ ID NO: 2 (FIG. 15B).

Said isolated polypeptide may be for degrading nucleic acids, preferentially for degrading nucleic acids that are contained in said solution(s).

Said nucleic acids may be selected from the group consisting of single-stranded DNA, linear double-stranded DNA, circular double-stranded DNA, single-stranded RNA, linear double-stranded RNA, and circular double-stranded RNA.

Said cation complexing agent may be a chelating agent selected from the group consisting of EDTA (ethylenediaminetetraacetic acid), EGTA (ethylene glycol-bis(2-aminoethylether)-N,N,N',N'-tetraacetic acid), DOTA (1,4,7,10-tetraazacyclododecane-1,4,7,10-tetraacetic acid), DTPA (diethylenetriaminepentaacetic acid), MGDA (methylglycine N,N-diacetic acid), GLDA (glutamate diacetate), NTA (nitrilotriacetic acid), IDS (iminodisuccinate), HEEDTA (N-(2-hydroxyethyl)ethylenediamine-N,N',N'-triacetic acid), STPP (sodium tripolyphosphate), TTHA (triethylenetetramine-N,N,N',N'',N''',N'''-hexaacetic acid), phosphonates, DFOA (desferrioxamine), and DMSA (2,3-di-mercaptosuccinic acid), penicillamine, dimercaprol, and zeolites.

Said cation complexing agent in a range of about 0.1 mM to 50 mM, 0.1 mM to 20 mM, 1 mM to 20 mM, 1 mM to 10 mM, or 1 mM to 4 mM may be selected from DOTA, EGTA und EDTA. Preferentially, said cation complexing agent may be EDTA.

Said solution(s) may be a non-specific nuclease compatible buffer.

Said solution(s) may comprise salts in a range of about 0 mM to 1,000 mM, 0 mM to 500 mM, 0 mM to 250 mM, 50 mM to 250 mM, or 100 mM to 250 mM. Said salts may be selected from sodium chloride, potassium chloride, sodium phosphate, and potassium phosphate.

In a further aspect the present invention provides a composition comprising
  i) an (isolated) polypeptide for degrading nucleic acids having non-specific nuclease (NSN) activity comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2, wherein said polypeptide has NSN activity in a solution of about 4° C., and
  ii) a cation complexing agent.

Surprisingly, said polypeptide has NSN activity in a solution of about 4° C. in the presence of a cation complexing agent such as EDTA because said polypeptide is a metal ion independent nuclease.

Said NSN activity of said polypeptide in said solution of about 4° C. may be defined by the $k_{cat}$ values already described above.

Said composition, wherein said polypeptide and said cation complexing agent are in a solution of about 4° C., and wherein said cation complexing agent is in a range of about 0.1 mM to 50 mM, 0.1 mM to 20 mM, 1 mM to 20 mM, 1 mM to 10 mM, or 1 mM to 4 mM.

Said composition, wherein said solution of about 4° C. comprises a cation complexing agent in a range of about 0.1 mM to 50 mM, 0.1 mM to 20 mM, 1 mM to 20 mM, 1 mM to 10 mM, or 1 mM to 4 mM and has a pH value of about 5-9, of about 6-8, or of about 7-8.

In one embodiment said composition comprises said polypeptide that comprises or consists of SEQ ID NO:3 or SEQ ID NO:6.

Said composition, wherein said polypeptide may be for degrading nucleic acids, preferentially for degrading nucleic acids that are contained in said solution(s).

Said nucleic acids may be selected from the group consisting of single-stranded DNA, linear double-stranded DNA, circular double-stranded DNA, single-stranded RNA, linear double-stranded RNA, and circular double-stranded RNA.

Said composition, wherein said cation complexing agent may be a chelating agent selected from the group consisting of EDTA (ethylenediaminetetraacetic acid), EGTA (ethylene glycol-bis(2-aminoethylether)-N,N,N',N'-tetraacetic acid), DOTA (1,4,7,10-tetraazacyclododecane-1,4,7,10-tetraacetic acid), DTPA (diethylenetriaminepentaacetic acid), MGDA (methylglycine N,N-diacetic.acid), GLDA (glutamate diacetate), NTA (nitrilotriacetic acid), IDS (iminodisuccinate), HEEDTA (N-(2-hydroxyethyl)ethylenediamine-N,N',N'-triacetic acid), STPP (sodium tripolyphosphate), TTHA (triethylenetetramine-N,N,N',N'',N''',N'''-hexaacetic acid), phosphonates, DFOA (desferrioxamine), and DMSA (2,3-di-mercaptosuccinic acid), penicillamine, dimercaprol, and zeolites.

Said cation complexing agent in a range of about 0.1 mM to 50 mM, 0.1 mM to 20 mM, 1 mM to 20 mM, 1 mM to 10 mM, or 1 mM to 4 mM may be selected from DOTA, EGTA und EDTA. Preferentially, said cation complexing agent may be EDTA.

Said solution(s) may be a non-specific nuclease compatible buffer. Said solution(s) may comprise salts in a range of about 0 mM to 1,000 mM, 0 mM to 500 mM, 0 mM to 250 mM, 50 mM to 250 mM, or 100 mM to 250 mM. Said salts may be selected from sodium chloride, potassium chloride, sodium phosphate, and potassium phosphate.

In a further aspect the present invention provides a composition comprising
  i) an (isolated) polypeptide for degrading nucleic acids having non-specific nuclease (NSN) activity comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to SEQ ID NO:2, wherein said polypeptide has NSN activity in a solution of about 4° C., and
  ii) a metal ion free solution.

Said composition, wherein said composition and said cation complexing agent are in said metal ion free solution of about 4° C., and wherein said cation complexing agent is in a range of about 0.1 mM to 50 mM, 0.1 mM to 20 mM, 1 mM to 20 mM, 1 mM to 10 mM, or 1 mM to 4 mM. Ina further aspect the present invention provides a kit comprising an isolated polypeptide or the compositions as disclosed herein.

Said isolated polypeptide or said compositions of said kit may be for degrading nucleic acids, preferentially for degrading nucleic acids that are contained in solution(s).

Said kit may further comprise materials and/or instructions for degrading nucleic acids.

Said kit may additionally comprise a storage buffer for nucleases or a nuclease compatible buffer, preferentially for non-specific nucleases.

In another aspect the present invention provides a method for degrading nucleic acids comprising the step of contacting an isolated polypeptide as disclosed herein with nucleic acids in a solution.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 nM, 1 mM to 10 mM, or 1 mM to 4 mM.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and a pH value of about 5-9, of about 6-8, or of about 7-8. Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C., wherein said NSN activity in said solution may be defined by a $k_{cat}$ value of said isolated polypeptide of at least 10 s$^-$, 20 s$^-$, 50 s$^-$, 100 s$^{-1}$, 150 s$^{-1}$, 200 s$^-$, 250 s$^{-1}$, 300 s$^{-1}$, or 330 s$^{-1}$.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 mM, 1 mM to 10 mM, or 1 mM to 4 mM, wherein said NSN activity in said solution may be defined by a $k_{cat}$ value of said isolated polypeptide of at least 10 s$^-$, 20 s$^-$, 50 s$^{-1}$, 100 s$^{-1}$, 150 s$^-$, 200 s$^-$, 250 s$^{-1}$, 300 s$^{-1}$, or 330 s$^{-1}$. Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and a pH value of about 5-9, of about 6-8, or of about 7-8, wherein said NSN activity in said solution may be defined by a $k_{cat}$ value of said isolated polypeptide of at least 10 s$^{-1}$, 20 s$^{-1}$, 50 s$^{-1}$, 100 s$^{-1}$, 150 s$^{-1}$, 200 s$^{-1}$, 250 s$^{-1}$, 300 s$^{-1}$, or 330 s$^{-1}$.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 nM, 1 mM to 10 nM, or 1 mM to 4 mM and a pH value of about 5-9, of about 6-8, or of about 7-8, wherein said NSN activity in said solution may be defined by a $k_{cat}$ value of said isolated polypeptide of at least 10 s$^{-1}$, 20 s$^-$, 50 s$^{-1}$, 100 s$^{-1}$, 150 s$^{-1}$, 200 s$^{-1}$, 250 s$^{-1}$, 300 s$^{-1}$, or 330 s$^{-1}$.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C., wherein said relative NSN activity in said solution is at least 0.5%, 1%, 2%, 3%, 4%, 5%, 6%, 7%, 8%, 9%, or 10% of the activity of said polypeptide at about 25° C.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and a pH value of about 5-9, of about 6-8, or of about 7-8, wherein said relative NSN activity in said solution is at least 0.5%, 1%, 2%, 3%, 4%, 5%, 6%, 7%, 8%, 9%, or 10% of the activity of said polypeptide at about 25° C.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 mM, 1 mM to 10 mM, or 1 mM to 4 mM, wherein said relative NSN activity in said solution is at least 0.5%, 1%, 2%, 3%, 4%, 5%, 6%, 7%, 8%, 9%, or 10% of the activity of said polypeptide at about 25° C.

Said method, wherein said isolated polypeptide is contacted with said nucleic acids in a solution that has a temperature of about 0° C. to 10° C., of about 2° C. to 10° C., of about 4° C. to 10° C., of about 4° C. to 6° C., or of about 4° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8, wherein said relative NSN activity in said solution is at least 0.5%, 1%, 2%, 3%, 4%, 5%, 6%, 7%, 8%, 9%, or 10% of the activity of said polypeptide at about 25° C.

Said method, wherein said isolated polypeptide is contacted with said nucleic acids in a solution that has a temperature of about 10° C. to about 25° C.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 mM, 1 mM to 20 mM, 1 mM to 10 mM, or 1 mM to 4 mM.

Said method, wherein said isolated polypeptide is contacted with said nucleic acids in a solution that has a temperature of about 10° C. to about 25° C. and a pH value of about 5-9, of about 6-8, or of about 7-8.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8. Said method, wherein said isolated polypeptide is contacted with said nucleic acids in a solution that has a temperature of about 10° C. to about 25° C., wherein said NSN activity in said solution may be defined by a $k_{cat}$ value of said isolated polypeptide of at least 50 s$^-$, 100 s$^-$, 250 s$^{-1}$, 500 s$^{-1}$, 750 s$^-$, 1,000 s$^{-1}$, 1,500 s$^{-1}$, or 1,700 s$^{-1}$ at about 25° C.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 mM, 1 mM to 20 mM, 1 mM to 10 mM, or 1 mM to 4 mM, wherein said NSN activity in said solution may be defined by a $k_{cat}$ value of said isolated polypeptide of at least 50 s$^-$, 100 s$^-$, 250 s$^-$, 500 s$^-$, 750 s$^-$, 1,000 s$^{-1}$, 1,500 s$^{-1}$, or 1,700 s$^{-1}$ at about 25° C.

Said method, wherein said isolated polypeptide is contacted with said nucleic acids in a solution that has a temperature of about 10° C. to about 25° C. and a pH value of about 5-9, of about 6-8, or of about 7-8, wherein said NSN activity in said solution may be defined by a $k_{cat}$ value of said isolated polypeptide of at least 50 s$^{-1}$, 100 s$^-$, 250 s$^-$, 500 s$^-$, 750 s$^-$, 1,000 s$^-$, 1,500 s$^{-1}$, or 1,700 s$^{-1}$ at about 25° C.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8, wherein said NSN activity in said solution may be defined by a $k_{cat}$ value of said isolated polypeptide of at least 50 s$^{-1}$, 100 s$^-$, 250 s$^{-1}$, 500 s$^{-1}$, 750 s$^{-1}$, 1,000 s$^{-1}$, 1,500 s$^{-1}$, or 1,700 s$^{-1}$ at about 25° C.

Said method, wherein said isolated polypeptide is contacted with said nucleic acids in a solution that has a temperature of about 10° C. to about 25° C., wherein said relative NSN activity in said solution is at least 3%, 5%, 10%, 15%, or 20% of the activity of said polypeptide at about 25° C. Said method, wherein said isolated polypeptide is contacted with said nucleic acids in a solution that has a temperature of about 10° C. to about 25° C. and a pH value of about 5-9, of about 6-8, or of about 7-8, wherein said relative NSN activity in said solution is at least 3%, 5%, 10%, 15%, or 20% of the activity of said polypeptide at about 25° C.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 nM, 1 mM to 20 mM, 1 mM to 10 mM, or 1 mM to 4 mM, wherein said relative NSN activity in said solution is at least 3%, 5%, 10%, 15%, or 20% of the activity of said polypeptide at about 25° C.

Said method, wherein said isolated polypeptide is contacted with said nucleic acids in a solution that has a temperature of about 10° C. to about 25° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8, wherein said relative NSN activity in said solution is at least 3%, 5%, 10%, 15%, or 20% of the activity of said polypeptide at about 25° C.

Said method, wherein said isolated polypeptide is contacted with said nucleic acids in a solution that has a temperature of about 25° C. to about 45° C.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM.

Said method, wherein said isolated polypeptide is contacted with said nucleic acids in a solution that has a temperature of about 25° C. to about 45° C. and a pH value of about 5-9, of about 6-8, or of about 7-8.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8. Said method, wherein said isolated polypeptide is contacted with said nucleic acids in a solution that has a temperature of about 25° C. to about 45° C., wherein said NSN activity in said solution may be defined by a $k_{cat}$ value of said isolated polypeptide of at least 50 s$^{-1}$, 100 s$^-$, 250 s$^-$, 500 s$^-$, 750 s$^-$, 1,000 s$^-$, 1,500 s$^{-1}$, or 1,700 s$^{-1}$ at about 25° C.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM, wherein said NSN activity in said solution may be defined by a $k_{cat}$ value of said isolated polypeptide of at least 50 s$^-$, 100 s$^-$, 250 s$^-$, 500 s$^-$, 750 s$^-$, 1,000 s$^-$, 1,500 s$^{-1}$, or 1,700 s$^{-1}$ at about 25° C.

Said method, wherein said isolated polypeptide is contacted with said nucleic acids in a solution that has a temperature of about 25° C. to about 45° C. and a pH value of about 5-9, of about 6-8, or of about 7-8, wherein said NSN activity in said solution may be defined by a $k_{cat}$ value of said isolated polypeptide of at least 50 s$^{-1}$, 100 s$^{-1}$, 250 s$^{-1}$, 500 s$^{-1}$, 750 s$^{-1}$, 1,000 s$^{-1}$, 1,500 s$^{-1}$, or 1,700 s$^{-1}$ at about 25° C.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8, wherein said NSN activity in said solution may be defined by a $k_{cat}$ value of said isolated polypeptide of at least 50 s$^{-1}$, 100 s$^-$, 250 s$^-$, 500 s$^-$, 750 s$^-$, 1,000 s$^-$, 1,500 s$^{-1}$, or 1,700 s$^{-1}$ at about 25° C.

Said method, wherein said isolated polypeptide is contacted with said nucleic acids in a solution that has a temperature of about 25° C. to about 45° C., wherein said relative NSN activity in said solution is at least 25%, 50%, 75%, or 100% of the activity of said polypeptide at about 25° C. Said method, wherein said isolated polypeptide is contacted with said nucleic acids in a solution that has a temperature of about 25° C. to about 45° C. and a pH value of about 5-9, of about 6-8, or of about 7-8, wherein said relative NSN activity in said solution is at least 25%, 50%, 75%, or 100% of the activity of said polypeptide at about 25° C.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM, wherein said relative NSN activity in said solution is at least 25%, 50%, 75%, or 100% of the activity of said polypeptide at about 25° C.

Said method, wherein said isolated polypeptide is contacted with said nucleic acids in a solution that has a temperature of about 25° C. to about 45° C. and has a concentration of a cation complexing agent in a range of about 0.1 mM to 50 mM, 0.1 mM to 20 mM, 1 mM to 20 mM, 1 mM to 10 mM, or 1 mM to 4 mM and a pH value of about 5-9, of about 6-8, or of about 7-8, wherein said relative NSN activity in said solution is at least 25%, 50%, 75%, or 100% of the activity of said polypeptide at about 25° C.

Said method, wherein said nucleic acids are from damaged or lysed cells within a cell sample comprising damaged or lysed cells and viable cells, thereby preventing an increase of viscosity of the solution comprising said cell sample and/or clogging of channels, matrices, and pores in cell culturing, cell sorting and cell separation devices, for example microfluidic channels and filter pores.

Said method, wherein said step of contacting said nucleic acids with said isolated polypeptide is performed in a cell culture device, thereby reducing the viscosity of said solution in said cell culture device.

Said method, wherein said step of contacting said nucleic acids with said isolated polypeptide is performed in a cell sorting device, thereby reducing the viscosity of said solution in said cell sorting device.

Said method, wherein said step of contacting said nucleic acids with said isolated polypeptide is performed in a magnetic cell separation device, thereby reducing the viscosity of said solution in said magnetic cell separation device.

Said method, wherein said step of contacting said nucleic acids with said isolated polypeptide is performed in a microfluidic channel, thereby reducing the viscosity of said solution in said microfluidic channel.

In a further aspect the present invention provides a composition comprising an isolated polypeptide as disclosed herein and a nuclease compatible buffer, preferentially for non specific nucleases.

In another aspect the present invention provides the use of an isolated polypeptide as disclosed herein for degrading nucleic acids.

Said use, wherein said cell sample is in a cell culture device.

Said use, wherein said cell sample is in the channels of a cell sorting device.

Said use, wherein said cell sample is in the channels of a magnetic cell separation device.

Said use, wherein said cell sample is in micro fluidic channels.

In a further aspect the present invention provides an isolated nucleic acid encoding an isolated polypeptide as disclosed herein.

In another aspect the present invention provides a vector comprising a nucleic acid encoding an isolated polypeptide as disclosed herein.

In one aspect the present invention provides a (isolated) host cell comprising a vector comprising a nucleic acid encoding an isolated polypeptide as disclosed herein.

In another aspect the invention provides a host cell expressing an isolated polypeptide as disclosed herein.

All definitions, characteristics and embodiments defined herein with regard to the isolated polypeptide of the invention also apply mutatis mutandis in the context of the other aspects of the invention: the kit, the compositions, the methods, the uses of the isolated polypeptide, the nucleic acid and vector encoding the isolated polypeptide, and the host cell containing and/or expressing the isolated polypeptide of the invention as disclosed herein.

Embodiments

In one embodiment of the invention a polypeptide having NSN activity as disclosed herein is used to degrade and thereby to remove nucleic acids from solutions. These solutions may contain proteins, cells, tissues, or other biological materials. In one example, the polypeptide having NSN activity is used to degrade nucleic acids such as DNA and/or RNA present in crude cell extracts that are prepared to isolate and purify a recombinant or native protein from a host cell. Because nucleic acids are contaminating the protein-of-interest, it is of interest to remove the nucleic acids as far as possible. Cells comprising the protein-of-interest are lysed using a buffer (for example based on a phosphate buffer pH 7-8) containing the polypeptide having NSN activity. The buffer may contain cation-complexing agents. This solution is incubated at a defined temperature for a defined time (for example, 10 min at about 37° C. or 2 hours at about 4° C.). During incubation, nucleic acids are degraded. Afterwards the protein is isolated and purified using technique state-in-the art. In another example, the polypeptide having NSN activity is used to degrade nucleic acids in cell solutions such as an adherent or non-adherent cell culture solution. The cells are incubated in a buffered solution (for example based on a phosphate buffer with a pH of about 7-8 plus about 1-4 mM EDTA) at temperatures required for cell survival (for example in the range from about 0° C. to about 10° C.). The polypeptide having NSN activity is added once or frequently to the cell solution to degrade and thereby to remove nucleic acids that are released from dying/dead cells. As a result, contaminating nucleic acids are removed, and it is prevented that the viscosity of the solution increases due to increasing concentrations of nucleic acids in the solution.

In another embodiment of the invention a polypeptide as disclosed herein is used to degrade and thereby to remove nucleic acids from solutions comprising cells (pro- and/or eukaryotic cells) that are handled in and/or sorted by cell sorting devices, in particular by cell sorting devices having microfluidic channels. In general, cell sorting devices are composed of channels with specific dimensions of a few micrometers to sort eukaryotic and prokaryotic cells. Cells or other particles can be moved in a fluid stream to pass narrow micro-channels under pressure. Such cell/particle sorters are often based on flow cytometry. Due to the narrow micro-duct and the increased pressure within the channels, cells become damaged or even lysed and proteins, membranes and nucleic acids such as DNA or aggregates thereof are diffusing out of the cells. The cells and other particles may adhere to surfaces or exhibit a strong tendency to coagulate, which can lead to an unwanted change in the flow pattern and even to irreversible clogging of narrow passageways, thereby dramatically reducing the operation time. Clogging caused by an increased viscosity based on the presence of nucleic acids in the sample might already occur when only little amounts of free nucleic acids were released to the liquid solution. Due to the increased viscosity of the liquid solution, nucleic acids are the main reason for clogging effects in microfluidic devices separating cells. The medium or buffered solution of a cell culture favors certain conditions for the cells to survive and proliferate. Relevant conditions include growth temperature, pH, ionic strength of the buffer, and prevention of cation-induced cell aggregation by cation-complexing agents (for example, EDTA). Such conditions also set limits to the activity of the applied polypeptide having NSN activity. Moreover, this enzyme has to withstand further substances that are released by lysed cells and in the applied buffer systems, such as phosphate-based buffers, salts and protease inhibitors. In one example, a flow cytometry based cell sorting device is used, and a polypeptide having NSN activity as disclosed herein is added to the medium or solution containing the cells or particles to be sorted. Due to its presence, a polypeptide having NSN activity continuously degrades contaminating nucleic acids that are derived from, for example, lysed cells. Because the polypeptide having NSN activity is active even at about 4° C., the solution comprising cells may have about 4° C. The viscosity of the medium or solution is thereby reduced, and clogging is reduced, prevented, or eliminated. Cell sorting may be conducted in the presence of a cation-complexing agent such as EDTA (for example, in the range of about 0.1-50 mM), because the polypeptide as disclosed herein has NSN activity under these conditions.

In another example, a microelectromechanical system (MEMS) based cell sorting system such as the MACSQuant® Tyto® (Miltenyi Biotec GmbH, Germany, order no. 130-103-931) is used for cell sorting, and a polypeptide having NSN activity as disclosed herein is used to degrade contaminating nucleic acids in the microfluidic channels. The MACSQuant® Tyto® is a benchtop cell sorter equipped with 3 lasers, which allows for 10-parameter cell sorting. The cells are sorted in EDTA containing buffers or solutions. The addition of the polypeptide having NSN activity as disclosed herein to said buffer or solution reduces, prevents or eliminates clogging in the microfluidic channels as it degrades contaminating nucleic acids that may be present in the channels due to, for example, lysed cells. Due to its presence, a polypeptide having NSN activity continuously degrades contaminating nucleic acids. Because the polypeptide having NSN activity is active even at about 4° C., the solution comprising cells may have about 4° C. The viscosity of the medium or solution is thereby reduced, and clogging is reduced, prevented, or eliminated. Cell sorting may be conducted preferably in the range of 0° C.-10° C., pH 7-8, and in the presence of a cation-complexing agent such as EDTA (for example, in the range of about 0.1-50 mM), because the polypeptide as disclosed herein has NSN activity under these conditions.

In one embodiment of the invention a polypeptide having NSN activity as disclosed herein is used to degrade and thereby to remove contaminating nucleic acids that are, for example, released from lysed cells during magnetic cell separation and that are able to clog the magnetic column matrix used in said cell separation procedure. The process of magnetic cells sorting such as MACS® (Miltenyi Biotec, Germany) is well known-in-the art. For example, a solution or a buffer comprising target and non-target cells in incubated with magnetic particles linked to antibodies or antibody fragments specifically binding to target cells. The mixture is applied to an appropriate magnetic column that is placed in a magnetic field. Magnetically labeled target cells are thereby retained in the column, while non-target cells are in the flow-through fraction. Target cells are isolated by eluting outside of the magnet. A polypeptide having NSN activity may be added to the solution or buffer comprising cells before and/or after the magnetic particles are added. Alternatively, a polypeptide having NSN activity may be immobilized in the magnetic column through which the cells are passed. Due to its presence, a polypeptide having NSN activity continuously degrades contaminating nucleic acids in the matrix of the column. Because the polypeptide having NSN activity is active even at about 4° C., the solution comprising cells may have about 4° C. The viscosity of the medium or solution is thereby reduced, and clogging is reduced, prevented, or eliminated. Magnetic cell separation may be conducted and in the presence of a cation-complexing agent such as EDTA (for example, in the range of about 0.1-50 mM), because the polypeptide as disclosed herein has NSN activity under these conditions.

In another embodiment of the invention a polypeptide having NSN activity as disclosed herein is used to degrade and thereby to remove contaminating nucleic acids that are, for example, released from dying cells during cultivation of cells in a cell culturing device comprising filter pores. Filters having said filter pores may be used, for example, to separate two compartments but to enable the exchange of liquids or certain components of liquids between the two compartments. Said filters may also be used for the supply of oxygen and/or $CO_2$ into a cell culture while maintaining sterility of the culture. One example of said device comprises the CliniMACS Prodigy® (Miltenyi Biotec GmbH, Germany, order no 200-075-301). The device is able to perform automated washing, fractionation and cultivation of cells. The cells are cultured and washed in a cell culture chamber that contains filter pores. A polypeptide having NSN activity may be added to the solution or buffer comprising the cells. Alternatively, a polypeptide having NSN activity may be immobilized on the surface of the cell culture chamber so that the polypeptide comes in contact with the cell solution. Due to its presence, a polypeptide having NSN activity continuously degrades contaminating nucleic acids. Clogging of the filter pores is reduced, prevented, or eliminated. Cell culturing and washing may be conducted in the presence of a cation-complexing agent such as EDTA (for example, in the range of about 0.1-50 mM), because the polypeptide as disclosed herein has NSN activity under these conditions. In one embodiment of the invention a polypeptide having NSN activity as disclosed herein is immobilized on the surface of support materials. Such surfaces might be plain or spherical. Said surfaces may be composed of organic or inorganic, natural or synthetic polymers that include but are not limited to carboxymethyl-cellulose, starch, collagen, modified sepharose, ion exchange resins, active charcoal, silica-based carriers, clay, aluminum oxide, titanium, diatomaceous earth, hydroxyapatite, ceramic, Celite®, agarose, acrylic resins and synthetic polymers. Said surfaces may be also of natural origin, for example the membrane of a eukaryotic cell or a bacterial cell wall. Said polypeptide having NSN activity may be immobilized to said surfaces covalently or non-covalently including physical adsorption, entrapment, covalent attachment or cross-linking of proteins and carriers or the formation of membrane-associated complexes with biological cells. Such carriers include but are not limited to beads, magnetic particles, nanofibers, nanotubes, nanocomposites and biological cells. Said polypeptides might be genetically modified or even modular fusion proteins that allow the interaction with a respective surface. Such immobilized proteins may exhibit increased catalytic activities and/or enhanced stabilities and might simplify downstream processes due to recycling approaches.

In one embodiment of the invention a polypeptide having NSN activity as disclosed herein is used in clinical applications. In one example, human cells in a buffer or solution are incubated with said polypeptide to degrade and thereby to remove contaminating nucleic acids that are, for example, released from dying cells. Said polypeptide may be added to the solution or buffer, or it may be immobilized covalently or non-covalently to a surface. Afterwards, said cells may be washed to remove said polypeptide. Said cells may be administered to a patient, for example during cellular therapy.

In another embodiment of the present invention a polypeptide having NSN activity as disclosed herein may be expressed by recombinant techniques in cells (for example, bacterial, yeast, insect or mammalian cells) or by cell-free expression systems. Said polypeptides maybe isolated by, for example, chromatographic methods. Said polypeptide may comprises mutations (amino acid substitutions), deletions, additions (including tags, linkers, and protein fusions), and modifications (including chemical conjugations and incorporation of isotopes). Said polypeptide may be part of fusion protein, wherein it may be fused to, for example, a DNA-binding domain, a signal peptide, an affinity tag, an intein cleavage site, and/or a protease cleavage site. The generation of fusion proteins by using molecular biology approaches are standard methods that are well known to a person skilled in the art. DNA-binding domains might increase the NSN activity of said polypeptide by the increased formation of substrate-enzyme complexes and/or might direct the NSN activity to specific recognition sites in the nucleic acid. Fusion of said polypeptide to a signal peptide sequence may be used to direct said polypeptide to a specific compartment, to an organelle or to export it out of the cell into the medium or into the periplasm. Examples of such signal peptides comprise but are not limited to PhoA or PelB. Affinity tags that may be separated from the said polypeptide by an intein or a protease cleavage site are also well known to a person skilled in the art. Examples for such affinity tags include but are not limited to HIS, GST, MBP, or SUMO. Examples for proteases that are able to cleave said protease cleavage site comprise but are not limited to TEV protease, factor Xa, thrombin, and deubiquitinating enzymes.

In another embodiment of the present invention a polypeptide having NSN activity as disclosed herein may be used to degrade contaminating nucleic acids in protein solutions in order to achieve a low (host cell) nucleic acid content of the protein solution. Nucleic acids in protein solutions may have undesired effects such as the activation of cells that are brought in contact with the protein solution comprising said nucleic acids. For example, nucleic acids may bind to Toll-like receptors of cells and thereby induce cellular effects. To degrade said contaminating nucleic acids, the polypeptide having NSN activity may be added to the protein solution comprising the target protein, and the mixture is incubated, for example 30 min at about 37° C. or 2 hours at about 4° C. In one example, a recombinant protein is expressed in *E. coli*, the cells are lysed, and the bacterial lysate is incubated with the polypeptide having NSN activity to degrade bacterial host cell DNA and/or RNA. The bacterial lysate may comprise a cation complexing agent such as EDTA to increase the lysis efficiency. In another example, purified target protein is incubated with the polypeptide having NSN activity to degrade host cell DNA and/or RNA. Afterwards, the polypeptide having NSN activity may be removed from the target protein, for example by chromatography or by using an immobilized polypeptide having NSN activity.

Definitions

Unless defined otherwise, technical and scientific terms used herein have the same meaning as commonly understood by one of ordinary skill in the art to which this invention belongs. The term "° C." as used herein means degree Celsius.

The term "about" as used herein with respect to measured values such as for temperature, pH, and kinetic values of a protein ($k_{cat}$) refers to a range around the number indicated. The range is determined by the methods used to determine said values. For temperatures, the range is +/−1° C., i.e. "about 4° C." means 4° C.+/−1° C. and therefore covers the range from 3° C. to 5° C., and "about 4° C. to 10° C." means the range from 4° C. to 10° C.+/−1° C. and therefore covers the range from 3° C. to 11° C. For pH values, the range is +/−0.3 pH units, i.e. "pH about 7" means pH 7+/−0.3 and therefore covers the range from pH 6.7 to pH 7.3. For enzymatic activities, the range is from 80% to 125% of the measured value, i.e. for a $k_{cat}$ value of 339 s-1 a range from 271 to 424 $s^{-1}$ is covered. For molar concentrations, the range is +/−20% of the value, i.e. "about 10 mM" means 10 mM+/−2 mM and therefore covers the range from 8 mM to 12 mM.

The term "isolated" is used herein to indicate that the polypeptide (or nucleic acid or host cell) exists in a physical milieu distinct from that in which it occurs in nature. For example, the isolated polypeptide may be substantially isolated (for example enriched or purified) with respect to the complex cellular milieu in which it naturally occurs, such as in a crude extract. When the isolated polypeptide is enriched or purified, the absolute level of purity is not critical and those skilled in the art can readily determine appropriate levels of purity according to the use to which the material is to be put. In some circumstances, the isolated polypeptide forms part of a composition (for example a more or less crude extract containing many other substances) or buffer system, which may for example contain other components.

The term "nucleic acid" or "nucleic acid molecule" in accordance with the present invention includes DNA, such as cDNA or double or single stranded genomic DNA and RNA. In this regard, "DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases that are linked together on a ribose sugar backbone. RNA typically has one strand of nucleotide bases. Included are also single-and double-stranded hybrid molecules, i.e., DNA-RNA. The nucleic acid molecule may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.).

The term "polypeptide" as used herein interchangeably with the term "protein" describes linear molecular chains of amino acids, including single chain proteins, containing more than 30 amino acids, whereas the term "peptide" describes linear molecular chains of amino acids, including single chain proteins, containing less than and up to 30 amino acids. Polypeptides may further form oligomers consisting of at least two identical or different molecules. The corresponding higher order structures of such multimers are, correspondingly, termed homodimers, homotrimers etc. The polypeptides of the invention may form homomultimers, such as homodimers. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide" and "protein" also refer to naturally modified polypeptides and proteins e.g. by glycosylation, acetylation, phosphorylation, ubiquitinylation and similar modifications which are well known in the art.

As used herein, the term "non-specific nuclease activity" (herein also abbreviated as "NSN activity"), comprises all kinds of nuclease activity that does not require a recognition site for the nuclease in the nucleic acid. Therefore, it is a sequence-independent nuclease activity. In contrast, restriction enzymes are typically sequence-dependent nucleases, i.e. they have a site-specific nuclease activity. Said nucleic acids comprise, for example, DNA and RNA. NSN activity of a polypeptide may be measured by incubating 10 ng of said polypeptide with 500 ng nucleic acid for 1 minute at about 37° C. in a phosphate-based buffer at pH 7.0. The polypeptide has NSN activity when under these conditions at least 0.1% sequence-independent degradation of the nucleic acid is observed.

Said NSN activity means an activity to preferentially digest or degrade nucleic acid molecules existing in linear, circular, single-stranded or double-stranded nucleic acids. An RNA single strand, an RNA double strand, a DNA single strand, a DNA-DNA double strand, a DNA-RNA double strand, and a double strand moiety in a nucleic acid molecule having a partial single strand structure and a partial double strand structure are included in said nucleic acid molecules. Also included in said nucleic acid molecules are modified nucleic acids, for example methylated, biotinylated, and fluorescently labeled nucleic acids, that can be digested or degraded by NSN activity. Said nucleic acid molecules also comprise nucleic acid analogs that can be digested or degraded by NSN activity. Said partial single strand structure includes, for example, mismatch of bases, bulge structure, loop structure, flap structure and pseudo-Y structure and the like. The non-specific nuclease activity can be measured quantitatively for example by the Kunitz method (Kunitz M. (1950) J. Gen. Physiol. 33:349-362) and is calculated according to MacLellan and Forsberg (2001, Microbiology 147:315-323). The non-specific nuclease activity can also be measured qualitatively for example by incubating the isolated enzyme with nucleic acids under appropriate conditions (for example 100 ng enzyme is incubated with 5 g nucleic acid for 1 minute at about 37° C. in a phosphate-based buffer at pH 7.0), carrying out an agarose gel electrophoresis, staining the nucleic acids (for example by ethidium bromide) and comparing the nucleic acids bands in the presence and absence of the enzyme.

The terms "relative NSN activity" as used herein means that the nuclease activity of an enzyme is determined at a first temperature under defined conditions (for example, pH 7.0, phosphate-based buffer) and set to 100%. The nuclease activity of said enzyme is also determined at a second temperature and the measured activity is calculated as % of the activity at the first temperature. For example, when the first temperature is about 4° C. and the second temperature is about 25° C., and the NSN activity at about 4° C. is at least 1% of the NSN activity at about 25° C., then the relative NSN activity at about 4° C. is at least 1% of the relative NSN activity at about 25° C.

The term "catalytic rate constant kc" as used herein means the constant that describes the turnover rate of an enzyme-substrate complex to product and enzyme. For a nuclease, substrates comprise nucleic acids, and products comprise digested and degraded nucleic acids including oligonucleotides and nucleotides. A $k_{cat}$ value of 10 s$^{-1}$ is identical to 10 reactions per second; for a nuclease, said reactions are cleavages of internucleotide bonds.

As used herein, the term "cation complexing agent" comprises substances, chemicals and molecules that bind certain metal cations, so that the cations cannot normally react with other elements, ions or molecules. Cation complexing agents include, but are not limited to, chelating agents, organophosphorus compounds, organic acids and their salts, and microporous minerals. Examples comprise EDTA (ethylenediaminetetraacetic acid), EGTA (ethylene glycol-bis(2-aminoethylether)-N,N,N',N'-tetraacetic acid), DOTA (1,4,7,10-tetraazacyclododecane-1,4,7,10-tetraacetic acid), DTPA (diethylenetriaminepentaacetic acid), MGDA (methylglycine N,N-diacetic acid), GLDA (glutamate diacetate), NTA (nitrilotriacetic acid), IDS (iminodisuccinate), HEEDTA (N-(2-hydroxyethyl)ethylenediamine-N,N',N'-triacetic acid), STPP (sodium tripolyphosphate), TTHA (triethylenetetramine-N,N,N',N'',N''',N'''-hexaacetic acid), phosphonates, DFOA (desferrioxamine), DMSA (2,3-dimercaptosuccinic acid), penicillamine, dimercaprol, and zeolites.

The term "solution" in the context of a solution that contains the polypeptide of the present invention means a solution that allows NSN activity of the polypeptide as disclosed herein. The solution may be a buffer, a cell culture medium, or any other aqueous liquid that enables NSN activity of the polypeptide. Buffers for non-specific nucleases are well-known in the art. Said buffers may contain basic components as, for example, phosphate, Tris, Hepes, NaCl, KCl, Mg2+ ions, Ca2+ ions, Mn2+ ions, Zn2+ ions, Co2+ ions detergents, reducing agents, glycerol, carbohydrates, and preserving agents.

The term "solution having a concentration of a cation complexing agent in a range of about 0.1 mM to 50 mM, 0.1 mM to 20 mM, 1 mM to 20 mM, 1 mM to 10 mM, or 1 mM to 4 mM" as used herein refers to a solution that contains such cation complexing agents in the given concentration in addition to other components in said solution.

As used herein, the term "identity" (of proteins and polypeptides) with respect to amino acid sequences is used for a comparison of proteins chains. Calculations of "sequence identity" between two sequences are performed as follows. The sequences are aligned for optimal comparison purposes (e.g., gaps can be introduced in one or both of a first and a second amino acid sequence for optimal alignment and non-homologous sequences can be disregarded for comparison purposes). The optimal alignment is determined as the best score using the "lalign" program on the ExPASy Bioinformatics Resource Portal (embnet.vital-it.ch/software/LALIGN_form.html) with a Blossum 50 scoring matrix with a gap-open penalty of −12, and a gap-extension penalty of −2. The amino acid residues at corresponding amino acid positions are then compared. When a position in the first sequence is occupied by the same amino acid residue at the corresponding position in the second sequence, then the molecules are identical at that position. The percent identity between the two sequences is a function of the number of identical positions shared by the sequences.

As defined in the aspects and embodiments herein, certain amino acid sequence identities are envisaged by the present invention. Envisaged are amino acid sequence identities of at least comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to the respective amino acid sequence in accordance with the invention, preferably to SEQ ID NO:2. As evident from FIG. 1, the inventors were able to identify the degree of identity to SEQ ID NO: 2 that is necessary to save the characteristics of the polypeptide encompassed by SEQ ID NO:2. The majority of homologous polypeptides that were identified in a BLASTP analysis using SEQ ID NO: 2 as query exhibit amino acid identities between 96.7% and 100%. These sequences exclusively belong to the family Pseudomonaceae and to the genus Pseudomonas. In addition, identical sequences that were grouped as "MULTISPECIES: phospholipase D family protein [Pseudomonas]" under the accession number WP_048402802.1 exhibited an identity of 85.0% on the amino acid level. The annotated phospholipase D family proteins from Pseudomonas sp. MWU 12-21 15 (WP_103486374.1) and from Pseudomonas coleopterorum (WP 090362547.1) exhibited identities of 73.9% and 73.2%, respectively, when compared with SEQ ID NO:2 (FIG. 1C). The most closely related homologues from outside the genus Pseudomonas that are less than 69% identical have been found in the families Enterobacteriaceae and Moraxellaceae including Escherichia coli ("endonuclease [Escherichia coli]' accession number KZ082453.1, SEQ ID NO: 10).

The percentage (%) identities as given in FIG. 1 that have a decimal place (for example, 73.2%) are used as rounded numbers without a decimal place in the description, for example "having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity". It is rounded to the nearest integer rounding half up, i.e. 98.5 gets rounded to 99. A value of 99.3% therefore gets rounded to 99%, 98.7% gets rounded to 99%, 97.4% gets rounded to 97%, 96.7% gets rounded to 97%, 73.9% gets rounded to 74%, 73.2% gets rounded to 73%, and 68.6%% gets rounded to 69%.

Figure 2:
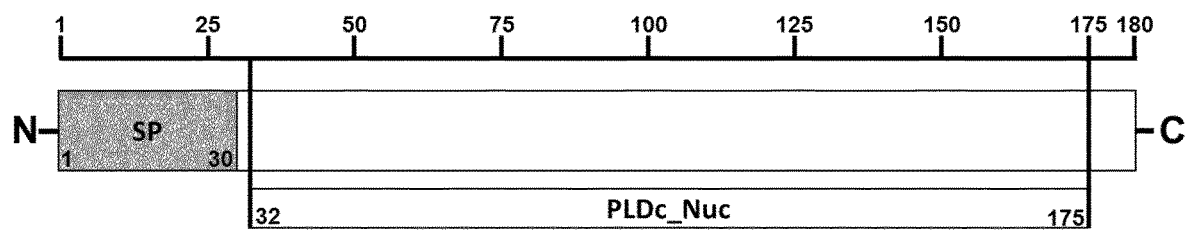
FIG. 2: Protein domain structure of P.vNuc. Schematic illustration of the protein including the predicted signal peptide (SP) composed of amino acid residues 1-30. "PLDc_Nuc": annotated domain in the database (amino acid residues 32-175).

The amino acid sequences as given in SEQ ID NO:2 to SEQ ID NO:6 refer to all constellations of the respective amino acid sequence which retain the intended function of the respective amino acid sequence as defined herein. In other words, the divergences between the polypeptide sequences of SEQ ID NO:2 to SEQ ID NO:6, respectively, should not affect their potential as having the non-specific nuclease activity as defined herein. Therefore, the amino acid sequences of SEQ ID NO: 2 to SEQ ID NO: 6 can be the full length amino acid sequence of the SEQ ID NO:2 to SEQ ID NO:6, respectively. It can also be a variant thereof which have some amino acids deleted, added or replaced while still retaining the intended function as described herein. Therefore, included in this definition are variants of the amino acid sequences in SEQ ID NO:2 to SEQ ID NO:6, respectively. The amino acid sequence of non-specific nucleases as disclosed herein may also be a functional fragment of a full-length polypeptide having at least comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity with SEQ ID NO:2. In this context the term "functional fragment" means that the fragment is able to degrade nucleic acids, i.e. it has non specific nuclease activity. Said NSN activity of said "functional fragment" may be identified by, for example, conducting qualitative and/or quantitative assays as described in example 7 using isolated fragments. Preferentially, said functional fragment has NSN activity at about 4° C. Preferentially, said functional fragment has the same non-specific nuclease activity as the polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity with SEQ ID NO:2. Preferentially, said functional fragment comprises or consists of the "PLDc_Nuc" domain (example 1, FIG. 2).

In another embodiment the polypeptide as disclosed herein may be a fusion protein comprising the polypeptide having at least comprising or consisting of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity with SEQ ID NO:2 or a functional fragment thereof and in addition further amino acids, e.g. representing a peptide tag (for example a polyhistidine tag), a further domain of another polypeptide or a complete sequence of another polypeptide.

The term "cell culture device" as used herein means any kind of device that enables storage and/or growth of cells. Examples comprise cell culture flasks, cell culture bags, cell culture bottles, cell culture chambers, membranes, and single-or multi-well plates. Said cells comprise, for example, bacterial cell, yeast cells, insect cells, mammalian cell, and hybridoma cells.

The term "vector" in accordance with the invention preferably means a plasmid, cosmid, virus, bacteriophage or another vector used e.g. conventionally in genetic engineering which carries the nucleic acid molecule of the invention encoding the polypeptide of the invention. Accordingly, the nucleic acid molecule of the invention may be inserted into several commercially available vectors.

The "host cell" in accordance with the invention may be produced by introducing the nucleic acid or vector(s) of the invention into the host cell which upon its/their presence preferably mediates the expression of the nucleic acid of the invention encoding the polypeptide of the invention. The host from which the host cell is derived may be any prokaryote or eukaryotic cell.

Preferred examples for host cell to be genetically engineered with the nucleic acid molecule or the vector(s) of the invention is a cell of yeast, insects, mammalia, and/or bacteria such as E. coli. The most preferred host cell is E. coli.

The term "microfluidics" as used herein refers to the technology that deals with the behavior, precise control and manipulation of fluids that are geometrically constrained to a small, typically sub-millimeter, scale at which capillary penetration governs mass transport. Typically, in microfluidic systems fluids are transported, mixed, separated, or otherwise processed. The term "microfluidic channel" refers to a channel of which at least one dimension must be in the range of hundreds of micrometers or less.

The term "clogging" as used herein refers to a process wherein substances in a solution change the flow of the solution in such a way that the flow rate declines or drops down to zero. Said substances that may induce clogging comprise, for example, cells, cell fragments and debris, cell components such as nucleic acids, aggregates, particles including colloidal particles, biological particles, and nanoparticles, precipitates such as salt precipitates or protein precipitates, and substances that have or induce a high viscosity of the solution. Clogging may occur, for example, in channels including fluidic and microfluidic channels, for example used in cell sorting devices, in matrices of columns used during, for example, magnetic cell separation, an in/on filters and in/on filter pores that are used in, for example, cell culture devices. Clogging may be reduced or prevented when size and amount of clogging-inducing agents (such as nucleic acids) are reduced.

EXAMPLES

Hereinafter, the present invention is described in detail and specifically with reference to the examples, which however are not intended to limit the present invention.

Example 1: Identification of the Non-Specific Nuclease vNuc from *Pseudomonas syringae* and from Phylogenetically Related Pseudomonads For the identification of putative non-specific bacterial endonucleases, BLAST analyses were conducted using StN uc from *Salmonella enterica* subsp. *enterica* serovar *Typhimurium* as query (NCBI entry WP_00073 1968.1, SEQ ID NO:7). The BLASTP server at NCBI Entrez (blast.ncbi.nlm-.nih.gov/Blast.cgi?PAGE=Proteins) was used to screen for putative endonucleases derived from cold-active bacterial species. A putative endonuclease of the PLD-family from *P. syringae* genomosp 2 (WP_050543 862.1, SEQ ID NO:1). was retrieved that displayed an amino acid sequence identity of 57.2% compared to .S7N uc (WP_000731968.1, SEQ ID NO:7) in a local alignment omitting putative secretion signals. The gene encoding P.vNuc consists of 552 nucleotides including a STOP codon sequence, and the deduced amino acid sequence is composed of 183 amino acid residues. A molecular weight of 19972.74 Da and an isoelectric point of 9.4 was calculated using the tool "Compute pEMw tool" (web.expasy.org/compute.pi/). A signal sequence of 30 amino acid residues (Metl-Ala30) was predicted using the tool "Signal P 4.1" (www.cbs.dtu.dk/services/SignalP/). The predicted mature amino acid sequence of P.vNuc (without the predicted signal peptide sequence) is given as SEQ ID NO:2. A molecular weight of 16826.93 Da and an isoelectric point of 9.0 was calculated for the predicted mature protein. The tool CD-S (Conserved Domain Search, www.ncbi.nlm-.nih.gov/Structure/cdd/wrpsb.cgi) using the option to search against database "CDD v3.16-50369 PSSMs" revealed the conserved and annotated domain "PLDc_Nuc" (amino acid residues Glu32-Glnl75) that is based on the crystal structure of StN uc from *S. enterica* subsp. *enterica* serovar *Typhimurium* and that is a characteristic of members of the PLD-family. The superfamily of PLD-proteins is further characterized by the highly conserved catalytic motif HxK (x) 4D(x) 6GSxN that has been identified in P.vNuc by using an amino acid sequence alignment of P.vNuc (SEQ ID NO: 1) with StN uc from *S. enterica* subsp. *enterica* serovar *Typhimurium* (SEQ ID NO: 7). The "lalign" program on the ExPASy Bioinformatics Resource Portal (embnet.vital-it.ch/software/LALIGN form.html) was used to align P.vNuc and .SYNuc. The amino acid residues of the catalytic motif are located at positions Hisl22, Lysl24, Aspl29, Glyl36, Serl37, and Asnl39 in $_{Ps}$Nuc, respectively. Further BLASTP analyses (using SEQ ID NO:2 as query) combined with multiple sequence alignments revealed that annotated "phospholipase D family" and "endonuclease" proteins from the family Pseudomonaceae exclusively belong to the genus *Pseudomonas* and exhibit mostly protein identity levels between 96.7 and 99.3% (FIG. 1, the % identity accounts for the 153 amino acid residues of SEQ ID NO:2). More than 50 accession numbers comprising homologues of SEQ ID NO:2 that exhibit sequence identities between 96.7% and 100% on the amino acid level, were identified. Additionally, identical sequences from a defined group, such as "MULTISPECIES: phospholipase D family protein [*Pseudomonas syringae* group genomesp. 2]" were assigned to a joint accession number, for example WP_050543 862.1, which comprises identical sequences that are annotated as "phospholipase D family protein". These sequences were derived from the following strains: *Pseudomonas savastanoi* pv. *glycinea* str. B076, *Pseudomonas savastanoi* pv. *glycinea* str. race 4, *Pseudomonas savastanoi* pv. *glycinea*, *Pseudomonas amygdali* pv. *morsprunorum*, *Pseudomonas amygdali* pv. *eriobotryae*, *Pseudomonas amygdali* pv. *tabaci*, and *Pseudomonas amygdali* pv. *lachrymans*. When including these strains that are contained in said MULTISPECIES groups, the number of known homologues of SEQ ID NO:2 that exhibit sequence identities between 96.7% and 100% on the amino acid level is more than 100. Three further annotated "phospholipase D family" proteins were identified with protein identities of 73.2%, 73.9%, and 85.0% compared to SEQ ID NO:2, respectively. The highest congruence between P.vNuc and non-Pseudomonaceae was identified to be with members of the families Enterobacteriacea and Moraxellaceae including isoenzymes identified in species of the genera *Salmonella, Escherichia, Klebsiella, Citrobacter*, and *Acinetobacter*. The protein sequence identity of these non-Pseudomonaceae enzymes and P.vNuc (SEQ ID NO:2) was maximum 68.6% (FIG. 1C). No annotated sequences from bacterial species outside the family Pseudomonaceae were identified by BLASTP analyses at NCBI Entrez that were more closely related by pairwise alignments. P.vNuc variants with single amino acid substitutions that were discovered by multiple sequence alignments at least in two annotated sequences of TANuc-related sequences in the family Pseudomonaceae without their respective signal peptides were cloned for protein production purposes (see Example 2). The PsNuc variants comprising single amino acid substitutions are /ANuc_Arg53Gly (SEQ ID NO:3), /ANuc_Asn95Scr (SEQ ID NO:4), ANuc Glyl 16Ala (SEQ ID NO:5), and P.vNuc Asp 157Gly (SEQ ID NO:6), respectively.

Example 2: Cloning of Genes Encoding for /Anuc and /Anuc Variants and Transformation of *E. coli*

Figure 3:
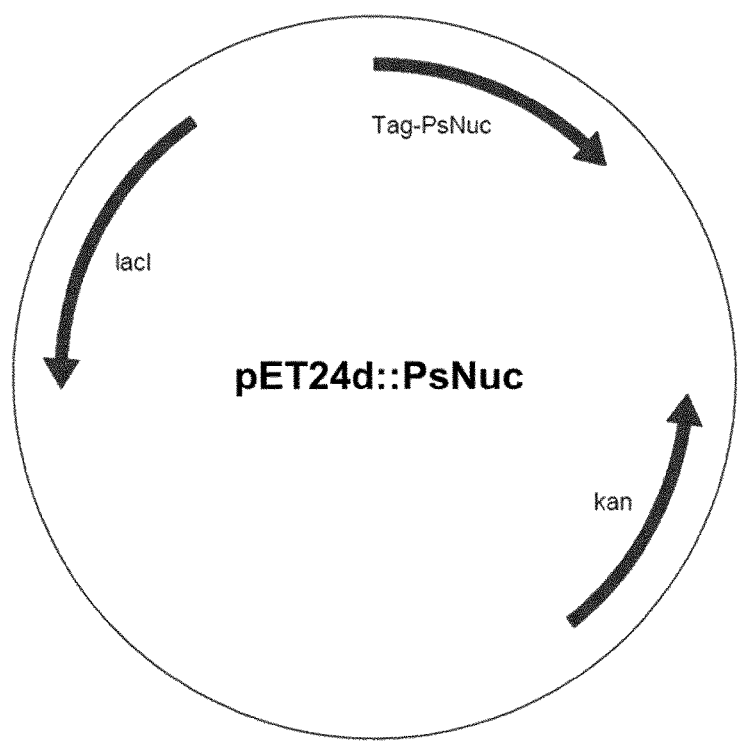
FIG. 3: Illustration of the plasmid pET24d: P.vNuc for recombinant expression of P.vNuc in *E. coli*. The nuclease P.vNuc is encoded as an affinity tag-fusion protein ("Tag-PsNuc"). la$_{cf}$.

DNA sequences were deduced from the mature amino acid sequences of /Anuc and variants thereof without the predicted signal peptide sequence (SEQ ID NO: 2, SEQ ID NOG, SEQ ID NO:4, SEQ ID NOG, and SEQ ID NOG, respectively). Genes were synthesized as codon optimized sequences for the expression in *Escherichia coli* (ATUM, Inc.) and cloned into pET24d(+) vector (Merck Millipore) as a fusion protein comprising an N-terminal affinity tag that allows affinity purification of the recombinant P.vNuc proteins (FIG. 3). *E. coli* DH5a cells (Thermo Fisher Scientific) were transformed with the respective pET24d::P.vNuc plasmids by heat shock. Therefore, cells were thawed on ice for 10 minutes and supplemented with 10-100 ng of plasmid DNA. After another incubation on ice for 20 minutes, a heat shock at 42° C. was applied for 45 seconds. Afterwards cells were incubated on ice for 2 min and mixed with preheated B medium and incubated on a shaker at 37° C. for 45 min. Finally, cells were plated on kanamycin-containing (50 pg/ml) agar plates to select for transformants after overnight incubation.

Example 3: Detection of Dnase Activity in *E. coli* Expressing Recombinant F.vNuc Proteins on Blue Agar Plates Transformed *E. coli* clones of example 2 were analyzed for DNase activity using "DNase Test Agar with Toluidine Blue" (Merck Millipore). DNases depolymerize the DNA resulting in the production of a bright pink reaction due to the metachromic property of the toluidine blue in the agar. Clear halos surrounding the colony were detected when clones were grown that displayed DNase activity (FIG. 4). Cell lysis was observed of *E. coli* expressing the gene encoding F.vNuc; *E. coli* expressing N uc did not show cell lysis (Gottlin et al. (1998) Proc Natl Acad Sci USA. 95:9202-9207), suggesting a higher DNase activity of P.vNuc compared to StN uc.

Example 4: Production of Recombinant P.vNuc Proteins in *E. coli*

For production of recombinant P.vNuc and variants thereof, *E. coli* Veggie BF21 (DE3) cells (Merck Millipore) were transformed with the appropriate expression plasmid, for example pET24d::P.vNuc. Cells were precultured overnight in Veggie FB medium (10 g/l veggie peptone, 5 g/l veggie yeast extract, 10 g/l NaCl) at 37° C. under selective pressure using appropriate antibiotics. Afterwards, fresh cultures were inoculated at $OD_{600}$=0.05 and aerobically grown on a shaker at 37° C. for 2-3 hours. When the exponential growth phase ($OÜ_{600}$=0.6-0.8) was reached, gene expression was induced by the addition of 0.4 mM IPTG (Isopropyl β-D-1-thiogalactopyranoside). After 4 hours, cells were harvested by centrifugation.

Example 5: Purification of Recombinant P.vNuc Proteins from Crude Cell Extracts Cells of example 4 were dissolved in lysis buffer (20 mM $NaH_2PO_4$, pH 8.0) and disrupted by sonication to obtain crude protein extract. The protein debris was sedimented by centrifugation and the supernatant containing soluble P.vNuc and variants thereof was transferred into a sterile tube. Using a combination of affinity chromatography and cation exchange chromatography, P.vNuc and variants thereof were purified. Afterwards, the affinity tag was proteolytically cleaved off followed by another affinity chromatography step to obtain pure untagged protein in the flow-through (FIG. 5), resulting in isolated P.vNuc proteins.

Example 6: Biophysical Characterization of Purified Recombinant P.vNuc

The determination of the molecular weight of a monomer of PsNuc was done by means of sodium dodecyl sulfate polyacrylamide gel electrophoresis (SDS-PAGE, FIG. 6) and mass spectrometry (FIG. 7). At denaturing conditions, recombinant E.vNuc exhibited a molecular weight of about 16 kDa, which has been confirmed by electrospray ionization mass spectrometry (16826.90 Da; the calculated molecular mass using the tool "Compute pEMW", web.expasy.org/compute_pi/, is 16826.93 Da). Purity of P.vNuc proteins was >90% as determined by SDS-PAGE.

Example 7: Assays for the Examination of the NSN Activity of Recombinant P.vNuc NSN activity of proteins of example 5 was determined by a qualitative assay and/or a quantitative assay. In the qualitative activity assay, up to 0.5. µg of pure enzyme was incubated with 0.5 pg-5 pg of substrate (DNA or RNA) at about 20° C. or about 37° C., respectively. Incubation time was between 10 min and 24 h. The reactions were stopped by the addition of 0.25% (w/v) sodium dodecyl sulfate. The samples were supplemented with DNA or RNA gel loading dye (Thermo Fisher Scientific) and loaded onto a 1% (w/v) agarose gel. Running the gel took place in 1×TAE-buffer (Tris-acetate-EDTA), at a constant electric voltage of 100 V for 60 min to separate nucleic acids according to their sizes. Nucleic acids were stained with ethidium bromide.

In the quantitative activity assay, up to 0.1 pg of pure enzyme was incubated with substrate at about 4° C., about 25° C., or about 37° C., respectively. Assay was done continuously or reaction was stopped using 1 volume 4% (v/v) ice-cold perchloric acid after 5-10 min. An increase in absorbance by DNA at an optical density at 260 nm is determined as a result of the degradation of the polymer to give nucleotides or short oligonucleotides. A VICTOR™ X4 Multilabel Plate Reader was used to determine enzymatic activities.

Example 8: Examination of Enzymatic Activity

Enzymatic activity of purified recombinant EvNuc proteins towards nucleic acids and the PLD-substrates phosphatidylcholine and bis(4-nitrophenyl) phosphate NSN activity of proteins of example 5 was determined by the qualitative activity assay as described. in example 7 using the following substrates circularized plasmid DNA (pET da Nuc), MS2 RNA (Sigma-Aldrich), single stranded DNA from calf thymus (Sigma-Aldrich), double stranded sheared genomic DNA (UltraPure™ Salmon Sperm DNA Solution, Thermo Fisher Scientific), and double stranded unsheared genomic DNA (Deoxyribonucleic acid from calf thymus, Sigma-Aldrich). All substrates were completely degraded by the NSN activity of P.vNuc (FIG. 8).

In addition, enzymatic activity of purified P.vNuc of example 5 towards phosphatidylcholine was tested by applying the Amplex® Red Phospholipase D Assay Kit (Thermo Fisher Scientific). No enzymatic activity was detected. In addition, no activity towards the artificial substrate bis(4-nitrophenyl) phosphate (Merck Chemicals GmbH) was detected. The latter is in contrast to 57Nuc protein from *S. enterica* subsp. *Enterica* serovar *Typhimurium* (Zhao et al. (1997) Prot. Sci. 6:2655-2658). As a positive control, phospholipase D from *Streptomyces chromofuscus* (.PFD, Merck Chemicals GmbH) was used which hydrolyzed both PFD-substrates; the activity of ScPFD was set to 100%. (FIG. 9). All experiments were done according to the instructions of the manufacturers.

Example 9: Influence of the pH on the NSN Activity of Purified Recombinant P.vNuc NSN activity of proteins of example 5 was determined by the quantitative activity assay as described in example 7. To determine the effect of different pH values on the NSN activity of P.vNuc, purified proteins of example 5 were analyzed in a pH range between about pH 4 and about pH 9. For this purpose, P.vNuc was incubated at about 25° C. for 10 min with sheared dsDNA from salmon sperm in the following buffer systems: pH 4-6 in 50 mM sodium acetate buffer, pH 5-7 in 50 mM sodium phosphate buffer, pH 7-9 in 50 mM Tris-HCl buffer. The maximum activity was determined at about pH 7 using 50 mM sodium phosphate buffer and was set to 100% (FIG. 10). In the range of about pH 5 to about pH 9, the relative NSN activity of F.vNuc was at least 9% of the maximum NSN activity.

Example 10: Influence of the Temperature on the NSN Activity of Purified Recombinant F.vNuc To determine the effect of different temperatures on the NSN activity of P.vNuc, purified proteins of example 5 were analyzed using the quantitative activity assay as described in example 7 at the following temperatures: about 4° C., about 10° C., about 20° C., about 25° C., about 30° C., about 35° C., about 40° C., about 45° C., about 50° C., and about 60° C. (FIG. 11). For this purpose, the substrate (sheared dsDNA from salmon sperm) and the enzyme were independently preincubated for 5 min in 50 mM sodium phosphate buffer, pH 7.0 at the respective temperatures. The reaction was started by mixing preincubated solutions containing substrate and buffer. Maximum NSN activity of F.vNuc was observed at about 45° C. and was set to 100%. The relative NSN activity was >70% between about 30° C. and about 45° C., >35% between about 25° C. and about 45° C., >25% between about 20° C. and about 45° C., >10% between about 20° C. and about 50° C., >5% in the range between about 10° C. and about 50° C., and about 4% between about 4° C. and about 50° C. when compared to the maximum NSN activity at about 45° C.

Example 11: Influence of Cation Complexing Agents on the NSN Activity of Purified Recombinant F.vNuc Proteins To determine the effect of the cation complexing agents on the NSN activity of F.vNuc, purified proteins of example 5 were preincubated on ice for 60 min in the presence of 1 mM, 2 mM, 4 mM, 10 mM 20 mM, and 50 mM ethylenediaminetetraacetic acid (EDTA), ethylene glycol-bis(2-aminoethylether)-N,N,N',N'-tetraacetic acid (EGTA), and 1,4,7,10-tetraazacyclododecane-1,4,7,10-tetraacetic acid (DOTA), respectively. Afterwards, a qualitative activity assay and a quantitative activity assay as described in example 7 using sheared dsDNA from salmon sperm were conducted at about 20° C. The DNA was analyzed by agarose gel electrophoresis (FIG. 12), and relative activities were calculated based on data from the quantitative activity assay. The NSN activity in the absence of a cation complexing agent was set to 100%. Table 1 shows relative NSN activities of purified F.vNuc. For EGTA and DOTA, the NSN activity is 96% or more for concentrations of up to 20 mM. Even with 50 mM EGTA and DOTA, NSN activity is still 89% and 88%, respectively. For EDTA, NSN activity is 91% or more for concentrations of up to 4 mM, and 88-89% for up to 20 mM. Even with 50 mM EDTA, NSN activity is still 67%.

TABLE 1

Influence of different concentrations of EDTA, EGTA and DOTA on the NSN activity of P.vNuc

| Concentration of cation complexing agent [mM] | Relative NSN activity in the presence of | | |
|---|---|---|---|
| | EGTA | DOTA | EDTA |
| 0 | 100% | 100% | 100% |
| 1 | 96% | 97% | 96% |
| 2 | 98% | 99% | 91% |
| 4 | 96% | 97% | 94% |
| 10 | 98% | 101% | 88% |
| 20 | 96% | 96% | 89% |
| 50 | 89% | 88% | 67% |

Example 12: Influence of NaCl and KCl on NSN Activity of Purified Recombinant P.vNuc Proteins To determine the effect of NaCl and KCl, respectively, on the NSN activity of E.vNuc, purified proteins of example 5 were preincubated on ice for 60 min in the presence of 50 mM, 100 mM, 250 mM, 500 mM and 1,000 mM of either NaCl or KCl. Afterwards, a qualitative activity assay and a quantitative activity assay using sheared dsDNA from salmon sperm were conducted at about 20° C., the DNA was analyzed by agarose gel electrophoresis (FIG. 13), and relative activities were calculated based on data of the quantitative activity assay. Reaction setup was done as described in example 7. Table 2 shows relative NSN activities of purified E.vNuc. NSN activity is 88% or more for concentrations of up to 100 mM of each salt. At 250 mM, a partial inhibition is observed, resulting in an NSN activity of 59-62%. 500 mM results in a strong but not full inhibition, reducing the NSN activity to 4% (NaCl) and 13% (KCl). NSN activity is fully inhibited in the presence of 1,000 mM NaCl and KCl, respectively.

TABLE 2

Influence of different concentrations of NaCl and KCl on the NSN activity of P.vNuc

| Concentration of salt [nM] | Relative NSN activity in the presence of | |
|---|---|---|
| | NaCl | KCl |
| 0 | 100% | 100% |
| 50 | 97% | 97% |
| 100 | 88% | 93% |
| 250 | 62% | 59% |
| 500 | 4% | 13% |
| 1,000 | 0% | 0% |

Example 13: Influence of Divalent Metal Ions on NSN Activity of Purified Recombinant P.vNuc Proteins To determine the effect of divalent metal ions on the NSN activity of Nuc, purified proteins of example 5 were preincubated on ice for 60 min in the presence of 0.1 mM, 0.5 mM, 1 mM, 2 mM, and 10 mM MgCl 2, MnCl 2, CaCl 2, or CoCl 2, respectively. Afterwards, a qualitative activity assay using sheared dsDNA from salmon sperm was done at about 20° C., and the DNA was analyzed by agarose gel electrophoresis (FIG. 14). Reaction setup was done as described in example 7. The NSN activity of P.vNuc is not impaired in the presence of any of the divalent metal ions up to a concentration of 10 mM.

Example 14: Determination of Kinetic Parameters of Purified Recombinant E.vNuc Proteins Kinetic parameters of purified E.vNuc proteins of example 5 were analyzed using sheared dsDNA from salmon sperm at the following concentrations: 0.005 mg/ml, 0.01 mg/ml, 0.025 mg/ml, 0.05 mg/ml, 0.1 mg/ml, 0.2 mg/ml, 0.4 mg/ml, and 0.6 mg/ml. End point measurements were done according to example 7 to calculate $V_{max}$ and K M values. Data were fitted to the Michaelis-Menten equation and the "Solver" add-in of Microsoft Excel was used to perform a nonlinear regression. A mean molecular mass of 330 g/mol per nucleotide was used to convert K M values from g/ml to p M (MacLellan and Forsberg (2001) Microbiology 147:315-323). $k_{cat}$ was obtained by using the formula $k_{cat}=V_{max}/[Eo]$, by assuming that the degradation of 0.05 mg DNA resulted in a change in absorbance of 0.3. Table 3 shows relative $k_{cat}$ values of purified E.vNuc proteins including variants with single point mutations. $k_{cat}$ of E.vNuc was determined at about 4° C., about 25° C., and about 35° C. (FIG. 15A). The $k_{cat}$ value at about 4° C. is 19% compared to the value at about 25° C. and 6% compared to the value at about 35° C. To compare the enzymatic performance of E.vNuc and single mutation variants, $k_{cat}$ values were determined at about 25° C. and about pH 7.0 in the absence of EDTA (FIG. 15B). Two variants, P.vNuc_Arg53Gly and /ANuc Asp 157Gly, showed increased $k_{cat}$ values (113% and 130% of the value of P.vNuc), demonstrating an increased NSN activity. The influence of EDTA on the $k_{cat}$ of P.vNuc was investigated in a quantitative activity assay at about pH 7.0 (FIG. 15C) and at about pH 8.0 (FIG. 15D). At 20 mM EDTA, the $k_{cat}$ values were nearly identical (even slightly increased) to those at 0 mM EDTA. At 50 mM EDTA, the $k_{cat}$ values were 83% (pH 7.0) and 40% (pH 8.0) compared to the values at 0 mM EDTA, indicating that the NSN activity is not inhibited by 20 mM EDTA and only slightly at 50 mM EDTA. The latter can be an effect of salt inhibition similar to the observation in example 12 that higher concentrations of NaCl and KCl partially inhibit the NSN activity.

TABLE 3

$k_{cat}$ values of P.vNuc proteins

| PsNuc protein | SEQ ID NO: | $k_{cat}$ (s$^{-1}$) | measured at (° C.) |
|---|---|---|---|
| PsNuc | 2 | 339 | 4 |
| PsNuc | 2 | 1,756 | 25 |
| PsNuc | 2 | 5,653 | 35 |
| PsNuc_Arg53Gly | 3 | 1,979 | 25 |
| PsNuc Asn95Ser | 4 | 1,399 | 25 |
| PsNuc_Gly116Ala | 5 | 1,529 | 25 |
| PsNuc_Asp157Gly | 6 | 2,290 | 25 |

Example 15: Identification of Related Bacterial PLD-Nucleases from Species Outside the Pseudomonads To distinguish P.vNuc and characterized variants (P.vNuc_Arg53Gly, P.vNuc_Asn95Ser, /ANuc Gly1 16 Ala and /ANuc Asp 157Gly) within the group of Pseudomonads from related bacterial PLD-like nucleases, two putative PLD-proteins were identified by BLASTP analysis at NCBI Entrez (blast.ncbi.nlm.nih.gov/Blast.cgi?PAGE=Proteins) using P.vNuc (SEQ ID NO:2) as a query. The highest congruence between P.vNuc and non-Pseudomonaceae was identified to be with members of the family Enterobacteriacea, for example the protein cNuc (GenBank entry KZ082453.1; SEQ ID NO: 10) was found in the genome of Escherichia coli and exhibited 67.3% protein identity in comparison with P.vNuc (without hypothetical signal peptides). The hypothetical protein 7% Nuc (NCBI entry WP_039390287.1; SEQ ID NO: 11) from Pantoea agglomermns exhibited 57.0% protein identity in comparison with P.vNuc (SEQ ID NO:2). Comparisons were done as described in example 1.

Example 16: Determination of Kinetic Parameters of Purified Recombinant EcNuc and PaNuc Proteins P.vNuc homologues EcNuc (SEQ ID NO:8) and the distantly related PaNuc (SEQ ID NO:9) were produced in recombinant form without the predicted signal sequences and purified according to examples 2, 4, and 5. Enzymatic characterizations and determination of kinetic properties were done as described in examples 7 and 14. PaNuc showed NSN activity in a pH range between about 5.0 (13% NSN activity) and about 9.0 (42% NSN activity) with its maximum activity at about pH 7.0 (100% NSN activity) and in a temperature range between about 10° C. (2% NSN activity) and about 80° C. (55% NSN activity) with its maximum activity at about 70° C. (100% NSN activity). PaNuc did not show NSN activity at about 4° C. (0% NSN activity). EcNuc showed NSN activity in a pH range between about 5.0 (81% NSN activity) and about 8.0 (22% NSN activity) with its maximum activity at about pH 6.0 (100% NSN activity) and in a temperature range between about 10° C. (2% NSN activity) and about 60° C. (16% NSN activity) with its maximum activity at about 40° C. (100% NSN activity). EcNuc did not show NSN activity at about 4° C. (0% NSN activity). To compare catalytic rate constants $k_{cat}$ of P.vNuc, PaNuc, and EcNuc, enzyme kinetics were determined at about 25° C. (Table 4) as described in example 14. The $k_{cat}$ of PaNuc is about 6%, and the $k_{cat}$ value of EcNuc is about 35% of the $k_{cat}$ value of P.vNuc, demonstrating the high catalytic NSN activity of P.vNuc compared to related nucleases. Importantly, only P.vNuc has NSN activity at about 4° C.

TABLE 4

$k_{cat}$ values of purified recombinant P.vNuc, PaNuc, and EcNuc proteins at about 25° C.

| Protein | SEQ ID NO: | $k_{cat}$ (s$^{-1}$) |
|---|---|---|
| PsNuc | 2 | 1,756 |
| PaNuc | 8 | 114 |
| EcNuc | 9 | 614 |

The invention claimed is:

1. A method of preparing a cell suspension, comprising:
 (a) obtaining a recombinant nuclease,
 (b) incubating the cell suspension with the recombinant nuclease until nucleic acids present in the suspension and/or released from cells are removed, and then
 (c) flowing the cells through a microfluidic channel;
 wherein the recombinant nuclease comprises an amino acid sequence that is at least 90% identical to the amino acid sequence set forth in SEQ ID NO:2,
 wherein the recombinant nuclease when present in a solution at 4° C. has non-specific nuclease (NSN) activity with a $k_{cat}$ value of at least 10 s$^{-1}$, and
 wherein removing nucleic acids from the suspension in step (b) prevents nucleic acids from clogging the microfluidic channel in step (c).

2. The method of claim 1, wherein said microfluidic channel is part of a cell sorting apparatus.

3. The method of claim 1, wherein the amino acid sequence of the nuclease comprises at least one amino acid substitution, addition, or deletion compared with the amino acid sequence set forth in SEQ ID NO:2 wherein the nuclease has increased NSN activity compared with a nuclease having an amino acid sequence consisting of SEQ ID NO:2.

4. The method of claim 1, wherein the incubating is performed at a temperature between 0° C. and 10° C.

5. The method of claim 1, wherein the NSN activity has a $k_{cat}$ value of at least 200 s$^{-1}$.

6. The method of claim 1, wherein incubating is performed at a pH of 7 to 8.

7. The method of claim 1, wherein the amino acid sequence of the nuclease comprises the amino acid sequence set forth in SEQ ID NO:3 or in SEQ ID NO:6.

8. A method of preparing a cell suspension, comprising:
 (a) obtaining a recombinant nuclease, and
 (b) incubating the cell suspension with the recombinant nuclease until nucleic acids present in the suspension and/or released from cells are removed, thereby facilitating flow of the cells through a microfluidic channel;
 wherein the recombinant nuclease contains an amino acid sequence that is at least 90% identical to the amino acid sequence set forth in SEQ ID NO:2, and
 wherein the recombinant nuclease when present in a solution at 4° C. has non-specific nuclease (NSN) activity with a $k_{cat}$ value of at least 100 s$^{-1}$.

9. A method of preparing a cell suspension, comprising:
 (a) obtaining a recombinant nuclease, and
 (b) incubating the cell suspension with the recombinant nuclease until nucleic acids present in the suspension and/or released from cells are removed, thereby facilitating flow of the cells through a microfluidic channel;
 wherein the recombinant nuclease contains an amino acid sequence that is at least 90% identical to the amino acid sequence set forth in SEQ ID NO:2;
 wherein the recombinant nuclease when present in a solution at 4° C. has non-specific nuclease (NSN) activity with a $k_{cat}$ value of at least 10 s$^{-1}$; and
 wherein the method further comprises complexing cations that are present in the cell suspension before or during step (b).

10. The method of claim 9, wherein cations in the suspension are complexed by adding a cation complexing agent to the cell suspension at a concentration between 0.1 mM and 20 mM.

11. The method of claim 10, wherein the cation complexing agent is EDTA (ethylenediaminetetraacetic acid).

12. The method of claim 10, wherein the cation complexing agent is selected from the group consisting of EGTA (ethylene glycol-bis(2-aminoethylether)-N,N,N',N'-tetraacetic acid), DOTA (1,4,7,10 tetraazacyclododecane-1,4,7,10 tetraacetic acid), DTPA (diethylenetriaminepentaacetic acid), MGDA (methylglycine N,N-diacetic acid), GLDA (glutamate diacetate), NTA (nitrilotriacetic acid), IDS (iminodisuccinate), HEEDTA (N-(2-hydroxyethyl)ethylenediamine-N,N',N' triacetic acid), STPP (sodium tripolyphosphate), TTHA (triethylenetetramine-N,N,N',N'',N''',N'''-hexaacetic acid), phosphonates, DFOA (desferrioxamine), DMSA (2,3 di-mercaptosuccinic acid), penicillamine, and dimercaprol.

13. A kit for facilitating flow of cells in a suspension through a microfluidic channel and/or to prepare cells in a suspension for cell sorting, wherein the kit comprises:
 (i) a reagent solution that comprises a recombinant nuclease and a non-naturally occurring cation complexing agent,
 wherein the nuclease comprises an amino acid sequence that is at least 90% identical to the amino acid sequence set forth in SEQ ID NO:2,
 wherein the nuclease has non-specific nuclease (NSN) activity in the reagent solution at 4° C. has a $k_{cat}$ value of at least 100 s$^{-1}$, and
 (ii) instructions for using the solution for removing nucleic acids from the cell suspension to facilitate flow of the cells through the microfluidic channel;
 wherein the amount and concentration of the recombinant nuclease in the solution is effective for degrading and removing nucleic acids from the cell suspension when combined and incubated at a temperature between 0° C. and 10° C.

14. The kit of claim 13, wherein the non-naturally occurring cation complexing agent is present in the reagent solution at a concentration between 0.1 mM and 50 mM.

15. A method of preparing a cell suspension, the method comprising:

(a) obtaining the kit of claim 13;
(b) incubating the cell suspension with the reagent solution from the kit at a temperature between 0° C. and 10° C. until nucleic acids present in the suspension and/or released from the cells are removed.

\* \* \* \* \*

SEQUENCE LISTING

<160> NUMBER OF SEQ ID NOS: 71

<210> SEQ ID NO 1
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthesized

<400> SEQUENCE: 1

```
Met Thr Ala Leu Ser Ala Leu Thr Arg Ser Leu Ser Arg Gly Leu Val
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
                100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180
```

<210> SEQ ID NO 2
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthesized

<400> SEQUENCE: 2

```
Ala Glu Ile Gln Val Gly Phe Ser Pro Glu Gly Ser Ala Glu Gln Leu
1               5                   10                  15

Val Leu Asn Val Ile Gln Arg Ala Arg Gln Gln Ile Arg Leu Met Ala
                20                  25                  30

Tyr Ser Phe Thr Ser Pro Ser Val Val Lys Ala Leu Val Gln Ala Lys
            35                  40                  45

Arg Arg Gly Val Asp Val Gln Val Val Asp Ala His Gly Asn Asp
    50                  55                  60

Asn Arg Ala Ser Arg Ala Ala Met Asn Leu Leu Ala Asn Ala Gln Ile
65                  70                  75                  80
```

```
Pro Val Arg Thr Asn Gly Ala Tyr Lys Ile Gln His Asp Lys Val Ile
            85                  90                  95

Ile Thr Asp Gly Gln Asn Val Glu Thr Gly Ser Phe Asn Tyr Ser Ala
        100                 105                 110

Ser Ala Ala Lys Ala Asn Ser Glu Asn Ala Val Val Met Trp Asp Val
        115                 120                 125

Pro Ala Val Ala Ser Val Tyr Leu Glu His Trp Gln Ser Arg Trp Val
        130                 135                 140

Gln Gly Gln Pro Tyr Gln Pro Thr Tyr
145                 150

<210> SEQ ID NO 3
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthesized

<400> SEQUENCE: 3

Ala Glu Ile Gln Val Gly Phe Ser Pro Glu Gly Ser Ala Glu Gln Leu
1               5                   10                  15

Val Leu Asn Val Ile Gln Gly Ala Arg Gln Gln Ile Arg Leu Met Ala
            20                  25                  30

Tyr Ser Phe Thr Ser Pro Ser Val Val Lys Ala Leu Val Gln Ala Lys
        35                  40                  45

Arg Arg Gly Val Asp Val Gln Val Val Val Asp Ala His Gly Asn Asp
    50                  55                  60

Asn Arg Ala Ser Arg Ala Ala Met Asn Leu Leu Ala Asn Ala Gln Ile
65                  70                  75                  80

Pro Val Arg Thr Asn Gly Ala Tyr Lys Ile Gln His Asp Lys Val Ile
            85                  90                  95

Ile Thr Asp Gly Gln Asn Val Glu Thr Gly Ser Phe Asn Tyr Ser Ala
        100                 105                 110

Ser Ala Ala Lys Ala Asn Ser Glu Asn Ala Val Val Met Trp Asp Val
        115                 120                 125

Pro Ala Val Ala Ser Val Tyr Leu Glu His Trp Gln Ser Arg Trp Val
        130                 135                 140

Gln Gly Gln Pro Tyr Gln Pro Thr Tyr
145                 150

<210> SEQ ID NO 4
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: synthesized

<400> SEQUENCE: 4

Ala Glu Ile Gln Val Gly Phe Ser Pro Glu Gly Ser Ala Glu Gln Leu
1               5                   10                  15

Val Leu Asn Val Ile Gln Arg Ala Arg Gln Gln Ile Arg Leu Met Ala
            20                  25                  30

Tyr Ser Phe Thr Ser Pro Ser Val Val Lys Ala Leu Val Gln Ala Lys
        35                  40                  45
```

```
Arg Arg Gly Val Asp Val Gln Val Val Asp Ala His Gly Asn Asp
         50                  55                  60

Ser Arg Ala Ser Arg Ala Ala Met Asn Leu Leu Ala Asn Ala Gln Ile
 65                  70                  75                  80

Pro Val Arg Thr Asn Gly Ala Tyr Lys Ile Gln His Asp Lys Val Ile
                 85                  90                  95

Ile Thr Asp Gly Gln Asn Val Glu Thr Gly Ser Phe Asn Tyr Ser Ala
                100                 105                 110

Ser Ala Ala Lys Ala Asn Ser Glu Asn Ala Val Val Met Trp Asp Val
            115                 120                 125

Pro Ala Val Ala Ser Val Tyr Leu Glu His Trp Gln Ser Arg Trp Val
        130                 135                 140

Gln Gly Gln Pro Tyr Gln Pro Thr Tyr
145                 150

<210> SEQ ID NO 5
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of mature PsNuc_Gly116Ala

<400> SEQUENCE: 5

Ala Glu Ile Gln Val Gly Phe Ser Pro Glu Gly Ser Ala Glu Gln Leu
 1               5                  10                  15

Val Leu Asn Val Ile Gln Arg Ala Arg Gln Gln Ile Arg Leu Met Ala
                20                  25                  30

Tyr Ser Phe Thr Ser Pro Ser Val Val Lys Ala Leu Val Gln Ala Lys
             35                  40                  45

Arg Arg Gly Val Asp Val Gln Val Val Asp Ala His Gly Asn Asp
         50                  55                  60

Asn Arg Ala Ser Arg Ala Ala Met Asn Leu Leu Ala Asn Ala Gln Ile
 65                  70                  75                  80

Pro Val Arg Thr Asn Ala Ala Tyr Lys Ile Gln His Asp Lys Val Ile
                 85                  90                  95

Ile Thr Asp Gly Gln Asn Val Glu Thr Gly Ser Phe Asn Tyr Ser Ala
                100                 105                 110

Ser Ala Ala Lys Ala Asn Ser Glu Asn Ala Val Val Met Trp Asp Val
            115                 120                 125

Pro Ala Val Ala Ser Val Tyr Leu Glu His Trp Gln Ser Arg Trp Val
        130                 135                 140

Gln Gly Gln Pro Tyr Gln Pro Thr Tyr
145                 150

<210> SEQ ID NO 6
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of mature PsNuc_Asp157Gly

<400> SEQUENCE: 6

Ala Glu Ile Gln Val Gly Phe Ser Pro Glu Gly Ser Ala Glu Gln Leu
```

```
                1               5                      10                      15
            Val Leu Asn Val Ile Gln Arg Ala Arg Gln Gln Ile Arg Leu Met Ala
                           20                      25                      30

Tyr Ser Phe Thr Ser Pro Ser Val Val Lys Ala Leu Val Gln Ala Lys
                           35                      40                      45

Arg Arg Gly Val Asp Val Gln Val Val Val Asp Ala His Gly Asn Asp
             50                      55                      60

Asn Arg Ala Ser Arg Ala Ala Met Asn Leu Leu Ala Asn Ala Gln Ile
             65                      70                      75                      80

Pro Val Arg Thr Asn Gly Ala Tyr Lys Ile Gln His Asp Lys Val Ile
                           85                      90                      95

Ile Thr Asp Gly Gln Asn Val Glu Thr Gly Ser Phe Asn Tyr Ser Ala
                          100                     105                     110

Ser Ala Ala Lys Ala Asn Ser Glu Asn Ala Val Val Met Trp Gly Val
                          115                     120                     125

Pro Ala Val Ala Ser Val Tyr Leu Glu His Trp Gln Ser Arg Trp Val
                          130                     135                     140

Gln Gly Gln Pro Tyr Gln Pro Thr Tyr
            145                     150

<210> SEQ ID NO 7
<211> LENGTH: 177
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of StNuc including the signal
      peptide

<400> SEQUENCE: 7

Met Lys Lys Leu Ala Thr Trp Leu Leu Ala Ala Ala Phe Thr Thr Ala
             1               5                      10                      15

Ala Leu Pro Ala Phe Ala Val Glu Pro Ser Val Gln Val Gly Tyr Ser
                           20                      25                      30

Pro Glu Gly Ser Ala Arg Val Leu Val Leu Ser Ala Ile Asp Ser Ala
                           35                      40                      45

Lys Thr Ser Ile Arg Met Met Ala Tyr Ser Phe Thr Ala Pro Asp Ile
             50                      55                      60

Met Lys Ala Leu Val Ala Ala Lys Lys Arg Gly Val Asp Val Lys Ile
             65                      70                      75                      80

Val Ile Asp Glu Arg Gly Asn Thr Gly Arg Ala Ser Ile Ala Ala Met
                           85                      90                      95

Asn Tyr Ile Ala Asn Ser Gly Ile Pro Leu Arg Thr Asp Ser Asn Phe
                          100                     105                     110

Pro Ile Gln His Asp Lys Val Ile Val Asp Asn Val Thr Val Glu
                          115                     120                     125

Thr Gly Ser Phe Asn Phe Thr Lys Ala Ala Glu Thr Lys Asn Ser Glu
                          130                     135                     140

Asn Ala Val Val Ile Trp Asn Met Pro Lys Leu Ala Glu Ser Phe Leu
            145                     150                     155                     160

Glu His Trp Gln Asp Arg Trp Asn Gln Gly Arg Asp Tyr Arg Ser Ser
                          165                     170                     175

Tyr
```

```
<210> SEQ ID NO 8
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of mature EcNuc

<400> SEQUENCE: 8
```

Ala Ser Ala Gln Val Gly Phe Ser Pro Glu Gly Thr Ala Gln Gln Leu
1               5                   10                  15

Val Ile Asn Val Ile Gly Ser Ala Lys Asp Asn Ile Arg Met Met Ala
            20                  25                  30

Tyr Ser Phe Thr Ala Pro Asp Ile Met Lys Ala Leu Ile Ala Ala Lys
        35                  40                  45

Arg Arg Gly Val Asp Val Lys Ile Val Val Asp Glu Asn Gly Asn Thr
    50                  55                  60

Gly Arg Ala Ser Arg Ala Ala Met Asn Leu Val Thr Asn Ala Gly Ile
65                  70                  75                  80

Pro Leu Arg Val Asn Ser Asn Tyr Lys Ile Gln His Asp Lys Val Ile
                85                  90                  95

Ile Val Asp Gly Arg His Val Glu Thr Gly Ser Phe Asn Tyr Thr Ala
            100                 105                 110

Ser Ala Glu Lys Tyr Asn Ser Glu Asn Ala Ile Val Met Trp Asp Ala
        115                 120                 125

Pro Glu Leu Ala Gly Gln Tyr Leu Lys His Trp Gln Ser Arg Trp Asn
    130                 135                 140

Gln Gly Arg Asp Phe Thr Pro Ser Tyr
145                 150

```
<210> SEQ ID NO 9
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of mature PaNuc

<400> SEQUENCE: 9
```

Ser Gly Ala Pro Gly Val Ser Val Gly Phe Ser Pro Glu Gly Ser Ala
1               5                   10                  15

Glu Ala Leu Val Leu Gly Val Ile Asp Arg Ala Lys Ala Glu Ile Arg
            20                  25                  30

Leu Ala Gly Tyr Ser Phe Thr Ser Pro Asp Val Ala Thr Ala Leu Val
        35                  40                  45

Arg Ala Lys Ala Arg Gly Val Asp Val Arg Val Leu Asp Glu Lys
    50                  55                  60

Ala Asn Gln Asn Arg Lys Ser Gln Val Ala Ile Asn Val Leu Thr Ala
65                  70                  75                  80

Arg Asp Ile Pro Val Arg Leu Asn Gly Arg Tyr Ala Ala Leu His Asp
                85                  90                  95

Lys Phe Ile Ile Ala Asp Gly Arg Thr Val Glu Thr Gly Ser Val Asn
            100                 105                 110

Tyr Thr Arg Ala Gly Ala Arg Tyr Asn Ser Glu Asn Ala Leu Val Ile
        115                 120                 125

```
Glu Gly Met Pro Glu Leu Ala Asp Arg Tyr Leu Gln His Trp Gln Ser
            130                 135                 140

Arg Trp Asp Ala Gly Thr Asp Tyr Arg Leu Pro Tyr
145                 150                 155

<210> SEQ ID NO 10
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of EcNuc including the signal
      peptide

<400> SEQUENCE: 10

Met Val Ala Ala Val Leu Tyr Gly Ala Ser Ala Pro Ser Leu Phe Ala
1               5                   10                  15

Ala Ser Ala Gln Val Gly Phe Ser Pro Glu Gly Thr Ala Gln Gln Leu
            20                  25                  30

Val Ile Asn Val Ile Gly Ser Ala Lys Asp Asn Ile Arg Met Met Ala
            35                  40                  45

Tyr Ser Phe Thr Ala Pro Asp Ile Met Lys Ala Leu Ile Ala Ala Lys
    50                  55                  60

Arg Arg Gly Val Asp Val Lys Ile Val Val Asp Glu Asn Gly Asn Thr
65                  70                  75                  80

Gly Arg Ala Ser Arg Ala Ala Met Asn Leu Val Thr Asn Ala Gly Ile
                85                  90                  95

Pro Leu Arg Val Asn Ser Asn Tyr Lys Ile Gln His Asp Lys Val Ile
            100                 105                 110

Ile Val Asp Gly Arg His Val Glu Thr Gly Ser Phe Asn Tyr Thr Ala
            115                 120                 125

Ser Ala Glu Lys Tyr Asn Ser Glu Asn Ala Ile Val Met Trp Asp Ala
        130                 135                 140

Pro Glu Leu Ala Gly Gln Tyr Leu Lys His Trp Gln Ser Arg Trp Asn
145                 150                 155                 160

Gln Gly Arg Asp Phe Thr Pro Ser Tyr
                165

<210> SEQ ID NO 11
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: protein sequence of PaNuc including the signal
      peptide

<400> SEQUENCE: 11

Met Lys Val Ile Leu Val Pro Leu Leu Leu Ser Ser Leu Thr Leu Leu
1               5                   10                  15

Ser Pro Ala Gly His Ala Ser Gly Ala Pro Gly Val Ser Val Gly Phe
            20                  25                  30

Ser Pro Glu Gly Ser Ala Glu Ala Leu Val Leu Gly Val Ile Asp Arg
        35                  40                  45

Ala Lys Ala Glu Ile Arg Leu Ala Gly Tyr Ser Phe Thr Ser Pro Asp
    50                  55                  60
```

```
Val Ala Thr Ala Leu Val Arg Ala Lys Ala Arg Gly Val Asp Val Arg
 65                  70                  75                  80

Val Val Leu Asp Glu Lys Ala Asn Gln Asn Arg Lys Ser Gln Val Ala
                 85                  90                  95

Ile Asn Val Leu Thr Ala Arg Asp Ile Pro Val Arg Leu Asn Gly Arg
            100                 105                 110

Tyr Ala Ala Leu His Asp Lys Phe Ile Ile Ala Asp Gly Arg Thr Val
            115                 120                 125

Glu Thr Gly Ser Val Asn Tyr Thr Arg Ala Gly Ala Arg Tyr Asn Ser
        130                 135                 140

Glu Asn Ala Leu Val Ile Glu Gly Met Pro Glu Leu Ala Asp Arg Tyr
145                 150                 155                 160

Leu Gln His Trp Gln Ser Arg Trp Asp Ala Gly Thr Asp Tyr Arg Leu
                165                 170                 175

Pro Tyr

<210> SEQ ID NO 12
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 12

Met Thr Ala Leu Ser Ala Leu Thr Arg Ser Leu Ser Arg Gly Leu Val
 1               5                  10                  15

Ala Ser Val Leu Leu Cys Asn Leu Thr Phe Thr Val Gln Ala Ala Glu
             20                  25                  30

Ile Gln Val Gly Phe Ser Pro Glu Gly Ser Ala Glu Gln Leu Val Leu
         35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
                 85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 13
<211> LENGTH: 183
<212> TYPE: PRT
<213> ORGANISM: Unknown
<220> FEATURE:
<223> OTHER INFORMATION: Description of Unknown:
      Pseudomonas syringae group sequence
```

<400> SEQUENCE: 13

Met Thr Ala Leu Ser Ala Leu Thr Arg Ser Leu Ser Arg Gly Leu Leu
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 14
<211> LENGTH: 183
<212> TYPE: PRT
<213> ORGANISM: Unknown
<220> FEATURE:
<223> OTHER INFORMATION: Description of Unknown:
      Pseudomonas syringae group genomosp. 2 sequence

<400> SEQUENCE: 14

Met Thr Ala Leu Ser Ala Leu Thr Arg Pro Leu Ser Arg Gly Leu Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

-continued

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 15
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 15

Met Thr Ala Leu Ser Ala Leu Thr Arg Pro Leu Ser Arg Gly Leu Leu
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
                100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 16
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 16

Met Thr Ala Leu Ser Ala Leu Thr Arg Pro Leu Ser Arg Gly Leu Leu
1               5                   10                  15

Ala Ser Val Leu Leu Cys Asn Leu Ser Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

```
Gly Val Asp Val Gln Val Val Asp Ala His Gly Asn Asp Asn Arg
            85                  90                  95

Ala Ser Arg Ala Ala Met Asn Leu Leu Ala Asn Ala Gln Ile Pro Val
        100                 105                 110

Arg Thr Asn Gly Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 17
<211> LENGTH: 168
<212> TYPE: PRT
<213> ORGANISM: Pseudomonas amygdali

<400> SEQUENCE: 17

Met Ala Leu Val Leu Leu Cys Asn Leu Thr Phe Thr Val Gln Ala Ala
1               5                   10                  15

Glu Ile Gln Val Gly Phe Ser Pro Glu Gly Ser Ala Glu Gln Leu Val
            20                  25                  30

Leu Asn Val Ile Gln Arg Ala Arg Gln Gln Ile Arg Leu Met Ala Tyr
        35                  40                  45

Ser Phe Thr Ser Pro Ser Val Val Lys Ala Leu Val Gln Ala Lys Arg
    50                  55                  60

Arg Gly Val Asp Val Gln Val Val Asp Ala His Gly Asn Asp Asn
65                  70                  75                  80

Arg Ala Ser Arg Ala Ala Met Asn Leu Leu Ala Asn Ala Gln Ile Pro
                85                  90                  95

Val Arg Thr Asn Gly Ala Tyr Lys Ile Gln His Asp Lys Val Ile Ile
            100                 105                 110

Thr Asp Gly Gln Asn Val Glu Thr Gly Ser Phe Asn Tyr Ser Ala Ser
        115                 120                 125

Ala Ala Lys Ala Asn Ser Glu Asn Ala Val Val Met Trp Asp Val Pro
    130                 135                 140

Ala Val Ala Ser Val Tyr Leu Glu His Trp Gln Ser Arg Trp Val Gln
145                 150                 155                 160

Gly Gln Pro Tyr Gln Pro Thr Tyr
                165

<210> SEQ ID NO 18
<211> LENGTH: 166
<212> TYPE: PRT
<213> ORGANISM: Pseudomonas savastanoi

<400> SEQUENCE: 18

Met Val Leu Leu Cys Asn Leu Thr Phe Thr Val Gln Ala Ala Glu Ile
1               5                   10                  15

Gln Val Gly Phe Ser Pro Glu Gly Ser Ala Glu Gln Leu Val Leu Asn
            20                  25                  30

Val Ile Gln Arg Ala Arg Gln Gln Ile Arg Leu Met Ala Tyr Ser Phe
        35                  40                  45
```

-continued

Thr Ser Pro Ser Val Val Lys Ala Leu Val Gln Ala Lys Arg Arg Gly
    50                  55                  60

Val Asp Val Gln Val Val Asp Ala His Gly Asn Asp Asn Arg Ala
65                  70                  75                  80

Ser Arg Ala Ala Met Asn Leu Leu Ala Asn Ala Gln Ile Pro Val Arg
                85                  90                  95

Thr Asn Gly Ala Tyr Lys Ile Gln His Asp Lys Val Ile Ile Thr Asp
            100                 105                 110

Gly Gln Asn Val Glu Thr Gly Ser Phe Asn Tyr Ser Ala Ser Ala Ala
        115                 120                 125

Lys Ala Asn Ser Glu Asn Ala Val Val Met Trp Asp Val Pro Ala Val
    130                 135                 140

Ala Ser Val Tyr Leu Glu His Trp Gln Ser Arg Trp Val Gln Gly Gln
145                 150                 155                 160

Pro Tyr Gln Pro Thr Tyr
            165

<210> SEQ ID NO 19
<211> LENGTH: 165
<212> TYPE: PRT
<213> ORGANISM: Pseudomonas syringae

<400> SEQUENCE: 19

Met Leu Leu Cys Asn Leu Thr Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
    50                  55                  60

Asp Val Gln Val Val Asp Ala His Gly Asn Asp Asn Arg Ala Ser
65                  70                  75                  80

Arg Ala Ala Met Asn Leu Leu Ala Asn Ala Gln Ile Pro Val Arg Thr
                85                  90                  95

Asn Gly Ala Tyr Lys Ile Gln His Asp Lys Val Ile Ile Thr Asp Gly
            100                 105                 110

Gln Asn Val Glu Thr Gly Ser Phe Asn Tyr Ser Ala Ser Ala Ala Lys
        115                 120                 125

Ala Asn Ser Glu Asn Ala Val Val Met Trp Asp Val Pro Ala Val Ala
    130                 135                 140

Ser Val Tyr Leu Glu His Trp Gln Ser Arg Trp Val Gln Gly Gln Pro
145                 150                 155                 160

Tyr Gln Pro Thr Tyr
            165

<210> SEQ ID NO 20
<211> LENGTH: 158
<212> TYPE: PRT
<213> ORGANISM: Pseudomonas savastanoi pv. glycinea str. race 4

<400> SEQUENCE: 20

Phe Thr Val Gln Ala Ala Glu Ile Gln Val Gly Phe Ser Pro Glu Gly
1               5                   10                  15

Ser Ala Glu Gln Leu Val Leu Asn Val Ile Gln Arg Ala Arg Gln Gln
            20                  25                  30

```
Ile Arg Leu Met Ala Tyr Ser Phe Thr Ser Pro Ser Val Val Lys Ala
            35                  40                  45

Leu Val Gln Ala Lys Arg Arg Gly Val Asp Val Gln Val Val Val Asp
 50                  55                  60

Ala His Gly Asn Asp Asn Arg Ala Ser Arg Ala Ala Met Asn Leu Leu
 65                  70                  75                  80

Ala Asn Ala Gln Ile Pro Val Arg Thr Asn Gly Ala Tyr Lys Ile Gln
                85                  90                  95

His Asp Lys Val Ile Ile Thr Asp Gly Gln Asn Val Glu Thr Gly Ser
            100                 105                 110

Phe Asn Tyr Ser Ala Ser Ala Lys Ala Asn Ser Glu Asn Ala Val
            115                 120                 125

Val Met Trp Asp Val Pro Ala Val Ala Ser Val Tyr Leu Glu His Trp
130                 135                 140

Gln Ser Arg Trp Val Gln Gly Gln Pro Tyr Gln Pro Thr Tyr
145                 150                 155
```

<210> SEQ ID NO 21
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 21

```
Met Thr Ala Leu Ser Ala Leu Thr Arg Ser Leu Ser Arg Gly Leu Val
 1               5                  10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Phe Ser Ala Ser Ala
130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180
```

<210> SEQ ID NO 22
<211> LENGTH: 183
<212> TYPE: PRT
<213> ORGANISM: Pseudomonas syringae

<400> SEQUENCE: 22

Met Thr Ala Leu Ser Ala Leu Thr Arg Ser Leu Ser Arg Gly Leu Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Glu Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 23
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 23

Met Thr Ala Leu Ser Ala Leu Thr Arg Thr Leu Ser Arg Gly Leu Leu
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Leu Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 24
<211> LENGTH: 168
<212> TYPE: PRT
<213> ORGANISM: Pseudomonas syringae

<400> SEQUENCE: 24

Met Ala Ser Val Leu Leu Cys Asn Leu Thr Phe Thr Val Gln Ala Ala
1               5                   10                  15

Glu Ile Gln Val Gly Phe Ser Pro Glu Gly Ser Ala Glu Gln Leu Val
            20                  25                  30

Leu Asn Val Ile Gln Arg Ala Arg Gln Gln Ile Arg Leu Met Ala Tyr
        35                  40                  45

Ser Phe Thr Ser Pro Ser Val Val Lys Ala Leu Val Gln Ala Lys Arg
    50                  55                  60

Arg Gly Val Asp Val Gln Val Val Asp Ala His Gly Asn Asp Asn
65                  70                  75                  80

Arg Ala Ser Arg Ala Ala Met Asn Leu Leu Ala Asn Ala Gln Ile Pro
                85                  90                  95

Val Arg Thr Asn Gly Ala Tyr Lys Ile Gln His Asp Lys Val Ile Ile
            100                 105                 110

Thr Asp Gly Gln Asn Val Glu Thr Gly Ser Phe Asn Phe Ser Ala Ser
        115                 120                 125

Ala Ala Lys Ala Asn Ser Glu Asn Ala Val Val Met Trp Asp Val Pro
    130                 135                 140

Ala Val Ala Ser Val Tyr Leu Glu His Trp Gln Ser Arg Trp Val Gln
145                 150                 155                 160

Gly Gln Pro Tyr Gln Pro Thr Tyr
                165

<210> SEQ ID NO 25
<211> LENGTH: 165
<212> TYPE: PRT
<213> ORGANISM: Pseudomonas amygdali

<400> SEQUENCE: 25

Met Leu Leu Cys Asn Leu Thr Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
    50                  55                  60

Asp Val Gln Val Val Asp Ala His Gly Asn Asp Asn Arg Ala Ser
65                  70                  75                  80

Arg Ala Ala Met Asn Leu Leu Ala Asn Ala Gln Ile Pro Val Arg Thr
                85                  90                  95

Asn Gly Ala Tyr Lys Ile Gln His Asp Lys Val Ile Ile Thr Asp Gly
            100                 105                 110

Gln Asn Val Glu Thr Gly Ser Phe Asn Phe Ser Ala Ser Ala Ala Lys
        115                 120                 125

Ala Asn Ser Glu Asn Ala Val Val Met Trp Asp Val Pro Ala Val Ala
    130                 135                 140

Ser Val Tyr Leu Glu His Trp Gln Ser Arg Trp Val Gln Gly Gln Pro
145                 150                 155                 160

Tyr Gln Pro Thr Tyr
                165

<210> SEQ ID NO 26
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 26

Met Thr Ala Leu Ser Ala Leu Thr Arg Pro Leu Ser Arg Gly Leu Leu
1               5                   10                  15

Ala Ser Val Leu Leu Cys Asn Leu Ser Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Phe Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 27
<211> LENGTH: 183
<212> TYPE: PRT
<213> ORGANISM: Pseudomonas savastanoi

<400> SEQUENCE: 27

Met Thr Ala Leu Ser Ala Leu Thr Arg Ser Leu Ser Arg Gly Leu Val
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

```
Ala Ser Arg Ala Ala Met Asn Leu Leu Ala Asn Ala Gln Ile Pro Val
            100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
            130                 135                 140

Ala Lys Ala Asn Ser Glu Asn Ala Val Val Met Trp Asp Val Pro Ala
145                 150                 155                 160

Glu Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 28
<211> LENGTH: 183
<212> TYPE: PRT
<213> ORGANISM: Unknown
<220> FEATURE:
<223> OTHER INFORMATION: Description of Unknown:
      Pseudomonas syringae group genomosp. 3 sequence

<400> SEQUENCE: 28

Met Thr Ala Leu Ser Ala Leu Thr Arg Pro Leu Ser Arg Gly Leu Leu
1               5                   10                  15

Ala Ser Val Leu Leu Cys Asn Leu Ser Phe Thr Val Gln Ala Ala Glu
            20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
        50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
            85                  90                  95

Ala Ser Arg Ala Ala Met Asn Leu Leu Ala Asn Ala Gln Ile Pro Val
            100                 105                 110

Arg Thr Asn Gly Val Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
            130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 29
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 29

Met Thr Ala Leu Ser Ala Leu Thr Arg Pro Leu Ser Arg Gly Leu Val
1               5                   10                  15
```

Ala Ser Val Leu Leu Cys Asn Leu Thr Phe Thr Val Gln Ala Ala Glu
             20                  25                  30

Ile Gln Val Gly Phe Ser Pro Glu Gly Ser Ala Glu Gln Leu Val Leu
         35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
             85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 30
<211> LENGTH: 183
<212> TYPE: PRT
<213> ORGANISM: Pseudomonas amygdali

<400> SEQUENCE: 30

Met Thr Ala Leu Ser Ala Leu Thr Arg Pro Phe Ser Arg Gly Leu Val
1               5                   10                  15

Ala Ser Val Leu Leu Cys Asn Leu Thr Phe Thr Val Gln Ala Ala Glu
             20                  25                  30

Ile Gln Val Gly Phe Ser Pro Glu Gly Ser Ala Glu Gln Leu Val Leu
         35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
             85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

```
<210> SEQ ID NO 31
<211> LENGTH: 183
<212> TYPE: PRT
<213> ORGANISM: Unknown
<220> FEATURE:
<223> OTHER INFORMATION: Description of Unknown:
      Pseudomonas syringae group genomosp. 2 sequence

<400> SEQUENCE: 31

Met Thr Ala Leu Ser Ala Leu Thr Arg Pro Leu Ser Arg Gly Leu Leu
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 32
<211> LENGTH: 165
<212> TYPE: PRT
<213> ORGANISM: Pseudomonas syringae

<400> SEQUENCE: 32

Met Leu Leu Cys Asn Leu Thr Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
    50                  55                  60

Asp Val Gln Val Val Asp Ala His Gly Asn Asp Asn Arg Ala Ser
65                  70                  75                  80

Arg Ala Ala Met Asn Leu Leu Ala Asn Ala Gln Ile Pro Val Arg Thr
            85                  90                  95

Asn Gly Ala Tyr Lys Ile Gln His Asp Lys Val Ile Ile Thr Asp Gly
        100                 105                 110

Gln Asn Val Glu Thr Gly Ser Phe Asn Tyr Ser Ala Ser Ala Ala Lys
    115                 120                 125

Ala Asn Ser Glu Asn Ala Val Val Met Trp Glu Val Pro Ala Val Ala
```

```
                130                 135                 140
Ser Val Tyr Leu Glu His Trp Gln Ser Arg Trp Val Gln Gly Gln Pro
145                 150                 155                 160

Tyr Gln Pro Thr Tyr
                165

<210> SEQ ID NO 33
<211> LENGTH: 169
<212> TYPE: PRT
<213> ORGANISM: Pseudomonas coronafaciens

<400> SEQUENCE: 33

Met Val Ala Ser Val Leu Leu Cys Asn Leu Thr Phe Thr Val Gln Ala
1               5                   10                  15

Ala Glu Ile Gln Val Gly Phe Ser Pro Glu Gly Ser Ala Glu Gln Leu
                20                  25                  30

Val Leu Asn Val Ile Gln Arg Ala Arg Gln Gln Ile Arg Leu Met Ala
            35                  40                  45

Tyr Ser Phe Thr Ser Pro Ser Val Val Lys Ala Leu Val Gln Ala Lys
    50                  55                  60

Arg Arg Gly Val Asp Val Gln Val Val Val Asp Ala His Gly Asn Asp
65                  70                  75                  80

Asn Arg Ala Ser Arg Ala Ala Met Asn Leu Leu Ala Asn Ala Gln Ile
                85                  90                  95

Pro Val Arg Thr Asn Ala Ala Tyr Lys Ile Gln His Asp Lys Val Ile
            100                 105                 110

Ile Thr Asp Gly Gln Asn Val Glu Thr Gly Ser Phe Asn Tyr Ser Ala
        115                 120                 125

Ser Ala Ala Lys Ala Asn Ser Glu Asn Ala Val Val Met Trp Asp Val
    130                 135                 140

Pro Ala Val Ala Ser Val Tyr Leu Glu His Trp Gln Ser Arg Trp Val
145                 150                 155                 160

Gln Gly Gln Pro Tyr Gln Pro Thr Tyr
                165

<210> SEQ ID NO 34
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 34

Met Thr Ala Leu Ser Ala Leu Thr Arg Pro Leu Ser Arg Gly Leu Leu
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Val Asp Ala His Gly Asn Asp Asn Arg
                85                  90                  95

Ala Ser Arg Ala Ala Met Asn Leu Leu Ala Asn Ala Gln Ile Pro Val
```

```
            100                 105                 110
Arg Thr Asn Gly Ala Tyr Lys Ile Gln His Asp Lys Val Ile Thr
            115                 120                 125

Asp Gly Gln Asn Val Glu Thr Gly Ser Phe Asn Tyr Ser Ala Ser
            130                 135                 140

Ala Lys Ala Asn Ser Glu Asn Ala Val Val Met Trp Asp Val Pro Ala
145                 150                 155                 160

Glu Ala Ser Val Tyr Leu Glu His Trp Gln Ser Arg Trp Val Gln Gly
                    165                 170                 175

Gln Pro Tyr Gln Pro Thr Tyr
            180

<210> SEQ ID NO 35
<211> LENGTH: 168
<212> TYPE: PRT
<213> ORGANISM: Pseudomonas amygdali

<400> SEQUENCE: 35

Met Ala Ser Val Leu Leu Cys Asn Leu Thr Phe Thr Val Gln Ala Ala
1               5                   10                  15

Glu Ile Gln Val Gly Phe Ser Pro Glu Gly Ser Ala Glu Gln Leu Val
            20                  25                  30

Leu Asn Val Ile Gln Arg Ala Arg Gln Gln Ile Arg Leu Met Ala Tyr
        35                  40                  45

Ser Phe Thr Ser Pro Ser Val Val Lys Ala Leu Val Gln Ala Lys Arg
    50                  55                  60

Arg Gly Val Asp Val Gln Val Val Asp Ala His Gly Asn Asp Asn
65                  70                  75                  80

Arg Ala Ser Arg Ala Ala Met Asn Leu Leu Ala Asn Ala Gln Ile Pro
                85                  90                  95

Val Arg Thr Asn Ala Ala Tyr Lys Ile Gln His Asp Lys Val Ile Ile
            100                 105                 110

Thr Asp Gly Gln Asn Val Glu Thr Gly Ser Phe Asn Tyr Ser Ala Ser
        115                 120                 125

Ala Ala Lys Ala Asn Ser Glu Asn Ala Val Val Met Trp Asp Val Pro
    130                 135                 140

Ala Val Ala Ser Val Tyr Leu Glu His Trp Gln Ser Arg Trp Val Gln
145                 150                 155                 160

Gly Gln Pro Tyr Gln Pro Thr Tyr
                165

<210> SEQ ID NO 36
<211> LENGTH: 165
<212> TYPE: PRT
<213> ORGANISM: Pseudomonas coronafaciens

<400> SEQUENCE: 36

Met Leu Leu Cys Asn Leu Thr Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
    50                  55                  60

Asp Val Gln Val Val Asp Ala His Gly Asn Asp Asn Arg Ala Ser
```

```
                65                  70                  75                  80
Arg Ala Ala Met Asn Leu Leu Ala Asn Ala Gln Ile Pro Val Arg Thr
                85                  90                  95

Asn Ala Ala Tyr Lys Ile Gln His Asp Lys Val Ile Ile Thr Asp Gly
            100                 105                 110

Gln Asn Val Glu Thr Gly Ser Phe Asn Tyr Ser Ala Ser Ala Ala Lys
            115                 120                 125

Ala Asn Ser Glu Asn Ala Val Val Met Trp Asp Val Pro Ala Val Ala
130                 135                 140

Ser Val Tyr Leu Glu His Trp Gln Ser Arg Trp Val Gln Gly Gln Pro
145                 150                 155                 160

Tyr Gln Pro Thr Tyr
                165
```

<210> SEQ ID NO 37
<211> LENGTH: 183
<212> TYPE: PRT
<213> ORGANISM: Pseudomonas syringae

<400> SEQUENCE: 37

```
Met Thr Ala Leu Ser Ala Leu Thr Arg Ser Leu Ser Arg Gly Leu Val
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Met Met Ala Tyr Ser
50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180
```

<210> SEQ ID NO 38
<211> LENGTH: 193
<212> TYPE: PRT
<213> ORGANISM: Pseudomonas amygdali

<400> SEQUENCE: 38

```
Met Ala Arg Thr Arg Thr Ala Gly Arg Val Met Thr Ile Leu Ser Ala
1               5                   10                  15

Leu Thr Arg Pro Leu Ser Arg Gly Leu Val Ala Ser Val Leu Leu Cys
                20                  25                  30

Asn Leu Ala Phe Thr Val Gln Ala Ala Glu Ile Gln Val Gly Phe Ser
```

```
            35                  40                  45
Pro Glu Gly Ser Ala Glu Gln Leu Val Leu Asn Val Ile Gln Arg Ala
 50                  55                  60
Arg Gln Gln Ile Arg Leu Met Ala Tyr Ser Phe Thr Ser Pro Ser Val
 65                  70                  75                  80
Val Lys Ala Leu Val Gln Ala Lys Arg Arg Gly Val Asp Val Gln Val
                 85                  90                  95
Val Val Asp Ala His Gly Asn Asp Asn Arg Ala Ser Arg Ala Ala Met
                100                 105                 110
Asn Leu Leu Ala Asn Ala Gln Ile Pro Val Arg Thr Asn Ala Ala Tyr
                115                 120                 125
Lys Ile Gln His Asp Lys Val Ile Ile Thr Asp Gly Gln Asn Val Glu
                130                 135                 140
Thr Gly Ser Phe Asn Tyr Ser Ser Ala Ala Lys Ala Asn Ser Glu
145                 150                 155                 160
Asn Ala Val Val Met Trp Asp Val Pro Ala Val Ala Ser Val Tyr Leu
                165                 170                 175
Glu His Trp Gln Ser Arg Trp Leu Gln Gly Gln Pro Tyr Gln Pro Thr
                180                 185                 190
Tyr

<210> SEQ ID NO 39
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 39

Met Thr Ala Leu Ser Ala Leu Thr Arg Pro Leu Ser Arg Gly Leu Val
 1               5                  10                  15
Ala Ser Val Leu Leu Cys Asn Leu Thr Phe Thr Val Gln Ala Ala Glu
                 20                  25                  30
Ile Gln Val Gly Phe Ser Pro Glu Gly Ser Ala Glu Gln Leu Val Leu
                 35                  40                  45
Asn Val Ile Gln Arg Ala Arg Gln Gln Ile Arg Leu Met Ala Tyr Ser
 50                  55                  60
Phe Thr Ser Pro Ser Val Val Lys Ala Leu Val Gln Ala Lys Arg Arg
 65                  70                  75                  80
Gly Val Asp Val Gln Val Val Asp Ala His Gly Asn Asp Asn Arg
                 85                  90                  95
Ala Ser Arg Ala Ala Met Asn Leu Leu Ala Asn Ala Gln Ile Pro Val
                100                 105                 110
Arg Thr Asn Ala Ala Tyr Lys Ile Gln His Asp Lys Val Ile Ile Thr
                115                 120                 125
Asp Gly Gln Asn Val Glu Thr Gly Ser Phe Asn Tyr Ser Ala Ser Ala
                130                 135                 140
Ala Lys Ala Asn Ser Glu Asn Ala Val Val Met Trp Asp Val Pro Ala
145                 150                 155                 160
Val Ala Ser Val Tyr Leu Glu His Trp Gln Ser Arg Trp Met Gln Gly
                165                 170                 175
Gln Pro Tyr Gln Pro Thr Tyr
                180
```

<210> SEQ ID NO 40
<211> LENGTH: 183
<212> TYPE: PRT
<213> ORGANISM: Pseudomonas amygdali

<400> SEQUENCE: 40

Met Thr Ile Leu Ser Ala Leu Thr Arg Pro Leu Ser Arg Gly Leu Val
1               5                   10                  15

Ala Ser Val Leu Leu Cys Asn Leu Ala Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Leu Gln Gly
                165                 170                 175

Gln Pro Tyr Gln Pro Thr Tyr
            180

<210> SEQ ID NO 41
<211> LENGTH: 183
<212> TYPE: PRT
<213> ORGANISM: Pseudomonas coronafaciens

<400> SEQUENCE: 41

Met Thr Ala Leu Ser Ala Leu Thr Arg Ser Leu Ser Arg Gly Leu Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Ser Ser Glu Asn Ala Val Val Met Trp Asp Val Pro Ala

```
145                 150                 155                 160
Val Ala Ser Val Tyr Leu Glu His Trp Gln Ser Arg Trp Val Gln Gly
                165                 170                 175
Gln Pro Tyr Gln Pro Thr Tyr
            180

<210> SEQ ID NO 42
<211> LENGTH: 169
<212> TYPE: PRT
<213> ORGANISM: Unknown
<220> FEATURE:
<223> OTHER INFORMATION: Description of Unknown:
      Pseudomonas syringae group genomosp. 3 sequence

<400> SEQUENCE: 42

Met Val Ala Ser Val Leu Leu Cys Asn Leu Thr Phe Thr Val Gln Ala
1               5                   10                  15

Ala Glu Ile Gln Val Gly Phe Ser Pro Glu Gly Ser Ala Glu Gln Leu
            20                  25                  30

Val Leu Asn Val Ile Gln Arg Ala Arg Gln Gln Ile Arg Met Met Ala
        35                  40                  45

Tyr Ser Phe Thr Ser Pro Ser Val Val Lys Ala Leu Val Gln Ala Lys
50                  55                  60

Arg Arg Gly Val Asp Val Gln Val Val Asp Ala His Gly Asn Asp
65                  70                  75                  80

Asn Arg Ala Ser Arg Ala Ala Met Asn Leu Leu Ala Asn Ala Gln Ile
                85                  90                  95

Pro Val Arg Thr Asn Ala Ala Tyr Lys Ile Gln His Asp Lys Val Ile
            100                 105                 110

Ile Thr Asp Gly Gln Asn Val Glu Thr Gly Ser Phe Asn Tyr Ser Ala
        115                 120                 125

Ser Ala Ala Lys Ala Asn Ser Glu Asn Ala Val Val Met Trp Asp Val
130                 135                 140

Pro Ala Val Ala Ser Val Tyr Leu Glu His Trp Gln Ser Arg Trp Val
145                 150                 155                 160

Gln Gly Gln Pro Tyr Gln Pro Thr Tyr
                165

<210> SEQ ID NO 43
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 43

Met Thr Ala Leu Ser Ala Leu Thr Arg Pro Leu Ser Arg Trp Met Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Met Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Val Asp Ala His Gly Asn Asp Asn Arg
```

```
                    85                  90                  95
Ala Ser Arg Ala Ala Met Asn Leu Leu Ala Asn Ala Gln Ile Pro Val
                100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 44
<211> LENGTH: 165
<212> TYPE: PRT
<213> ORGANISM: Pseudomonas amygdali

<400> SEQUENCE: 44

Met Leu Leu Cys Asn Leu Ala Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
    50                  55                  60

Asp Val Gln Val Val Asp Ala His Gly Asn Asp Asn Arg Ala Ser
65                  70                  75                  80

Arg Ala Ala Met Asn Leu Leu Ala Asn Ala Gln Ile Pro Val Arg Thr
                85                  90                  95

Asn Ala Ala Tyr Lys Ile Gln His Asp Lys Val Ile Ile Thr Asp Gly
            100                 105                 110

Gln Asn Val Glu Thr Gly Ser Phe Asn Tyr Ser Ala Ser Ala Ala Lys
        115                 120                 125

Ala Asn Ser Glu Asn Ala Val Val Met Trp Asp Val Pro Ala Val Ala
    130                 135                 140

Ser Val Tyr Leu Glu His Trp Gln Ser Arg Trp Leu Gln Gly Gln Pro
145                 150                 155                 160

Tyr Gln Pro Thr Tyr
                165

<210> SEQ ID NO 45
<211> LENGTH: 165
<212> TYPE: PRT
<213> ORGANISM: Pseudomonas coronafaciens

<400> SEQUENCE: 45

Met Leu Leu Cys Asn Leu Thr Phe Thr Val Gln Ala Ala Glu Ile Gln
1               5                   10                  15

Val Gly Phe Ser Pro Glu Gly Ser Ala Glu Gln Leu Val Leu Asn Val
            20                  25                  30

Ile Gln Arg Ala Arg Gln Gln Ile Arg Leu Met Ala Tyr Ser Phe Thr
        35                  40                  45

Ser Pro Ser Val Val Lys Ala Leu Val Gln Ala Lys Arg Arg Gly Val
```

```
                50                  55                  60
Asp Val Gln Val Val Asp Ala His Gly Asn Asp Asn Arg Ala Ser
 65                  70                  75                  80

Arg Ala Ala Met Asn Leu Leu Ala Asn Ala Gln Ile Pro Val Arg Thr
                 85                  90                  95

Asn Ala Ala Tyr Lys Ile Gln His Asp Lys Val Ile Ile Thr Asp Gly
                100                 105                 110

Gln Asn Val Glu Thr Gly Ser Phe Asn Tyr Ser Ala Ser Ala Lys
            115                 120                 125

Ala Ser Ser Glu Asn Ala Val Val Met Trp Asp Val Pro Ala Val Ala
            130                 135                 140

Ser Val Tyr Leu Glu His Trp Gln Ser Arg Trp Val Gln Gly Gln Pro
145                 150                 155                 160

Tyr Gln Pro Thr Tyr
                165

<210> SEQ ID NO 46
<211> LENGTH: 183
<212> TYPE: PRT
<213> ORGANISM: Pseudomonas syringae

<400> SEQUENCE: 46

Met Thr Ile Leu Ser Ala Leu Thr Arg Pro Leu Ser Arg Gly Leu Val
 1               5                  10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Arg Ala Arg Gln Gln Ile Arg Leu Met Ala Tyr Ser
         50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
                 85                  90                  95

Ala Ser Arg Ala Ala Met Asn Leu Leu Ala Asn Ala Gln Ile Pro Val
                100                 105                 110

Arg Thr Asn Gly Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
130                 135                 140

Ala Lys Ala Asn Ser Glu Asn Ala Val Val Met Trp Glu Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Pro Tyr
            180

<210> SEQ ID NO 47
<211> LENGTH: 183
<212> TYPE: PRT
<213> ORGANISM: Pseudomonas syringae

<400> SEQUENCE: 47

Met Thr Ala Leu Ser Ala Leu Thr Arg Pro Leu Ser Arg Gly Leu Leu
 1               5                  10                  15

Ala Ser Val Leu Leu Cys Asn Leu Thr Phe Thr Val Gln Ala Ala Glu
```

```
            20                  25                  30
Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Asp Val Pro Ala
145                 150                 155                 160

Glu Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 48
<211> LENGTH: 183
<212> TYPE: PRT
<213> ORGANISM: Pseudomonas amygdali

<400> SEQUENCE: 48

Met Thr Ile Leu Ser Ala Leu Thr Arg Pro Leu Ser Arg Gly Leu Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
        130                 135                 140

Ala Lys Ala Asn Ser Glu Asn Ala Val Val Met Trp Gly Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 49
<211> LENGTH: 183
```

```
<212> TYPE: PRT
<213> ORGANISM: Unknown
<220> FEATURE:
<223> OTHER INFORMATION: Description of Unknown:
      Pseudomonas syringae group sequence

<400> SEQUENCE: 49

Met Thr Ile Leu Ser Ala Leu Thr Arg Pro Leu Ser Arg Gly Leu Val
1               5                   10                  15

Ala Ser Val Leu Leu Cys Asn Leu Ala Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Gly Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 50
<211> LENGTH: 169
<212> TYPE: PRT
<213> ORGANISM: Unknown
<220> FEATURE:
<223> OTHER INFORMATION: Description of Unknown:
      Pseudomonas sequence

<400> SEQUENCE: 50

Met Val Ala Ser Val Leu Leu Cys Asn Leu Thr Phe Thr Val Gln Ala
1               5                   10                  15

Ala Glu Ile Gln Val Gly Phe Ser Pro Glu Gly Ser Ala Glu Gln Leu
            20                  25                  30

Val Leu Asn Val Ile Gln Gly Ala Arg Gln Gln Ile Arg Leu Met Ala
        35                  40                  45

Tyr Ser Phe Thr Ser Pro Ser Val Val Lys Ala Leu Val Gln Ala Lys
    50                  55                  60

Arg Arg Gly Val Asp Val Gln Val Val Asp Ala His Gly Asn Asp
65                  70                  75                  80

Asn Arg Ala Ser Arg Ala Ala Met Asn Leu Leu Ala Asn Ala Gln Ile
                85                  90                  95

Pro Val Arg Thr Asn Ala Ala Tyr Lys Ile Gln His Asp Lys Val Ile
            100                 105                 110

Ile Thr Asp Gly Gln Asn Val Glu Thr Gly Ser Phe Asn Tyr Ser Ala
        115                 120                 125
```

```
Ser Ala Ala Lys Ala Asn Ser Glu Asn Ala Val Val Met Trp Asp Val
    130                 135                 140

Pro Ala Val Ala Ser Val Tyr Leu Glu His Trp Gln Ser Arg Trp Val
145                 150                 155                 160

Gln Gly Gln Pro Tyr Gln Pro Thr Tyr
                165
```

<210> SEQ ID NO 51
<211> LENGTH: 204
<212> TYPE: PRT
<213> ORGANISM: Pseudomonas cannabina

<400> SEQUENCE: 51

```
Met Leu Arg Leu Ser Gln Arg Gly His Ala Met Ile Glu Pro Leu Val
1               5                   10                  15

Gln Phe Ser Pro Ala Ser Leu Ala Asn Lys Ala Arg Ser Ser Ser Thr
                20                  25                  30

Val Arg Ala Leu Val Ala Ser Val Leu Leu Cys Asn Leu Thr Phe Thr
            35                  40                  45

Val Gln Ala Ala Glu Ile Gln Val Gly Phe Ser Pro Glu Gly Ser Ala
        50                  55                  60

Glu Gln Leu Val Leu Asn Val Ile Gln Gly Ala Arg Gln Gln Ile Arg
65                  70                  75                  80

Leu Met Ala Tyr Ser Phe Thr Ser Pro Ser Val Val Lys Ala Leu Val
                85                  90                  95

Gln Ala Lys Arg Arg Gly Val Asp Val Gln Val Val Val Asp Ala His
                100                 105                 110

Gly Asn Asp Asn Arg Ala Ser Arg Ala Ala Met Asn Leu Leu Ala Asn
            115                 120                 125

Ala Gln Ile Pro Val Arg Thr Asn Ala Ala Tyr Lys Ile Gln His Asp
        130                 135                 140

Lys Val Ile Ile Thr Asp Gly Gln Asn Val Glu Thr Gly Ser Phe Asn
145                 150                 155                 160

Tyr Ser Ala Ser Ala Ala Lys Ala Asn Ser Glu Asn Ala Val Val Met
                165                 170                 175

Trp Asp Val Pro Ala Val Ala Ser Val Tyr Leu Glu His Trp Gln Ser
                180                 185                 190

Arg Trp Val Gln Gly Gln Pro Tyr Gln Pro Thr Tyr
            195                 200
```

<210> SEQ ID NO 52
<211> LENGTH: 183
<212> TYPE: PRT
<213> ORGANISM: Unknown
<220> FEATURE:
<223> OTHER INFORMATION: Description of Unknown:
    Pseudomonas syringae group genomosp. 3 sequence

<400> SEQUENCE: 52

```
Met Thr Ala Leu Ser Ala Leu Thr Arg Ser Leu Ser Arg Gly Leu Leu
1               5                   10                  15

Ala Ser Val Leu Leu Cys Asn Leu Thr Phe Thr Val Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Gly Ala Arg Gln Gln Ile Arg Leu Met Ala Tyr Ser
        50                  55                  60
```

-continued

```
Phe Thr Ser Pro Ser Val Lys Ala Leu Val Gln Ala Lys Arg Arg
 65                  70                  75                  80

Gly Val Asp Val Gln Val Val Asp Ala His Gly Asn Asp Ser Arg
                 85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
                180

<210> SEQ ID NO 53
<211> LENGTH: 237
<212> TYPE: PRT
<213> ORGANISM: Pseudomonas savastanoi

<400> SEQUENCE: 53

Met Tyr Cys Arg Ser Arg Pro Thr Ser Phe Lys Pro Trp Arg Cys Arg
 1               5                  10                  15

Lys His Arg Phe Arg Tyr Arg Ser Arg Ala Thr Thr Cys Arg Pro Cys
                20                  25                  30

Ala Met Leu Arg Leu Ser Gln Arg Gly His Ala Met Ile Glu Pro Leu
            35                  40                  45

Val Gln Phe Ser Pro Ala Ser Leu Ala Asn Lys Ala Arg Ser Ser Ser
    50                  55                  60

Thr Val Arg Ala Leu Val Ala Ser Val Leu Leu Cys Asn Leu Thr Phe
 65                  70                  75                  80

Thr Val Gln Ala Ala Glu Ile Gln Val Gly Phe Ser Pro Glu Gly Ser
                 85                  90                  95

Ala Glu Gln Leu Val Leu Asn Val Ile Gln Gly Ala Arg Gln Gln Ile
            100                 105                 110

Arg Leu Met Ala Tyr Ser Phe Thr Ser Pro Ser Val Val Lys Ala Leu
        115                 120                 125

Val Gln Ala Lys Arg Arg Gly Val Asp Val Gln Val Val Asp Ala
    130                 135                 140

His Gly Asn Asp Asn Arg Ala Ser Arg Ala Ala Met Asn Leu Leu Ala
145                 150                 155                 160

Asn Ala Gln Ile Pro Val Arg Thr Asn Ala Ala Tyr Lys Ile Gln His
                165                 170                 175

Asp Lys Val Ile Ile Thr Asp Gly Gln Asn Val Glu Thr Gly Ser Phe
            180                 185                 190

Asn Tyr Ser Ala Ser Ala Ala Lys Ala Asn Ser Glu Asn Ala Val Val
        195                 200                 205

Met Trp Asp Val Pro Ala Val Ala Ser Val Tyr Leu Glu His Trp Gln
    210                 215                 220

Ser Arg Trp Val Gln Gly Gln Pro Tyr Gln Pro Thr Tyr
225                 230                 235

<210> SEQ ID NO 54
```

```
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 54
```

Met Thr Ala Leu Ser Ala Leu Thr Arg Pro Leu Ser Arg Gly Leu Val
1               5                   10                  15

Ala Ser Val Leu Leu Cys Asn Leu Thr Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Asn
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Met Gln Gly
                165                 170                 175

Gln Pro Tyr Gln Pro Thr Tyr
            180

```
<210> SEQ ID NO 55
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 55
```

Met Thr Gly Leu Ser Thr Leu Thr Arg Pro Phe Ser Arg Gly Leu Val
1               5                   10                  15

Ala Ser Val Leu Leu Cys His Leu Thr Phe Thr Val Gln Ala Ala Glu
            20                  25                  30

Ile Glu Val Gly Phe Ser Pro Glu Gly Ser Ala Glu Gln Leu Val Leu
        35                  40                  45

Asn Val Ile Gln Gly Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

```
Asp Gly Gln Asn Val Glu Thr Gly Ser Phe Asn Tyr Ser Ala Ser Ala
            130                 135                 140

Ala Lys Ala Asn Ser Glu Asn Ala Val Val Met Trp Asp Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Thr Tyr
            180

<210> SEQ ID NO 56
<211> LENGTH: 194
<212> TYPE: PRT
<213> ORGANISM: Pseudomonas syringae

<400> SEQUENCE: 56

Met Ile Glu Pro Leu Val Gln Phe Ser Pro Ala Ser Leu Ala Asn Lys
1               5                   10                  15

Ala Arg Ser Ser Ser Thr Val Arg Ala Leu Val Ala Ser Val Leu Leu
            20                  25                  30

Cys Asn Leu Thr Phe Thr Val Gln Ala Ala Glu Ile Gln Val Gly Phe
        35                  40                  45

Ser Pro Glu Gly Ser Ala Glu Gln Leu Val Leu Asn Val Ile Gln Gly
    50                  55                  60

Ala Arg Gln Gln Ile Arg Leu Met Ala Tyr Ser Phe Thr Ser Pro Ser
65                  70                  75                  80

Val Val Lys Ala Leu Val Gln Ala Lys Arg Arg Gly Val Asp Val Gln
                85                  90                  95

Val Val Val Asp Ala His Gly Asn Asp Ser Arg Ala Ser Arg Ala Ala
            100                 105                 110

Met Asn Leu Leu Ala Asn Ala Gln Ile Pro Val Arg Thr Asn Ala Ala
        115                 120                 125

Tyr Lys Ile Gln His Asp Lys Val Ile Ile Thr Asp Gly Gln Asn Val
    130                 135                 140

Glu Thr Gly Ser Phe Asn Tyr Ser Ala Ser Ala Ala Lys Ala Asn Ser
145                 150                 155                 160

Glu Asn Ala Val Val Met Trp Asp Val Pro Ala Val Ala Ser Val Tyr
                165                 170                 175

Leu Glu His Trp Gln Ser Arg Trp Val Gln Gly Gln Pro Tyr Gln Pro
            180                 185                 190

Thr Tyr

<210> SEQ ID NO 57
<211> LENGTH: 169
<212> TYPE: PRT
<213> ORGANISM: Unknown
<220> FEATURE:
<223> OTHER INFORMATION: Description of Unknown:
      Pseudomonas syringae group sequence

<400> SEQUENCE: 57

Met Val Ala Ser Val Leu Leu Cys Asn Leu Thr Phe Thr Val Gln Ala
1               5                   10                  15

Ala Glu Ile Gln Val Gly Phe Ser Pro Glu Gly Ser Ala Glu Gln Leu
            20                  25                  30

Val Leu Asn Val Ile Gln Gly Ala Arg Gln Gln Ile Arg Leu Met Ala
        35                  40                  45
```

```
Tyr Ser Phe Thr Ser Pro Ser Val Val Lys Ala Leu Val Gln Ala Lys
             50                  55                  60

Arg Arg Gly Val Asp Val Gln Val Val Asp Ala His Gly Asn Asp
 65                  70                  75                  80

Ser Arg Ala Ser Arg Ala Ala Met Asn Leu Leu Ala Asn Ala Gln Ile
                 85                  90                  95

Pro Val Arg Thr Asn Ala Ala Tyr Lys Ile Gln His Asp Lys Val Ile
            100                 105                 110

Ile Thr Asp Gly Gln Asn Val Glu Thr Gly Ser Phe Asn Tyr Ser Ala
            115                 120                 125

Ser Ala Ala Lys Ala Asn Ser Glu Asn Ala Val Val Met Trp Asp Val
130                 135                 140

Pro Ala Val Ala Ser Val Tyr Leu Glu His Trp Gln Ser Arg Trp Val
145                 150                 155                 160

Gln Gly Gln Pro Tyr Gln Pro Thr Tyr
                165

<210> SEQ ID NO 58
<211> LENGTH: 165
<212> TYPE: PRT
<213> ORGANISM: Pseudomonas amygdali

<400> SEQUENCE: 58

Met Leu Leu Cys Asn Leu Thr Phe Thr Val Gln Ala Ala Glu Ile Gln
1               5                  10                  15

Val Gly Phe Ser Pro Glu Gly Ser Ala Glu Gln Leu Val Leu Asn Val
             20                  25                  30

Ile Gln Gly Ala Arg Gln Gln Ile Arg Leu Met Ala Tyr Ser Phe Thr
             35                  40                  45

Ser Pro Ser Val Val Lys Ala Leu Val Gln Ala Lys Arg Arg Gly Val
         50                  55                  60

Asp Val Gln Val Val Asp Ala His Gly Asn Asp Ser Arg Ala Ser
 65                  70                  75                  80

Arg Ala Ala Met Asn Leu Leu Ala Asn Ala Gln Ile Pro Val Arg Thr
                 85                  90                  95

Asn Ala Ala Tyr Lys Ile Gln His Asp Lys Val Ile Ile Thr Asp Gly
            100                 105                 110

Gln Asn Val Glu Thr Gly Ser Phe Asn Tyr Ser Ala Ser Ala Ala Lys
            115                 120                 125

Ala Asn Ser Glu Asn Ala Val Val Met Trp Asp Val Pro Ala Val Ala
130                 135                 140

Ser Val Tyr Leu Glu His Trp Gln Ser Arg Trp Val Gln Gly Gln Pro
145                 150                 155                 160

Tyr Gln Pro Thr Tyr
                165

<210> SEQ ID NO 59
<211> LENGTH: 183
<212> TYPE: PRT
<213> ORGANISM: Pseudomonas amygdali

<400> SEQUENCE: 59

Met Thr Ala Leu Ser Ala Leu Thr Arg Pro Phe Ser Arg Gly Leu Val
1               5                  10                  15

Ala Ser Val Leu Leu Cys Asn Leu Thr Phe Thr Val Gln Ala Ala Glu
             20                  25                  30
```

```
Ile Gln Val Gly Phe Ser Pro Glu Gly Ser Ala Glu Gln Leu Val Leu
             35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
             85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
            130                 135                 140

Ala Lys Ala Asn Ser Glu Asn Ala Val Val Met Trp Gly Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Pro Tyr
            180

<210> SEQ ID NO 60
<211> LENGTH: 183
<212> TYPE: PRT
<213> ORGANISM: Unknown
<220> FEATURE:
<223> OTHER INFORMATION: Description of Unknown:
      Pseudomonas syringae group sequence

<400> SEQUENCE: 60

Met Thr Ile Leu Ser Ala Leu Thr Arg Pro Leu Ser Arg Gly Leu Val
 1               5                  10                  15

Ala Ser Val Leu Leu Cys Asn Leu Thr Phe Thr Val Gln Ala Ala Glu
             20                  25                  30

Ile Gln Val Gly Phe Ser Pro Glu Gly Ser Ala Glu Gln Leu Val Leu
             35                  40                  45

Asn Val Ile Gln Arg Ala Arg Gln Gln Ile Arg Leu Met Ala Tyr Ser
 50                  55                  60

Phe Thr Ser Pro Ser Val Val Lys Ala Leu Val Gln Ala Lys Arg Arg
 65                  70                  75                  80

Gly Val Asp Val Gln Val Val Asp Ala His Gly Asn Asp Asn Arg
             85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
            115                 120                 125

Asp Gly Gln Asn Val Glu Thr Gly Ser Phe Asn Tyr Ser Ala Ser Ala
            130                 135                 140

Ala Lys Ala Asn Ser Glu Asn Ala Val Val Met Trp Gly Val Pro Ala
145                 150                 155                 160

Val Ala Ser Val Tyr Leu Glu His Trp Gln Ser Arg Trp Val Gln Gly
                165                 170                 175

Gln Pro Tyr Gln Pro Pro Tyr
            180

<210> SEQ ID NO 61
```

```
<211> LENGTH: 181
<212> TYPE: PRT
<213> ORGANISM: Pseudomonas amygdali

<400> SEQUENCE: 61

Met Thr Ala Leu Ser Ala Leu Thr Arg Ser Leu Ser Arg Gly Leu Val
1               5                   10                  15

Ala Ser Val Leu Leu Cys Asn Leu Ser Phe Thr Val Gln Ala Ala Glu
            20                  25                  30

Ile Gln Val Gly Phe Ser Pro Glu Gly Ser Ala Glu Gln Leu Val Leu
        35                  40                  45

Asn Val Ile Gln Arg Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Asp Asn Arg
                85                  90                  95

Ala Ser Arg Ala Ala Met Leu Ala Asn Ala Gln Ile Pro Val Arg Thr
            100                 105                 110

Asn Ala Ala Tyr Lys Ile Gln His Asp Lys Val Ile Ile Thr Asp Gly
        115                 120                 125

Gln Asn Val Glu Thr Gly Ser Phe Asn Tyr Ser Ala Ser Ala Ala Lys
    130                 135                 140

Ala Asn Ser Glu Asn Ala Val Val Met Trp Asp Val Pro Ala Val Ala
145                 150                 155                 160

Ser Val Tyr Leu Glu His Trp Gln Ser Arg Trp Met Gln Gly Gln Pro
                165                 170                 175

Tyr Gln Pro Thr Tyr
            180

<210> SEQ ID NO 62
<211> LENGTH: 183
<212> TYPE: PRT
<213> ORGANISM: Pseudomonas caricapapayae

<400> SEQUENCE: 62

Met Thr Ala Leu Ser Ala Leu Thr Arg Pro Phe Ser Arg Gly Leu Val
1               5                   10                  15

Ala Ser Ala Leu Leu Cys His Leu Thr Phe Thr Val Gln Ala Ala Glu
            20                  25                  30

Ile Glu Val Gly Phe Ser Pro Glu Gly Ser Ala Glu Gln Leu Val Leu
        35                  40                  45

Asn Val Ile Gln Gln Ala Arg Gln Gln Ile Arg Leu Met Ala Tyr Ser
    50                  55                  60

Phe Thr Ser Pro Ser Val Val Lys Ala Leu Val Gln Ala Lys Arg Arg
65                  70                  75                  80

Gly Val Asp Val Gln Val Val Asp Ala His Gly Asn Glu Asn Arg
                85                  90                  95

Ala Ser Arg Ala Ala Met Asn Leu Leu Ala Asn Ala Gln Ile Pro Val
            100                 105                 110

Arg Thr Asn Ala Ala Tyr Lys Ile Gln His Asp Lys Val Ile Ile Thr
        115                 120                 125

Asp Gly Gln Asn Val Glu Thr Gly Ser Phe Asn Tyr Ser Ala Ser Ala
    130                 135                 140

Ala Lys Ala Asn Ser Glu Asn Ala Val Val Met Arg Asp Val Pro Ala
145                 150                 155                 160
```

```
Val Ala Ser Val Tyr Leu Glu His Trp Gln Ser Arg Trp Val Gln Gly
                165                 170                 175

Gln Pro Tyr Gln Pro Thr Tyr
            180
```

<210> SEQ ID NO 63
<211> LENGTH: 183
<212> TYPE: PRT
<213> ORGANISM: Unknown
<220> FEATURE:
<223> OTHER INFORMATION: Description of Unknown:
      Pseudomonas sequence

<400> SEQUENCE: 63

```
Met Ser Ser Phe Ser Ala Leu Thr Arg Pro Ile Ser Arg Gly Leu Met
1               5                   10                  15

Leu Ser Thr Leu Leu Phe Asn Leu Val Leu Thr Ala Gln Ala Ala Glu
                20                  25                  30

Ile Gln Val Gly Phe Ser Pro Glu Gly Ser Ala Glu Gln Leu Val Leu
            35                  40                  45

Asn Val Ile Gln Asp Ala Gln Gln Ile Arg Leu Met Gly Tyr Ser
 50                  55                  60

Phe Thr Ser Pro Lys Val Val Lys Ala Leu Val Ala Ala Gln Lys Arg
65                  70                  75                  80

Gly Val Asp Val Gln Val Val Leu Asp Ala His Gly Asn Glu Ser Arg
                85                  90                  95

Ala Ser Arg Ala Ala Met Asn Leu Leu Ala Lys Ala Gly Ile Gly Leu
            100                 105                 110

Arg Thr Asn Ala Ala Tyr Lys Ile Gln His Asp Lys Val Ile Ile Ser
            115                 120                 125

Asp Gly Gln Asn Val Glu Thr Gly Ser Phe Asn Tyr Ser Thr Ser Ala
        130                 135                 140

Ala Lys Ala Asn Ser Glu Asn Ala Leu Val Leu Trp Gly Phe Pro Ala
145                 150                 155                 160

Val Ala Ser Val Tyr Leu Glu His Trp Gln Ser Arg Trp Glu Gln Gly
                165                 170                 175

Gln Pro Tyr Gln Pro Thr Phe
            180
```

<210> SEQ ID NO 64
<211> LENGTH: 180
<212> TYPE: PRT
<213> ORGANISM: Pseudomonas sp.

<400> SEQUENCE: 64

```
Met Ser Cys Arg Ser Gly Thr Arg Val Gly Pro Ile Gly Phe Leu Leu
1               5                   10                  15

Ala Ser Leu Thr Phe Cys Gly Pro Ala Leu Ala Ala Glu Val Gln Val
                20                  25                  30

Gly Phe Ser Pro Glu Gly Ser Ala Glu Ala Leu Val Ile Asp Val Val
            35                  40                  45

Glu Ser Ala His Gln Gln Ile Arg Met Met Gly Tyr Ser Phe Thr Ser
 50                  55                  60

Pro Lys Val Val Lys Ala Leu Val Ala Ala Lys His Arg Gly Val Asp
65                  70                  75                  80

Val Gln Ile Val Leu Asp Ala His Gly Asn Glu Asn Lys Ala Ser Arg
                85                  90                  95
```

```
Ala Ala Met Asn Phe Ile Val Asn Ala Gly Ile Pro Leu Arg Thr Asn
            100                 105                 110

Asp Ala Phe Lys Ile Gln His Asp Lys Val Ile Ile Ser Asp Asn Leu
            115                 120                 125

Asn Val Gln Thr Gly Ser Phe Asn Tyr Ser Thr Ala Ala Arg Ser
130                 135                 140

Asn Ser Glu Asn Ala Val Val Met Trp Gly Phe Pro Glu Val Ala Ser
145                 150                 155                 160

Val Tyr Leu Gln His Trp Gln Ser Arg Trp Asp Gln Gly Arg Pro Tyr
                165                 170                 175

Gln Ser Gly Tyr
            180

<210> SEQ ID NO 65
<211> LENGTH: 179
<212> TYPE: PRT
<213> ORGANISM: Pseudomonas coleopterorum

<400> SEQUENCE: 65

Met Ile Arg Ala Thr Arg Arg Phe Leu Ile Pro Ala Pro Ile Gly Val
1               5                   10                  15

Leu Phe Leu Ile Ala Ser Ala Val Gln Ala Ala Gln Val Glu Val Gly
                20                  25                  30

Phe Ser Pro Glu Gly Ser Ala Glu Thr Leu Val Val Asn Val Ile Gln
            35                  40                  45

Lys Ala Glu His Gln Val Leu Leu Met Gly Tyr Ser Phe Thr Ser Pro
    50                  55                  60

Ser Val Val Lys Ala Leu Ile Ala Ala Lys Arg Arg Gly Val Asp Val
65                  70                  75                  80

Gln Val Val Leu Asp Ala Arg Gly Asn Glu Gly Lys Ser Ser Gln Ala
                85                  90                  95

Ala Met Asn Leu Ile Ala His Ala Gly Ile Ala Val Arg Thr Asn Ala
            100                 105                 110

Ala Tyr Lys Ile Gln His Asp Lys Val Ile Ile Thr Asp Gly Arg Asn
            115                 120                 125

Val Glu Thr Gly Ser Phe Asn Tyr Ser Ser Ala Ala Ala His Ser Asn
130                 135                 140

Ser Glu Asn Ala Leu Val Leu Trp Asp Val Pro Asp Val Ala Lys Val
145                 150                 155                 160

Tyr Thr Gln His Trp Gln Ser Arg Trp Asp Lys Gly Gln Ala Tyr Gln
                165                 170                 175

Ala Gly Tyr

<210> SEQ ID NO 66
<211> LENGTH: 184
<212> TYPE: PRT
<213> ORGANISM: Unknown
<220> FEATURE:
<223> OTHER INFORMATION: Description of Unknown:
      Enterobacteriaceae sequence

<400> SEQUENCE: 66

Met Ile Gln Arg Leu Lys Lys Arg Asn Phe Leu Phe Lys Ala Ala Leu
1               5                   10                  15

Val Ala Val Leu Tyr Gly Ser Ala Pro Ser Leu Phe Ala Ala
            20                  25                  30
```

```
Ser Ala Gln Val Gly Phe Ser Pro Glu Gly Thr Ala Gln Gln Leu Val
        35                  40                  45

Ile Asn Val Ile Gly Ser Ala Lys Asp Asn Ile Arg Met Met Ala Tyr
 50                  55                  60

Ser Phe Thr Ala Pro Asp Ile Met Lys Ala Leu Ile Ala Ala Lys Arg
 65                  70                  75                  80

Arg Gly Val Asp Val Lys Ile Val Val Asp Glu Asn Gly Asn Thr Gly
                     85                  90                  95

Arg Ala Ser Arg Ala Ala Met Asn Leu Val Thr Asn Ala Gly Ile Pro
                100                 105                 110

Leu Arg Val Asn Ser Asn Tyr Lys Ile Gln His Asp Lys Val Ile Ile
            115                 120                 125

Val Asp Gly Arg His Val Glu Thr Gly Ser Phe Asn Tyr Thr Ala Ser
130                 135                 140

Ala Glu Lys Tyr Asn Ser Glu Asn Ala Ile Val Met Trp Asp Ala Pro
145                 150                 155                 160

Glu Leu Ala Gly Gln Tyr Leu Lys His Trp Gln Ser Arg Trp Asn Gln
                165                 170                 175

Gly Gln Asp Phe Thr Pro Ser Tyr
                180

<210> SEQ ID NO 67
<211> LENGTH: 199
<212> TYPE: PRT
<213> ORGANISM: Citrobacter freundii

<400> SEQUENCE: 67

Met Ser Trp Cys Thr Trp Asn Thr Ala Arg Leu Leu Arg Phe Phe Met
 1               5                  10                  15

Ile Gln Arg Leu Lys Lys Arg Asn Phe Leu Phe Lys Ala Ala Leu Val
                 20                  25                  30

Ala Ala Val Leu Tyr Gly Ala Ser Ala Pro Ser Leu Phe Ala Ala Ser
            35                  40                  45

Ala Gln Val Gly Phe Ser Pro Glu Gly Thr Ala Gln Gln Leu Val Ile
 50                  55                  60

Asn Val Ile Gly Ser Ala Lys Asp Asn Ile Arg Met Met Ala Tyr Ser
 65                  70                  75                  80

Phe Thr Ala Pro Asp Ile Met Lys Ala Leu Ile Ala Ala Lys Arg Arg
                 85                  90                  95

Gly Val Asp Val Lys Ile Val Val Asp Glu Asn Gly Asn Thr Gly Arg
            100                 105                 110

Ala Ser Arg Ala Ala Met Asn Leu Val Thr Asn Ala Gly Ile Pro Leu
        115                 120                 125

Arg Val Asn Ser Asn Tyr Lys Ile Gln His Asp Lys Val Ile Ile Val
130                 135                 140

Asp Gly Arg His Val Glu Thr Gly Ser Phe Asn Tyr Thr Ala Ser Ala
145                 150                 155                 160

Glu Lys Tyr Asn Ser Glu Asn Ala Ile Val Met Trp Asp Ala Pro Glu
                165                 170                 175

Leu Ala Gly Gln Tyr Leu Lys His Trp Gln Ser Arg Trp Asn Gln Gly
            180                 185                 190

Arg Asp Phe Thr Pro Ser Tyr
        195

<210> SEQ ID NO 68
```

```
<211> LENGTH: 169
<212> TYPE: PRT
<213> ORGANISM: Acinetobacter nosocomialis

<400> SEQUENCE: 68
```

Met Val Ala Ala Val Leu Tyr Gly Ala Ser Ala Pro Ser Leu Phe Ala
1               5                   10                  15

Ala Ser Ala Gln Val Gly Phe Ser Pro Glu Gly Thr Ala Gln Gln Leu
            20                  25                  30

Val Ile Asn Val Ile Gly Ser Ala Lys Asp Asn Ile Arg Met Met Ala
        35                  40                  45

Tyr Ser Phe Thr Ala Pro Asp Ile Met Lys Ala Leu Ile Ala Ala Lys
    50                  55                  60

Arg Arg Gly Val Asp Val Lys Ile Val Val Asp Glu Asn Gly Asn Thr
65                  70                  75                  80

Gly Arg Ala Ser Arg Ala Ala Met Asn Leu Val Thr Asn Ala Gly Ile
                85                  90                  95

Pro Leu Arg Val Asn Ser Asn Tyr Lys Ile Gln His Asp Lys Val Ile
            100                 105                 110

Ile Val Asp Gly Arg His Val Glu Thr Gly Ser Phe Asn Tyr Thr Ala
        115                 120                 125

Ser Ala Glu Lys Tyr Asn Ser Glu Asn Ala Ile Val Met Trp Asp Ala
    130                 135                 140

Pro Glu Leu Ala Gly Gln Tyr Leu Lys His Trp Gln Ser Arg Trp Asn
145                 150                 155                 160

Gln Gly Arg Asp Phe Thr Pro Ser Tyr
                165

```
<210> SEQ ID NO 69
<211> LENGTH: 184
<212> TYPE: PRT
<213> ORGANISM: Escherichia coli

<400> SEQUENCE: 69
```

Met Ile Gln Arg Leu Lys Lys Arg Asn Phe Leu Phe Lys Ala Ala Leu
1               5                   10                  15

Val Ala Ala Val Leu Tyr Gly Ala Ala Ala Pro Ser Val Tyr Ala Ala
            20                  25                  30

Ser Ala Gln Val Gly Phe Ser Pro Glu Gly Thr Ala Gln Glu Leu Val
        35                  40                  45

Ile Asn Val Ile Gly Ser Ala Lys Glu Asn Ile Arg Met Met Ala Tyr
    50                  55                  60

Ser Phe Thr Ala Pro Asp Ile Met Lys Ala Leu Ile Ala Ala Lys Arg
65                  70                  75                  80

Arg Gly Val Asp Val Lys Ile Val Asp Glu Asn Gly Asn Thr Gly
                85                  90                  95

Arg Ala Ser Arg Ala Ala Met Asn Leu Val Thr Asn Ala Gly Ile Pro
            100                 105                 110

Leu Arg Val Asn Gly Asn Tyr Lys Ile Gln His Asp Lys Val Ile Ile
        115                 120                 125

Val Asp Gly Arg His Val Glu Thr Gly Ser Phe Asn Tyr Thr Ala Ser
    130                 135                 140

Ala Glu Lys Tyr Asn Ser Glu Asn Ala Ile Val Met Trp Asp Ala Pro
145                 150                 155                 160

Glu Leu Ala Ala Gln Tyr Gln Lys His Trp Gln Ser Arg Trp Asp Gln
                165                 170                 175

```
Gly Arg Asp Tyr Thr Pro Ser Tyr
            180

<210> SEQ ID NO 70
<211> LENGTH: 184
<212> TYPE: PRT
<213> ORGANISM: Klebsiella pneumoniae

<400> SEQUENCE: 70

Met Ile Gln Arg Leu Lys Lys Arg Asn Phe Leu Phe Lys Ala Ala Leu
1               5                   10                  15

Val Ala Ala Val Leu Tyr Gly Ala Ser Ala Pro Ser Leu Phe Ala Ala
            20                  25                  30

Ser Ala Gln Val Gly Phe Ser Pro Glu Gly Thr Ala Gln Gln Leu Val
        35                  40                  45

Ile Asn Val Ile Gly Ser Ala Lys Asp Asn Ile Arg Met Met Ala Tyr
    50                  55                  60

Ser Phe Thr Ala Pro Asp Ile Met Lys Ala Leu Ile Ala Ala Lys Arg
65                  70                  75                  80

Arg Gly Val Asp Val Lys Ile Val Val Asp Glu Asn Gly Asn Thr Gly
                85                  90                  95

Arg Ala Ser Arg Ala Ala Met Asn Leu Val Thr Asn Ala Gly Ile Pro
            100                 105                 110

Leu Arg Val Asn Ser Asn Tyr Lys Ile Gln His Asp Lys Val Ile Ile
        115                 120                 125

Val Asp Asp Arg His Val Glu Thr Gly Ser Phe Asn Tyr Thr Ala Ser
    130                 135                 140

Ala Glu Lys Tyr Asn Ser Glu Asn Ala Ile Val Met Trp Asp Ala Pro
145                 150                 155                 160

Glu Leu Ala Gly Gln Tyr Leu Lys His Trp Gln Ser Arg Trp Asn Gln
                165                 170                 175

Gly Arg Asp Phe Ile Pro Ser Tyr
            180

<210> SEQ ID NO 71
<211> LENGTH: 179
<212> TYPE: PRT
<213> ORGANISM: Salmonella enterica

<400> SEQUENCE: 71

Met Ser Ala Ser Leu Arg Ser Leu Ala Leu Val Phe Leu Ala Gly Ile
1               5                   10                  15

Pro Val Cys Thr Val Thr Ala Ala Ser Ile Gln Val Gly Phe Ser Pro
            20                  25                  30

Glu Gly Thr Ala Gln Gln Val Leu Asn Thr Ile Asn Gln Ser Arg
        35                  40                  45

Gln Ser Val Arg Met Met Ala Tyr Ser Phe Thr Ser Pro Glu Val Val
    50                  55                  60

Lys Ala Leu Ile Asn Ala Lys Lys Arg Gly Val Asp Val Arg Val Val
65                  70                  75                  80

Ile Asp Glu Lys Gly Asn Thr Cys Glu Lys Cys Lys Ala Ser Lys Ala
                85                  90                  95

Ala Met Asn Leu Leu Val Asn Ala Asp Ile Pro Leu Arg Thr Val Ser
            100                 105                 110

Lys Tyr Lys Ile Met His Asp Lys Val Ile Ile Thr Asp Gly Ala Asn
        115                 120                 125
```

```
Val Glu Thr Gly Ser Phe Asn Phe Ser Ser Ala Ala Asn Lys Ser Asn
    130                 135                 140

Ser Glu Asn Ala Ile Leu Ile Gln Asp Val Pro Glu Leu Ala Gln Gln
145                 150                 155                 160

Tyr Leu Gln His Trp Gln Ser Arg Trp Gln Ala Gly Arg Asp Trp Lys
                165                 170                 175

Ser Thr Tyr
```